US006207401B1

(12) United States Patent
Plowman et al.

(10) Patent No.: US 6,207,401 B1
(45) Date of Patent: Mar. 27, 2001

(54) DIAGNOSIS AND TREATMENT OF AUR-1 AND/OR AUR-2 RELATED DISORDERS

(75) Inventors: Gregory Plowman, San Carlos, CA (US); Kevin Mossie, Gauteng (ZA)

(73) Assignee: Sugen, Inc., Redwood, CA (US)

( * ) Notice: Subject to any disclaimer, the term of this patent is extended or adjusted under 35 U.S.C. 154(b) by 0 days.

(21) Appl. No.: 09/283,011

(22) Filed: Mar. 31, 1999

Related U.S. Application Data

(60) Division of application No. 09/012,135, filed on Jan. 22, 1998, which is a continuation-in-part of application No. 09/005,268, filed on Jan. 9, 1998, now abandoned, which is a continuation-in-part of application No. 08/755,728, filed on Nov. 25, 1996, now Pat. No. 5,962,312

(60) Provisional application No. 60/008,809, filed on Dec. 18, 1995, and provisional application No. 60/023,943, filed on Aug. 14, 1996.

(51) Int. Cl.$^7$ .................................................. C12Q 1/54
(52) U.S. Cl. ........................................................... 435/15
(58) Field of Search .................................................. 435/15

(56) References Cited

U.S. PATENT DOCUMENTS

| | | | |
|---|---|---|---|
| 4,343,940 | 8/1982 | Kreighbaum et al. | 544/283 |
| 4,376,110 | 3/1983 | David et al. | 436/513 |
| 4,447,608 | 5/1984 | Jones et al. | 544/287 |
| 4,757,072 | 7/1988 | Kabbe et al. | 514/257 |
| 4,945,050 | 7/1990 | Sanford et al. | 435/172.1 |
| 5,217,999 | 6/1993 | Levitzki et al. | 514/613 |
| 5,283,173 | 2/1994 | Fields et al. | 435/6 |
| 5,302,606 | 4/1994 | Spada et al. | 514/357 |
| 5,316,553 | 5/1994 | Kaul et al. | 8/639 |
| 5,330,992 | 7/1994 | Eissenstat et al. | 514/312 |

FOREIGN PATENT DOCUMENTS

| | | |
|---|---|---|
| 0 520 722 A1 | 6/1992 | (EP) . |
| 0 566 226 A1 | 1/1993 | (EP) . |
| 0 562 734 A1 | 3/1993 | (EP) . |
| 91/15495 | 10/1991 | (WO) . |
| 92/14748 | 9/1992 | (WO) . |
| 92/20642 | 11/1992 | (WO) . |
| 92/21660 | 12/1992 | (WO) . |
| 93/09236 | 5/1993 | (WO) . |
| 94/03427 | 2/1994 | (WO) . |
| 94/14808 | 7/1994 | (WO) . |
| 94/23039 | 10/1994 | (WO) . |
| 96/34985 | 7/1996 | (WO) . |
| 96/22976 | 8/1996 | (WO) . |

OTHER PUBLICATIONS

Abe et al., "Molecular Characterization of a Novel Metabotropic Glutamate Receptor mGluR5 Coupled to Insitol Pohosphate/Ca2+ Signal," *J. Biol. Chem.* 267(19):13361–13368 (1992).

Alberts, B. et al., *Molecular Biology of the Cell,* Second Edition, published 1989, by Garland Publishing (New York) pp. 265–266. (Table of Contents Only).

Allen et al., "Modulation of CD4 by suramin," *Clin. Exp. Immunol.* 91:141–146 (1991).

Altschul et al., "Basic Local Alignment Search Tool," *J. Mol. Biol.* 215:403–410 (1990).

Anafi et al., "Tyrphostin–Induced Inhibition of p210$^{bcr-abl}$ Tyrosine Kinase Activity Induces K562 to Differentiate," *Blood* 82:3524–3529 (1993).

Baker et al., "Induction of acetylcholine receptor clustering by native polystyrene beads," *Journal of Cell Science* 102:543–555 (1992).

Barker et al., "In vitro activity of non–glutamate containing quinazoline–based thymidylate synthase inhibitors," *Proceedings of the American Association for Cancer Research* 32:327 at abstract No. 1939 (1991).

Bayer et al., "The Avidin–Biotin Complex in Affinity Cytochemistry," *Methods in Enzymology* 62:308–319 (1979).

Benoist and Chambon, "In vivo sequence requirements of the SV40 early promoter region," *Nature* 290:304–310 (1981).

Bertino, "Toward Improved Selectivity in Cancer Chemotherapy: The Richard and Hinda Rosenthal Foundation Award Lecture," *Cancer Research* 39:293–304 (1979).

Bigner et al., "Structural Chromosomal Abnormalities in Human Medulloblastoma," *Cancer Genet Cytogenet* 30:91–101 (1988).

Bilder et al., "Tyrphostins inhibit PDGF–induced DNA synthesis and associated early events in smooth muscle cells," *Am. J. Physiol.* 260(Cell Physiol.29):C721–C730 (1991).

Bockmuhl et al, *Laryngorhinootologie* 75:408–414 (1996).

Bollon and Stauver, "DNA Transformation Efficiency of Various Bacterial and Yeast Host–Vector Systems," *Journal of Clinical Hematology and Oncology* 10(2&3):39–48 (1980).

Botstein et al., "Making Mutations in vitro and Putting Them Back into Yeast," *Miami Winter Symposia—From Gene to Protein: Translation into Biotechnology,* edited by Ahmad et al., Academic Press, 19:265–274 (1982).

(List continued on next page.)

Primary Examiner—Rebecca E. Prouty
Assistant Examiner—M. Monshipouri
(74) Attorney, Agent, or Firm—Foley & Lardner

(57) ABSTRACT

The present invention relates to AUR1 and/or AUR2 polypeptides, nucleic acids encoding such polypeptides, cells, tissues and animals containing such nucleic acids, antibodies to such polypeptides, assays utilizing such polypeptides, and methods relating to all of the foregoing. Methods for treatment, diagnosis, and screening are provided for AUR1 and/or AUR2 related diseases or conditions characterized by an abnormal interaction between a AUR1 and/or AUR2 polypeptide and a AUR1 and/or AUR2 binding partner.

6 Claims, 1 Drawing Sheet

OTHER PUBLICATIONS

Brinster et al., "Factors Affecting the Efficiency of Introducing Foreign DNA into Mice by Microinjecting Eggs," *Proc. Natl. Acad. Sci. USA* 82:4438–4442 (1985).

Broach, "The Yeast Plasmid $2\mu$ Circle," *Cell* 28:203–204 (1982).

Broach, In: *The Molecular Biology of the Yeast Saccharomyces: Life Cycle and Inheritance*, Cold Spring Harbor Laboratory, Cold Spring Harbor, NY p. 445–470 (1981).

Bryckaert et al., *Experimental Cell Research* 199:255–261 (1992).

Bullock et al., "Techniques in Immunocytochemistry," Academic Press, Orlando, FL: vol. 1 (1982), vol. 2 (1983), vol. 3 (1985) (Table of Contents Only).

Burke et al., "Arylamides of Hydroxylated Isoquinolines as Protein–Tyrosine Kinase Inhibitors," *Bioorganic & Medical Chemistry Letters* 2(12):1771–1774 (1992).

Burke et al., "Bicyclic Compounds as Ring–Constrained Inhibitors of Proein–Tyrosine Kinase $p56^{lck\ 1}$," *Journal of Medicinal Chemistry* 36(4):425–432 (1993).

Capecchi, "High Efficiency Transformation by Direct Microinjection of DNA into Cultured Mammalian Cells," *Cell* 22:479–488 (1980).

Capecchi, "Altering the Genome by Homologous Recombination," *Science* 244:1288–1292 (1989).

Chan and Botstein, "Isolation and Characterization of Chromosome–Gain and Increase–in–Ploidy Mutants in Yeast," *Genetics* 135:677–691 (1993).

Chard, "An Introduction to Radioimmunoassay and Related Techniques," Elsevier Science Publishers, Amsterdam, The Netherlands (1986).

Chater et al., In: *Sixth International Symposium on Actinomycetales Biology*, Akademiai Kaido, Budapest, Hungary, pp. 45–54 (1986).

Chen and Okayama, "High–Efficiency Transformation of Mammalian Cells by Plasmid DNA," *Molecular and Cellular Biology* 7(8):2745–2752 (1987).

Chomczynski and Sacchi, "Single–Step Method of RNA Isolation by Acid Guanidinium Thiocyanate–Phenol–Chloroform Extraction," *Analytical Biochemistry* 162:156–159 (1987).

Chu et al., "Electroporation for the efficient transfection of mammalian cells with DNA," *Nucleic Acids Research* 15:1311–1326 (1987).

Courjal et al., "DNA amplifications at 20q13 and MDM2 define distinct subsets of evolved breast and ovarian tumours," *British Journal of Cancer* 74:1984–1989 (1996).

Cowley et al., "Activation of MAP Kinase Kinase Is Necessary and Sufficient for PC12 Differentiation and for Transformation of NIH 3T3 Cells," *Cell* 77:841–852 (1994).

Curiel et al., "Gene Transfer to Respiratory Epithelial Cells via the Receptor–mediated Endocytosis Pathway," *Am. J. Respir. Cell. Mol. Biol.* 6:247–252 (1992).

Curtin et al., "Inhibition of the growth of human hepatocellular carcinoma in vitro and in athymic mice by a quinazoline inhibitor of thymidylate synthase, CB3717," *Br. J. Cancer* 53:361–368 (1986).

Dolle et al., "5,7–Dimethoxy–3–(4–pyridinyl)quinoline is a Potent and Selective Inhibitor of Human Vascular –Type Platelet–Derived Growth Factor Receptor Tyrosine Kinase, "*J. Med. Chem.* 37:2627–2629 (1994).

Dong et al., "Activation of tumoricidal properties in macrophages by lipopolysaccharide requires protein–tyrosine kinase activity," *Journal of Leukocyte Biology* 53:53–60 (1993).

Dong et al., "Protein Tyrosine Kinase Inhibitors Decrease Induction of Nitric Oxide Synthase Activity in Lipopolysaccharide–Responsive and Lipopolysaccharide–Nonresponsive Murine Macrophages," *The Journal of Immunology* 151(5):2717–2724 (1993).

Elledge, "Cell Cycle Checkpoints: Preventing an Identity Crisis," *Science* 274:1664–1672 (1996).

Engvall and Perlmann, "Enzyme–Linked Immunosorbent Assay, ELISA. III. Quantitation of Specific Antibodies by Enzyme–Labeled Anti–Immunoglobulin in Antigen–Coated Tubes," *J. Immunology* 109:129–135 (1972) (mistakenly referred to as Engval).

Felgner and Ringold, "Catonic liposome–mediated transfection," *Nature* 337:387–388 (1989).

Felgner et al., "Lipofection: A Highly Efficient, Lipid–mediated DNA–transfection Procedure," *Proc. Natl. Acad. Sci. USA* 84:7413–7417 (1987).

Fernandes et al., "Biochemical and Antitumor Effects of 5,8–Dideazaisopteroylglutamate, a Unique Quinazoline Inhibitor of Thymidylate Synthase," *Cancer Research* 43:1117–1123 (1983).

Ferris et al., "Synthesis of Quinazoline Nucleosides from Ribose and Anthranilonitrile. Application of Phase–Transfer Catalysis in Nucleoside Synthesis," *J. Org. Chem.* 44(2):173–178 (1979).

Francisco et al., "Type 1 Protein Phosphatase Acts in Opposition to IPI1 Protein Kinase in Regulating Yeast Chromosome Segregation," *Molecular and Cellular Biology* 14(7):4731–4740 (1994).

Fry et al., "A Specific Inhibitor of the Epidermal Growth Factor Receptor Tyrosine Kinase," *Science* 265:1093–1095 (1994).

Gazit et al., "Tyrphostins 1. Synthesis and Biological Activity of Protein Tyrosine Kinase Inhibitors," *J. Med. Chem.* 32:2344–2352 (1989).

Gazit et al., "Tyrphostins. 3. Structure–Activity Relationship Studies of a –Substituted Benzylidenemalononitrile 5–S–Aryltyrphostins," *J. Med. Chem.* 36:3556–3564 (1993).

Malone et al., *Focus* 11, 66 (1989).

Gilman et al., "Isolation of sigma–28–specific promoters from *Bacillus subtilis* DNA," *Gene* 32:11–20 (1984).

Glick and Whitney, "Factors affecting the expression of foreign proteins in *Escherichia coli,*" *Journal of Industrial Microbiology* 1:277–282 (1987).

Glover et al., "Mutations in aurora Prevent Centrosome Separation Leading to the Formation of Monopolar Spindles," *Cell* 81:95–105 (1995).

Goding, "Conjugation of Antibodies with Fluorochromes: Modifications to the Standard Methods," *J. Immunological Methods* 13:215–226 (1976).

Gold et al., "Translational Initiation in Prokaryotes," *Ann. Rev. Microbiol.* 35:365–403 (1981).

Gopalan et al., "A Novel Mammalian, Mitotic–Spindle–associated Kinase is Related to Yeast and Fly Chromosome Segregation Regulators," *J. Cell. Biol.* 138:643–656 (1997).

Gottesman, "Bacterial Regulation: Global Regulatory networks," *Ann. Rev. Genet.* 18:415–441 (1984).

Gryczan, "Ch. 10—Molecular Cloning in *Bacillus subtilis,*" in *The Molecular Biology of the Bacilli,* edited by Dubnau, Academic Press, New York, pp. 307–329 (1982).

Hammer and Walling, "Regulation In Vivo of a Cloned Mammalian Gene: Cadmium Induces the Transcription of a Mouse Metallothionein Gene in SV40 Vectors," *J. of Molecular and Applied Genetics* 1:273–288 (1982).

Hammer et al., "Spontaneous Inflammatory Disease in Transgenic Rats Expressing HLA–B27 and Human B2m: An Animal Model of HLA–B27–Associated Human Disorders," *Cell* 63:1099–1112 (1990).

Hartwell and Kastan, "Cell Cycle Control and Cancer," *Science* 266:1821–1828 (1994).

Houdebine and Chourrout, "Trangenesis in Fish," *Experientia* 47:891–897 (1991).

Hunter, "Oncoprotein Networks," *Cell* 88:333–346 (1997).

Hurby et al., "Application of Synthetic Peptides: Antisense Peptides," In *Synthetic Peptides, A User's Guide,* W.H. Freeman, NY pp. 289–307 (1992), Grant G. (ed.).

Innis et al., *PCR Protocols: A Guide to Methods and Applications,* edited by Michael A. Innis et al., Academic Press, San Diego (1990) (Table of Contents Only).

Isola et al., "Genetic Aberrations Detected by Comparative Genomic Hybridization Predict Outcome in Node–Negative Breast Cancer," *American Journal of Pathology* 147:905–911 (1995).

Iwabuchi et al., "Genetic Analysis of Benign, Low–Grade, and High Grade Ovarian Tumors," *Cancer Research* 55:6172–6180 (1995).

Izaki, *Japanese Journal of Bacteriology* 33(6):729–742 (1978).

Jackman, "ICI D1694, a Quinazoline Antifolate Thymidylate Synthase Inhibitor That Is a Potent Inhibitor of L1210 Tumor Cell Growth in Vitro and in Vivo: A New Agent for Clinical Study," *Cancer Research* 51:5579–5586 (1991).

Jakoby and Wilchek (editors), *Affinity Techniques: Enzyme Purification: Part B,* Methods in Enzymology, vol. XXXIV, Academic Press, New York (1974) (Table of Contents Only).

James et al., "Comparative genomic hybridisation of ductal carcinoma in situ of the breast: identification of regions of DNA amplification and deletion in common with invasive breast carcinoma," *Oncogene* 14:1059–1065 (1997).

Jasny, "Insect Viruses Invade Biotechnology," *Science* 238:1653 (1987).

John and Twitty, "Plasmids as Epidemiologic Markers in Nosocomial Gram–Negative Bacilli: Experience at a University and Review of the Literature," *Reviews of Infectious Diseases* 8:693–704 (1986).

Johnston and Hopper, "Isolation of the yeast regulatory gene GAL4 and analysis of its dosage effects on the galactose/melibiose regulon," *Proc. Natl. Acad. Sci. USA* 79:6971–6975 (1982).

Jones et al., "Quinazoline Antifolates Inhibiting Thymidylate Synthase: Varation of the Amino Acid," *J. Med. Chem.* 29:1114–1118 (1986).

Joyner et al., "Production of a mutation in mouse En–2 gene by homologous recombination in embryonic stem cells," *Nature* 338:153–156 (1989).

Kallioniemi et al., "Detection and mapping of amplified DNA sequences in breast cancer by comparative genomic hybridization," *Proc. Natl. Acad. Sci. USA* 91:2156–2160 (1994).

Kasprzak et al., "Location of a Contact Site Between Actin and Myosin in the Three–Dimensional Structure of the Acto–S1 Complex," *Biochemistry* 28:9230–9238 (1989) (also referred to as Kaspczak).

Kaur, "Tyrphostin induced growth inhibition: correlation with effect on $p210^{bcr-abl}$ autokinase activity in K562 chronic myelogenous leukemia," *Anti–Cancer Drugs* 5:213–222 (1994).

Kendall and Cohen, "Plasmid Transfer in *Streptomyces lividans:* Identification of a kil–kor System Associated with the Transfer Region of PIJ101," *Journal of Bacteriology* 169:4177–4183 (1987).

Kimura et al., "Cell Cycle–dependent Expression and Spindle Pole Localization of a Novel Human Protein Kinase, Aik, Related to Aurora of Drosophila and Yeast Ip11," *J. Biol. Chem.* 272:13766–13771 (1997).

King et al., "Site–specific dephosphorylation and deactivation of the human insulin receptor tyrosine kinase by particulate and soluble phosphotyrosyl protein phosphatases," *Biochem. J.* 275:413–418 (1991).

Kinzler and Vogelstein, "Cancer–susceptibility Genes: Gatekeepers and caretakers," *Nature* 386:761–763 (1997).

Köhler (Kohler) and Milstein, "Continuous cultures of fused cells secreting antibody of predefined specificity," *Nature* 256:495–497 (1975).

Kuo et al., "Effects of signalling transduction modulators on the transformed phenotypes in v–H–ras–transformed NIH 3T3 cells," *Cancer Letters* 74:197–202 (1993).

Larramendy et al., "Gains, Losses, and Amplifications of DNA Sequences Evaluated by Comparative Genomic Hybridization in Chondrosarcomas," *American Journal of Pathology* 150:685–691 (1997).

Lee and Skibo, "Active–Site–Directed Reductive Alkylation of Xanthine Oxidase by Imidazo[4,5–g]quinazoline–4,9–diones Functionalized with a Leaving Group," *Biochemistry* 26:7355–7362 (1987).

Lemus et al., "Studies of Extended Quinone Methides. Synthesis and Physical Studies of Purine–like Monofunctional and Bifunctional Imidazo[4,5–g]quinazoline Reductive Alkylating Agents," *J. Org. Chem.* 54:3611–3618 (1989).

Levitzki, "Tyrphostins: tyrosine kinase blockers as novel antiproliferative agents and dissectors of signal transduction," *FASEB J.* 6:3275–3282 (1992).

Ley and Seng, "Synthesis Using Benzofuroxan," *Synthesis* 1975:415–422 (1975).

Lui et al., "Construction of a GAL1–Regulated Yeast cDNA Expression Library and its Application to the Identification of Genes Whose Overexpression Causes Lethality in Yeast," *Genetics* 132:665–673 (1992).

Lutz et al., "The Distribution of Two hnRNP–Associated Proteins Defined by a Monoclonal Antibody Is Altered in Heat–Shocked HeLa Cells," *Experimental Cell Research* 175:109–124 (1988).

Lyall et al., "Tyrphostins Inhibit Epidermal Growth Factor (EGF)–Receptor Tyrosine Kinase Activity in Living Cells and EGF–stimulated Cell Proliferation," *J. Biol. Chem.* 264:14503–14509 (1989).

Burke, et al. *J. Med. Chem.,* 36:425–432 (1993).

Maniatis, In:*Cell Biology: A Comprehensive Treatise,* vol. 3, Gene Sequence Expression, Academic Press, NY, pp. 563–608 (1980).

Markowitz et al., "Construction and Use of a Safe and Efficient Amphotropic Packaging Cell Line," *Virology* 167:400–406 (1988).

Maxwell et al., "$^{19}$F Nuclear Magnetic Resonance Imaging of Drug Distribution in Vivo: The Diposition of an Antifolate Anticancer Drug in Mice," *Magnetic Resonance in Medicine* 17:189–196 (1991).

McKnight, "Functional Relationships between Transcriptional Control Signals of the Thymidine Kinase Gene of Herpes Simplex Virus," *Cell* 31:355–365 (1992).

Miller and Rosman, "Improved Retroviral Vectors for Gene Transfer and Expression," *BioTechniques* 7(9):980–990 (1989).

Miller et al., In: *Genetic Engineering*, vol. 8, Plenum, Setlow et al., eds., pp. 277–297 (1986).

Miller, "Human gene therapy comes of age," *Nature* 357:455–460 (1992).

Mini et al., "Cytotoxic Effects of Folate Antagonists against Methotrexate–resistant Human Leukemic Lymphoblast CCRF–CEM Cell Lines," *Cancer Research* 45:325–330 (1985).

Mitelman et al, *Nature Genet.,* 15:417–474 (1997).

Mossie et al., "Colon carcinoma kinase–4 defines a new subclass of the receptor tyrosine kinase family," *Oncogene* 11(10):2179–2184 (1995).

Muleris et al., "Characteristic Chromosomal Imbalances in 18 Near–Diploid Colorectal Tumors," *Cancer Genet Cytogenet* 29:289–301 (1987).

Mulligan, "The Basic Science of Gene Therapy," *Science* 260–926–932 (1993).

Nelson, "Detection of Acridinium Esters by Chemiluminescence," *Nonisotopic DNA Probe Techniques,* ed. Larry J. Kricka, (San Diego:Academy Press, Inc.) pp. 275–310 (1992) (Table of Contents Only).

Okayama and Berg, "A cDNA Cloning Vector That Permits Expression of cDNA Inserts in Mammalian Cells," *Molecular and Cellular Biology* 3:280–289 (1983).

Pati, "Novel vectors for expression of cDNA encoding epitope–tagged proteins in mammalian cells," *Gene* 114:2856–288 (1992).

Peterson and Barnes, "Genistein and Biochanin A Inhibit the Growth of Human Prostate Cancer Cells but not Epidermal Growth Factor Receptor Tyrosine Autophosphorylation," *The Prostate* 22:335–345 (1993).

Phillips and Castle, "Quino[1,2–c]quinazolines. I. Synthesis of Quino[1,2–c]quinazolinium Derivatives and the Related Indazolo[2,3–a]quinoline Derivatives as Analogs of the Antitumor Benzo[c]phenanthridine Alkaloids," *J. Heterocyclic Chemistry* 17:1489–1496 (1980).

Pillemer et al., "Insulin Dependence of Murine Lymphoid T–Cell Leukemia," *Brit. J. Cancer* 50:80–85 (1992).

Posner et al., "Kinetics of inhibition by Tyrphostins of the Tyrosine Kinase Activity of the Epidermal Growth Factor Receptor and Analysis by a New Computer Program," *Molecular Pharmacology* 45:673–683 (1993).

Pursel et al., "Genetic Engineering of Livestock," *Science* 244:1281–1288 (1989).

Redemann et al., "Anti–Oncogenic Activity of Signalling––Defective Epidermal Growth Factor Receptor Mutants," *Molecular and Cellular Biology* 12(2):491–498 (1992).

Reece et al., "Pharmacokinetics of Trimetrexate Administered by Five–Day Continuous Infusion to Patients with Advanced Cancer," *Cancer Research* 47:2996–2999 (1987).

Rendu et al., "Inhibition of Platelet Activation by Tyrosine Kinase Inhibitors," *Biochemical Pharmacology* 44(5):881–888 (1992).

Reznikoff et al., "A Molecular Genetic Model of Human Bladder Cancer Pathogenesis," *Seminars in Oncology* 23:571–584 (1996).

Robertson, E.J., ed., Teratocarcinomas and Embryonic Stem Cells, A Practical Appraoch, IRL Press (1987).

Roghi et al., "*Xenopus laevis* mRNA encoding protein kinase," *EMBL Sequence Database,* Heidelberg, Brd., XP002029130, accession No. Z17206, Jan. 1, 1995.

Roghi et al., "*Xenopus laevis* mRNA encoding protein kinase," *EMBL Sequence Database,* Heidelberg, Brd., XP002029131, accession No. Z17207, Jan. 1, 1995.

Rubin, "*Drosophila melanogaster* as an Experimental Organism," *Science* 240:1453–1459 (1988).

Sambrook, Fritsch & Maniatis, eds., *Molecular Cloning: A Laboratory Manual,* second edition, Cold Spring Harbor Laboratory (1989).

Sauro and Thomas, "Decreased Sensitivity of Aorta from Hypertensive Rats to Vasorelaxation by Tyrphostin," *Life Sciences* 53:PL371–376 (1993).

Sauro and Thomas, "Tyrphostin Attenuates Platelet–Derived Growth Factor–Induced Contraction in Aortic Smooth Muscle Through Inhibition of Protein Tyrosine Kinase(s)," *The Journal of Pharmacology and Experimental Therapeutics* 267:1119–1125 (1993).

Savelieva et al., "20q gain associates with immortalization: 20q13.2 amplification correlates with genome instability in human papillomavirus 16 E7 transformed human uroepithelial cells," *Oncogene* 14:551–560 (1997).

Schlegel et al., "Comparative Genomic in Situ Hybridization of Colon Carcinomas with Replication Error," *Cancer Research* 55:6002–6005 (1995).

Sculier et al., "Role of an Intensive Care Unit (ICU) in a Medical Oncology Department," *Cancer Immunol. and Immunotherapy* 23:A65 at abstract No. 257 (1986).

Sen et al., "A putative serine/threonine kinase encoding gene BTAK on chromosome 20q13 is amplified and overexpressed in human breast cancer cell lines," *Oncogene* 14:2195–2200 (1997).

Sherr, "Cancer Cell Cycles," *Science* 274:1672–1677 (1996).

Sikora and Grzelakowska–Sztabert, "Quinazoline CB 3717 and CB 3703 Inhibitors of Folate Retention and Metabolism in Ehrlich Ascites Carcinoma Cells and Some Organs of the Host–Mouse," *Cancer Letters* 23:289–295 (1984).

Sikora et al., "Development of an Assay for the Estimation of $N^{10}$–Propargyl–5,8–dideazafolic Acid Polyglutamates in Tumor Cells," *Analytical Biochemistry* 172:344–355 (1988).

Silver et al., "Amino terminus of the yeast GAL4 gene product is sufficient for nuclear localization," *Proc. Natl. Acad. Sci. USA* 81:5951–5955 (1984).

Simons et al., "Gene Transfer into Sheep," *Bio/Technology* 6:179–182 (1988) (also referred to as Simms or Simmons).

Solinas–Toldo et al., "Mapping of Chromosomal Imbalances in Pancreatic Carcinoma by Comparative Genomic Hybridization," *Cancer Research* 56:3803–3807 (1996).

Southern, "Detection of Specific Sequences Among DNA Fragments Separated byGel Electrophoresis," *J. Mol. Biol.* 98:503–517 (1975).

St. Groth and Scheidegger, "Production of Monoclonal Antibodies: Strategy and Tactics," *J. Immunol. Methods* 35:1–21 (1980).

Sternberger et al., "The Unlabeled Antibody Enzyme Method of Immunohistochemistry: Preparation and Properties of Soluble Antigen–Antibody Complex (Horseradish Peroxidase–Antihorseradish Peroxidase) and Its Use in Identification of Spirochetes," *J. Histochemistry and Cytochemistry* 18(5):315–333 (1970) (mistakenly referred to as Stemberger).

Tabor et al., "DNA sequence analysis with a modified bacteriophage T7 DNA polymerase," *Proc. Natl. Acad. Sci. USA* 84:4767–4771 (1987).

Tanner et al., "Increased Copy Number at 20q13 in Breast Cancer: Defining the Critical Region and Exclusion of Candidate Genes," *Cancer Research* 54:4257–4260 (1994).

Tanner et al., "Independent Amplification and Frequent Co–Amplification of Three Nonsyntenic Regions on the Long Arm of Chromosome 20 in Human Breast Cancer," *Cancer Research* 56:3441–3445 (1996).

Tijssen, "Practice and Theory of Enzyme Immunoassays: Laboratory Techniques in Biochemistry and Molecular Biology," Elsevier Science Publishers, Amsterdam, The Netherlands (1985).

Tirkkonen et al., "Distinct Somatic Genetic Changes Associated with Tumor Progression in Carriers of BRCA1 and BRCA2 Germ–line Mutations," *Cancer Research* 57:1222–1227 (1997).

Ulmanen et al., "Transcription and Translation of Foreign Genes in *Bacillus subtilis* by the Aid of a Secretion Vector," *Journal of Bacteriology* 162:176–182 (1985).

Ward et al., "Construction and characterisation of a series of multi–copy promoter–probe plasmid vectors for Streptomyces using the aminoglycoside phosphotransferase gene from Tn5 as indicator," *Mol. Gen. Genet.* 203:468–478 (1986).

Weir (eds), "Ch. 10—The chemistry and standardization of allergens," in *Handbook of Experimental Immunology—Volume 1: Immunochemistry*, 4th Ed., edited by Weir et al., Blackwell Scientific Publications, Oxford, England, pp. 10.1–10.28 (1986).

Wolbring et al., "Inhibition of GTP–utilizing Enzymes by Tyrphostins," *J. Biol. Chem.* 269:22470–22472 (1994).

Wolf et al., "Prognostic significance of polo–like kinase (PLK) expression in non–small cell lung cancer," *Oncogene* 14:543–549 (1997).

Yanai et al., "ayk1, a novel mammalian gene related to *Drosophila aurora* centrosome separation kinase, is specifically expressed during meiosis," *Oncogene* 14:2943–2950 (1997).

Yang et al., "In Vivo and In Vitro Gene Transfer to Mammalian Somatic Cells by Particle Bombardment," *Proc. Natl. Acad. Sci. USA* 87:9568–9572 (1990).

Yaseen et al., "Chromosome Studies in Eleven Colorectal Tumors," *Cancer Genet Cytogenet* 44:83–97 (1990).

Yoneda et al., "The Antiproliferative Effects of Tyrosine Kinase Inhibitors Tyrphostins on a Human Squamous Cell Carcinoma in Vitro and in Nude Mice," *Cancer Research* 51:4430–4435 (1991).

Tung et al., Molecular and cellular Biology, 15(11), 6064–6074, Nov. 1995.*

Kimura et al., "Molecular cloning of a human homolog of Aurora, a serine/threonine kinase which regulates the chromosome segregation," Nippon Bunshi Seibutsu Gakkai Nenkai Puroguramu, vol. 18, pp. 497, Abst. 3P–205 (1995).

* cited by examiner

FIG. 1

```
AUR1_h    MAQ-------KENSYPWP------------YGRQTAPS  19
AUR2_h    MDRS------KENCISGPVKATAPVG-GPKRVLVTQQFPCQNPLP  38
AUR_dm    MSHPSDHVLRPKENAPHRMPEKSAAVLNMQKNLLLGKKPNSENMAP  46
1PLI_sc   MQRNSLVNI--KLNANSPS------------KTTTRPNTSRINKPW  33

AUR1_h    GL----------------------------STLPQRVL  29
AUR2_h    VN----------------------------SGQAQRVL  48
AUR_dm    DSKPLPGSSGALIRSAATTVRPATKPGLGGSNSIASSEGNNFQKPM  92
1PLI_sc   RI----------------------------SHSPQQRNP  44

AUR1_h    RKEPVTPSALVLMSRSNVQPTAAPGQK-VMENSSGTPDILT-----  69
AUR2_h    CPSNSSQRVPLQAQKLVSSHKPVQNQKQLQATSVPHPVSRPLNN  94
AUR_dm    VPSVKKTTSEFAAPAPVAPIKKPESLS-KQ----------KPTAA 126
1PLI_sc   NSKIPSPVREKLNRLPVNNKKFLDME-------------------  70

AUR1_h    --------------------------RHFTIDDFEIG  80
AUR2_h    TQKSKQPLPSAPENNPEFELASKQKN----EESKKRQWALEDFEIG 136
AUR_dm    SSESSKELGAASSSAEKEKTKTETQ---PQKP--KKTWELNNFDIG 167
1PLI_sc   ---SSKIP-----SPIRKATSSKMIHENKKLPKFKSLSLDDFFLG 107

AUR1_h    RPLGKGKFGNVYLAREKKSHFIVALKVLFKSQIEKEGVEHQLRREI 126
AUR2_h    RPLGKGKFGNVYLAREKQSKFILALKVLFKAQLEKAGVEHQLRREV 182
AUR_dm    RLLGRGKFGNVYLAREKESQFVVALLVLFKRQIGESNVEHQVRREI 213
1PLI_sc   KKLGKGKFGKVYCVRHRSTGYICALKVMEKEEIIKYNLQKQFRREV 153

AUR1_h    EIQAHLHHPNILRLYNYFYDRRRLYLILEYAPRGELYKEL--QKSC 170
AUR2_h    EIQSHLRHPNILRLYGYFHDATRVYLILEYAPLGTVVREL--QKLS 226
AUR_dm    EIQSHLRHPHILRLYAYFHDDVRTYLILEYAPQGTLFNALQAQPMK 259
1PLI_sc   EIQTSLNHPNLTKSLYGYFHDEKRVYLMFEYLVNGEMYKLL--RLHG 197

AUR1_h    TFDEQRTATIMEELADAMYCHGKKVIHRDIKPENLLLGLKGELKI 216
AUR2_h    KFDEQRTATYITELANALSYCHSKRVIHRDIKPENLLLGSAGELKI 272
AUR_dm    RFDERQSATYIQALCSALLYLHERDIIHRDIKPENLLLGHKGVLKI 305
1PLI_sc   PFNDILASDIYQIANALDYMHKKNIIHRDIKPENTLLGFNNVIKL 243

AUR1_h    ADFGWSV-HAPSLRRKTMCGTLDYLPPEMIEGRMHNEKVDLWCIGV 261
AUR2_h    ADFGWSV-HAPSSRRTTLCGTLDYLPPEMIEGRMHDEKVDLWSLGV 317
AUR_dm    ADFGWSV-HEPNSMRMTLCGTVDYLPPEMVQGKPHTKNVDLWSLGV 350
1PLI_sc   TDFGWSTINPPENRRKTMCGTIDYLSPEMVESREYDHTIDAWALGV 289

AUR1_h    LCYELLVGNPPFESASHNETYRRIVKVDLKFPASVPTGAQDLISKL 307
AUR2_h    LCYEFLVGKPPFEANTYQETYKRISRVEFTEPDFVTEGARDLISRL 363
AUR_dm    LCFELLVGHAPFYSKNYDETYKILKVDYKLPEHISKASHLISKL 396
1PLI_sc   LAFELLTGAPPFEEMKDTIYKRIAALDIKMPSNISQDAQDLINKL 335

AUR1_h    LRHNPSERLPLAQVSAHPWVRANSRRVLPPSALQSVA         344
AUR2_h    LKHNPSQRPMLREVLEHPWITANSSK--PSNCQNKESASKQS    403
AUR_dm    LVLNPQHRLPLDQVMVHPWILAHTQ                     421
1PLI_sc   LKYDPKDRMRLGDVKMHPWILRNKPFWENKRL              367
```

DIAGNOSIS AND TREATMENT OF AUR-1 AND/OR AUR-2 RELATED DISORDERS

RELATED APPLICATIONS

This application is a divisional of U.S. patent application Ser. No. 09/012,135, filed Jan. 22, 1998, by Plowman et al., and entitled "AUR1 and/or AUR2 Related Disorders" which is a continuation-in-part of U.S. patent application Ser. No. 09/005,268, filed Jan. 9, 1998, by Plowman et al., and entitled "AUR1 and/or AUR2 Related Disorders" now abondoned, which is a continuation-in-part of U.S. patent application Ser. No. 08/755,728, filed Nov. 25, 1996, by Plowman, et al., and entitled "Diagnosis and Treatment of AUR1 and/or AUR2 Related Disorders" now U.S. Pat. No. 5,962,312 issued on Nov. 5, 1999, and claims priority to U.S. patent application Ser. No. 60/008,809 filed Dec. 18, 1995, and U.S. patent application Ser. No. 60/023,943, filed Aug. 14, 1996, all of which are incorporated herein by reference in their entirety, including any drawings.

FIELD OF THE INVENTION

The present invention relates to the novel proteins termed AURORA ONE and AURORA TWO ("AUR1 and AUR2"), nucleotide sequences encoding AUR1 and/or AUR2, as well as various products and methods useful for the diagnosis and treatment of various AUR1 and/or AUR2 related diseases and conditions.

BACKGROUND OF THE INVENTION

The following description of the background of the invention is provided to aid in understanding the invention but is not admitted to be prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of proteins, which enables regulation of the activity of mature proteins by altering their structure and function.

The best characterized protein kinases in eukaryotes phosphorylate proteins on the alcohol moiety of serine, threonine and tyrosine residues. These kinases largely fall into two groups, those specific for phosphorylating serines and threonines, and those specific for phosphorylating tyrosines. Some kinases, referred to as "dual specificity" kinases, are able to phosphorylate on tyrosine as well as serine/threonine residues.

Protein kinases can also be characterized by their location within the cell. Some kinases are transmembrane receptor-type proteins capable of directly altering their catalytic activity in response to the external environment such as the binding of a ligand. Others are non-receptor-type proteins lacking any transmembrane domain. They can be found in a variety of cellular compartments from the inner surface of the cell membrane to the nucleus.

Many kinases are involved in regulatory cascades wherein their substrates may include other kinases whose activities are regulated by their phosphorylation state. Ultimately the activity of some downstream effector is modulated by phosphorylation resulting from activation of such a pathway.

The serine/threonine kinase family includes members found at all steps of various signaling cascades, including those involved in controlling cell growth, migration, differentiation and secretion of hormones, phosphorylation of transcription factors resulting in altered gene expression, muscle contraction, glucose metabolism, control of cellular protein synthesis, and regulation of the cell cycle.

Chromosomal abnormalities are a hallmark of human cancer, reflecting the deleterious consequences of the gain or loss of genetic information (Mitelman et al., Nature Genet. 15:417–474, 1997; Hartwell et al., Science 266:1821–1828, 1994). Some of these defects may have a causal role in cellular transformation due to loss of a negative growth regulator, loss of a gene responsible for maintenance of genome integrity, or through the amplification or activation of an oncogene (Kinzler et al., Nature 386:761–763, 1997; Hunter Cell 88:333–346, 1997). Alternatively, these abnormalities may be a consequence of tumor progression where mitotic checkpoints have been disrupted, resulting in abnormal nuclei, miss-segregated chromosomes, and aneuploidy (Elledge Science 274:1664–1672, 1996; Sherr Science 274:1672–1677, 1996).

SUMMARY OF THE INVENTION

The present invention relates in part to AUR1 and/or AUR2 polypeptides, nucleic acids encoding such polypeptides, cells, tissues and animals containing such nucleic acids, antibodies to such polypeptides, assays utilizing such polypeptides, and methods relating to all of the foregoing. The utility of the present invention includes the ability to screen for inhibitors of cell growth and to develop small molecule therapeutics for treating cancers.

Thus, in a first aspect, the invention features an isolated, enriched, or purified nucleic acid encoding an AUR1 and/or AUR2 polypeptide.

By "isolated" in reference to nucleic acid is meant a polymer of 6 (preferably 21, more preferably 39, most preferably 75) or more nucleotides conjugated to each other, including DNA and RNA that is isolated from a natural source or that is synthesized. In certain embodiments of the invention, longer nucleic acids are preferred, for example those of 300, 600, 900 or more nucleotides and/or those having at least 50%, 60%, 75%, 90%, 95% or 99% identity to the fall length sequence shown in SEQ ID NO:1 or SEQ ID NO:2. The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide chain present, but that it is essentially free (about 90–95% pure at least) of non-nucleotide material naturally associated with it, and thus is distinguished from isolated chromosomes.

By the use of the term "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased. The term significant here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation). Instead, it represents an indication that the sequence is relatively more pure than in the natural environment (compared to the natural level this level should be at least 2–5 fold greater, e.g., in terms of mg/mL). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated.

By "an AUR1 and/or AUR2 polypeptide" is meant 25 (preferably 30, more preferably 35, most preferably 40) or more contiguous amino acids set forth in the full length amino acid sequence of SEQ ID NO:3 or SEQ ID NO:4, or a functional derivative thereof as described herein. In certain aspects, polypeptides of 100, 200, 300 or more amino acids are preferred. The AUR1 and/or AUR2 polypeptide can be encoded by a full-length nucleic acid sequence or any portion of the full-length nucleic acid sequence, so long as a functional activity of the polypeptide is retained.

Also included are inactive and activated mutants of AUR1 and/or AUR2, including, but not limited to those defined in Example 11 herein. By "inactive" is meant an AUR1 and/or AUR2 polypeptide which lacks kinase activity. In some embodiments, the essential lysine (residue 162) is mutated. Preferably the polypeptide is otherwise unchanged. By "activated" is meant an AUR1 and/or AUR2 polypeptide which has kinase activity in vitro, preferably in situations where the unmutated polypeptide does not. Preferably, the AUR1 and/or AUR2 polypeptide is mutated to mimic constitutive phosphorylation. In some embodiments, the threonine at residue 288 in the activation loop is modified to an aspartic acid.

The amino acid sequence will be substantially similar to the sequence shown in SEQ ID NO:3 or SEQ ID NO:4, or fragments thereof. A sequence that is substantially similar will preferably have at least 90% identity (more preferably at least 95% and most preferably 99–100%) to the sequence of SEQ ID NO:3 or SEQ ID NO:4.

By "identity" is meant a property of sequences that measures their similarity or relationship. Identity is measured by dividing the number of identical residues by the total number of residues and multiplying the product by 100. Thus, two copies of exactly the same sequence have 100% identity, but sequences that are less highly conserved, and have deletions, additions, or replacements, may have a lower degree of identity. Those skilled in the art will recognize that several computer programs are available for determining sequence identity.

In a preferred embodiment, the invention features a nucleic acid molecule comprising a nucleotide sequence that: (a) encodes a polypeptide having the full length amino acid sequence set forth in SEQ ID NO:3 or SEQ ID NO:4; (b) is the complement of the nucleotide sequence of (a); (c) hybridizes under highly stringent conditions to the nucleic acid molecule of (a) and encodes a naturally occurring AUR1 and/or AUR2 polypeptide; (d) encodes AUR1 and/or AUR2 polypeptide having the full length amino acid sequence set forth in SEQ ID NO:3 or SEQ ID NO:4 except that it lacks one or more of the following segments of amino acid residues: 1–73, 74–271, or 272–344 of SEQ ID NO:3, or 1–129, 130–274, or 275–403 of SEQ ID NO:4; (e) is the complement of the nucleotide sequence of (d); (f) encodes a polypeptide having the amino acid sequence set forth in SEQ ID NO:3 or SEQ ID NO:4 from amino acid residues 1–73, 74–271, or 272–344 of SEQ ID NO:3, or 1–129, 130–274, 275–403 of SEQ ID NO:4; (g) is the complement of the nucleotide sequence of (f); (h) encodes a polypeptide having the full length amino acid sequence set forth in SEQ ID NO:3 or SEQ ID NO:4 except that it lacks one or more of the domains selected from the group consisting of a C-terminal domain, a catalytic domain, and an N-terminal domain; or (i) is the complement of the nucleotide sequence of (h).

The term "complement" refers to two nucleotides that can form multiple favorable interactions with one another. For example, adenine is complementary to thymine as they can form two hydrogen bonds. Similarly, guanine and cytosine are complementary since they can form three hydrogen bonds. A nucleotide sequence is the complement of another nucleotide sequence if all of the nucleotides of the first sequence are complementary to all of the nucleotides of the second sequence.

The term "domain" refers to a region of a polypeptide which contains a particular function. For instance, N-terminal or C-terminal domains of signal transduction proteins can serve functions including, but not limited to, binding molecules that localize the signal transduction molecule to different regions of the cell or binding other signaling molecules directly responsible for propagating a particular cellular signal. Some domains can be expressed separately from the rest of the protein and function by themselves, while others must remain part of the intact protein to retain function. The latter are termed functional regions of proteins and also relate to domains.

The term "N-terminal domain" refers to a portion of the full length amino acid sequence spanning from the amino terminus to the start of the catalytic domain. The N-terminal domain spans amino acid residues 1–73 of the sequence set forth in SEQ ID NO:3 or amino acids 1–130 of the sequence set forth in SEQ ID NO:4.

The term "catalytic domain" refers to a portion of the full length amino acid sequence that does not contain the N-terminal domain or the C-terminal domain and has catalytic activity. The catalytic domain spans amino acid residues 73–271 of the sequence set forth in SEQ ID NO:3 or residues 130–274 of the sequence set forth in SEQ ID NO:4.

The term "C-terminal domain" refers to a portion of the full length amino acid sequence that begins at the end of the catalytic domain and ends at the carboxyl terminal amino acid, which is the last amino acid encoded before the stop codon in the nucleic acid sequence. The C-terminal domain spans amino acid residues 272–344 of the sequence set forth in SEQ ID NO:3 or amino acids 275–403 of the sequence set forth in SEQ ID NO:4.

In preferred embodiments, the isolated nucleic acid comprises, consists essentially of, or consists of a nucleic acid sequence set forth in SEQ ID NO:1 or SEQ ID NO:2, encodes the full length amino acid sequence of SEQ ID NO:3 or SEQ ID NO:4, a functional derivative thereof, or at least 25, 30, 35, 40, 50, 100, 200, or 300 contiguous amino acids thereof. The AUR1 and/or AUR2 polypeptide comprises, consists essentially of, or consists of at least 25, 30, 35, or 40 contiguous amino acids of an AUR1 and/or AUR2 polypeptide. The nucleic acid may be isolated from a natural source by cDNA cloning or by subtractive hybridization. The natural source may be mammalian, preferably human, blood, semen, or tissue and the nucleic acid may be synthesized by the triester method or by using an automated DNA synthesizer.

In yet other preferred embodiments, the nucleic acid is a conserved or unique region, for example those useful for: the design of hybridization probes to facilitate identification and cloning of additional polypeptides, the design of PCR probes to facilitate cloning of additional polypeptides, obtaining antibodies to polypeptide regions, and designing antisense oligonucleotides. Examples of amino acid sequences of the present invention include the following amino acid sequences (the isolated, purified or enriched nucleic acids encoding them are also within the scope of the present invention): ENSYPWPYGRQ (SEQ ID NO:5), CISGP (SEQ ID NO:6), QFPQ (SEQ ID NO:7), VNSGQ (SEQ ID NO:8), RKEPVTPSA-LV (SEQ ID NO:9), LMSRSNVQPTAAP (SEQ ID NO:10), VQN-QKQKQLQATSVPH (SEQ ID NO:11), PVSRPLNNTQK (SEQ ID NO:12), VMENSSGTPD (SEQ ID NO:13), ILTRHFTID (SEQ ID NO:14), and SKQPLPSAPENNPE-EQLASKQK (SEQ ID NO:15).

By "conserved nucleic acid regions", are meant regions present on two or more nucleic acids encoding an AUR1 and/or AUR2 polypeptide, to which a particular nucleic acid sequence can hybridize under lower stringency conditions. Examples of lower stringency conditions suitable for screening for nucleic acid encoding AUR1 and/or AUR2 polypeptides are provided in Abe et al. J. Biol. Chem. 19:13361–13368, 1992 (hereby incorporated by reference herein in its entirety, including any drawings). Preferably, conserved regions differ by no more than 5 out of 20 nucleotides.

By "unique nucleic acid region" is meant a sequence present in a full length nucleic acid coding for an AUR1 and/or AUR2 polypeptide that is not present in a sequence coding for any other naturally occurring polypeptide. Such regions preferably comprise 30 to 45 contiguous nucleotides present in the full length nucleic acid encoding an AUR1 and/or AUR2 polypeptide. In particular, a unique nucleic acid region is preferably of mammalian origin.

In a preferred embodiment, the isolated, enriched or purified nucleic acid molecule encoding AUR1 and/or AUR2 polypeptide, comprises a vector or promoter effective to initiate transcription in a host cell.

The invention also features a nucleic acid probe for the detection of nucleic acid encoding an AUR1 and/or AUR2 polypeptide in a sample. The nucleic acid probe contains a nucleotide base sequence that will hybridize to a sequence set forth in SEQ ID NO:1 or SEQ ID NO:2 or a functional derivative thereof.

In preferred embodiments the nucleic acid probe hybridizes to nucleic acid encoding at least 12, 75, 90, 105, 120, 150, 200, 250, 300 or 350 contiguous amino acids of the full-length sequence set forth in SEQ ID NO:3 or SEQ ID NO:4 or a functional derivative thereof. Various low or high stringency hybridization conditions may be used depending upon the specificity and selectivity desired. Under stringent hybridization conditions only highly complementary nucleic acid sequences hybridize. Preferably, such conditions prevent hybridization of nucleic acids having 1 or 2 mismatches out of 20 contiguous nucleotides.

By stringent hybridization assay conditions is meant hybridization assay conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart solution at 42° C. overnight; washing with 2×SSC, 0.1% SDS at 45° C.; and washing with 0.2×SSC, 0.1% SDS at 45° C.

Methods for using the probes include detecting the presence or amount of AUR1 and/or AUR2 RNA in a sample by contacting the sample with a nucleic acid probe under conditions such that hybridization occurs and detecting the presence or amount of the probe bound to AUR1 and/or AUR2 RNA. The nucleic acid duplex formed between the probe and a nucleic acid sequence coding for an AUR1 and/or AUR2 polypeptide may be used in the identification of the sequence of the nucleic acid detected (Nelson et al., in Nonisotopic DNA Probe Techniques, Academic Press, San Diego, Kricka, ed., p. 275, 1992, hereby incorporated by reference herein in its entirety, including any drawings). Kits for performing such methods may be constructed to include a container means having disposed therein a nucleic acid probe.

The invention also features recombinant nucleic acid, preferably in a cell or an organism. The recombinant nucleic acid may contain a sequence set forth in SEQ ID NO:1 or SEQ ID NO:2 or a functional derivative thereof and a vector or a promoter effective to initiate transcription in a host cell. The recombinant nucleic acid can alternatively contain a transcriptional initiation region functional in a cell, a sequence complementary to an RNA sequence encoding an AUR1 and/or AUR2 polypeptide and a transcriptional termination region functional in a cell.

In another aspect, the invention describes a recombinant cell or tissue containing nucleic acid coding for an AUR1 and/or AUR2 polypeptide. In such cells, the nucleic acid may be under the control of its genomic regulatory elements, or may be under the control of exogenous regulatory elements including an exogenous promoter. By "exogenous" it is meant a promoter that is not normally coupled in vivo transcriptionally to the coding sequence for the AUR1 and/or AUR2 polypeptide.

The polypeptide is preferably a fragment of the protein encoded by the full length amino acid sequence set forth in SEQ ID NO:3 or SEQ ID NO:4. By "fragment," is meant an amino acid sequence present in a full-length AUR1 and/or AUR2 polypeptide that is not present in any other naturally occurring polypeptide. Preferably, such a sequence comprises 6 contiguous amino acids present in the full sequence. More preferably, such a sequence comprises 12 contiguous amino acids present in the full sequence. Even more preferably, such a sequence comprises 18 contiguous amino acids present in the full sequence.

In another aspect the invention features an isolated, enriched, or purified AUR1 and/or AUR2 polypeptide.

By "isolated" in reference to a polypeptide is meant a polymer of 2 (preferably 7, more preferably 13, most preferably 25) or more amino acids conjugated to each other, including polypeptides that are isolated from a natural source or that are synthesized. In certain aspects longer polypeptides are preferred, such as those with 402, 407, 413, or 425 contiguous amino acids set forth in SEQ ID NO:3 or SEQ ID NO:4. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of non-amino acid material naturally associated with it.

By the use of the term "enriched" in reference to a polypeptide is meant that the specific amino acid sequence constitutes a significantly higher fraction (2–5 fold) of the total amino acids present in the cells or solution of interest than in normal or diseased cells or in the cells from which the sequence was taken. This could be caused by a person by preferential reduction in the amount of other amino acids present, or by a preferential increase in the amount of the specific amino acid sequence of interest, or by a combination of the two. However, it should be noted that enriched does not imply that there are no other amino acid sequences present, just that the relative amount of the sequence of interest has been significantly increased. The term significant here is used to indicate that the level of increase is useful to the person making such an increase, and generally means an increase relative to other amino acids of about at least 2 fold, more preferably at least 5 to 10 fold or even more. The term also does not imply that there is no amino acid from other sources. The other source amino acid may, for example, comprise amino acid encoded by a yeast or bacterial genome, or a cloning vector such as pUC19. The term is meant to cover only those situations in which man has intervened to elevate the proportion of the desired amino acid.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment. Compared to the natural level this level should be at least 2–5 fold greater (e.g., in terms of mg/mL). Purification of at least one order of magnitude, preferably two or three orders, and more preferably four or five orders of magnitude is expressly contemplated. The substance is preferably free of contamination at a functionally significant level, for example 90%, 95%, or 99% pure.

In preferred embodiments, the AUR1 and/or AUR2 polypeptide contains at least 25, 30, 35, 40, 50, 100, 150, 200, 250, 300, or 350 contiguous amino acids of the full-length sequence set forth in SEQ ID NO:3 or SEQ ID NO:4, or a functional derivative thereof.

Also included are inactive and activated mutants of AUR1 and/or AUR2, including, but not limited to those defined in Example 11 herein. By "inactive" is meant an AUR1 and/or AUR2 polypeptide which lacks kinase activity. In some embodiments, the essential lysine (residue 162) is mutated. Preferably the polypeptide is otherwise unchanged. By "activated" is meant an AUR1 and/or AUR2 polypeptide which has kinase activity in vitro, preferably in situations where the unmutated polypeptide does not. Preferably, the AUR1 and/or AUR2 polypeptide is mutated to mimic constitutive phosphorylation. In some embodiments, the threonine at residue 288 in the activation loop is modified to an aspartic acid.

The polypeptide may be isolated from a natural source by methods well-known in the art. The natural source may be mammalian, preferably human, blood, semen, or tissue, and the polypeptide may be synthesized using an automated polypeptide synthesizer.

In a preferred embodiment, the invention features a polypeptide comprising an amino acid sequence having (a) the full length amino acid sequence set forth in SEQ ID NO:3 or SEQ ID NO:4; (b) the full length amino acid sequence set forth in SEQ ID NO:3 or SEQ ID NO:4 except that it lacks one or more of the following segments of amino acid residues: 1–73, 74–271, or 272–344 of SEQ ID NO:3, or 1–129, 130–274, or 275–403 of SEQ ID NO:4; (c) the amino acid sequence set forth in SEQ ID NO:3 or SEQ ID NO:4 from amino acid residues 1–73, 74–271, or 272–344 of SEQ ID NO:3, or 1–129, 130–274, or 275–403 of SEQ ID NO:4; or (d) the full length amino acid sequence set forth in SEQ ID NO:3 or SEQ ID NO:4 except that it lacks one or more of the domains selected from the group consisting of a C-terminal domain, a catalytic domain, and an N-terminal domain.

In some embodiments the invention includes a recombinant AUR1 and/or AUR2 polypeptide. By "recombinant AUR1 and/or AUR2 polypeptide" is meant a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

In yet another aspect, the invention features an antibody (e.g., a monoclonal or polyclonal antibody) having specific binding affinity to an AUR1 and/or AUR2 polypeptide or an AUR1 and/or AUR2 polypeptide domain or fragment. By "specific binding affinity" is meant that the antibody binds to the target (AUR1 and/or AUR2) polypeptide with greater affinity than it binds to other polypeptides under specified conditions. Antibodies or antibody fragments are polypeptides which contain regions that can bind other polypeptides. The term "specific binding affinity" describes an antibody that binds to an AUR1 and/or AUR2 polypeptide with greater affinity than it binds to other polypeptides under specified conditions.

The term "polyclonal" refers to antibodies that are heterogeneous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art (Kohler et al., Nature 256:495–497, 1975, and U.S. Pat. No. 4,376,110).

The term "antibody fragment" refers to a portion of an antibody, often the hyper variable region and portions of the surrounding heavy and light chains, that displays specific binding affinity for a particular molecule. A hyper variable region is a portion of an antibody that physically binds to the polypeptide target.

Antibodies or antibody fragments having specific binding affinity to an AUR1 and/or AUR2 polypeptide may be used in methods for detecting the presence and/or amount of AUR1 and/or AUR2 polypeptide in a sample by probing the sample with the antibody under conditions suitable for AUR1 and/or AUR2-antibody immunocomplex formation and detecting the presence and/or amount of the antibody conjugated to the AUR1 and/or AUR2 polypeptide. Diagnostic kits for performing such methods may be constructed to include antibodies or antibody fragments specific for AUR1 and/or AUR2 as well as a conjugate of a binding partner of the antibodies or the antibodies themselves.

An antibody or antibody fragment with specific binding affinity to an AUR1 and/or AUR2 polypeptide can be isolated, enriched, or purified from a prokaryotic or eukaryotic organism. Routine methods known to those skilled in the art enable production of antibodies or antibody fragments, in both prokaryotic and eukaryotic organisms. Purification, enrichment, and isolation of antibodies, which are polypeptide molecules, are described above.

Antibodies having specific binding affinity to an AUR1 and/or AUR2 polypeptide may be used in methods for detecting the presence and/or amount of AUR1 and/or AUR2 polypeptide in a sample by contacting the sample with the antibody under conditions such that an immunocomplex forms and detecting the presence and/or amount of the antibody conjugated to the AUR1 and/or AUR2 polypeptide. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

In another aspect, the invention features a hybridoma which produces an antibody having specific binding affinity to an AUR1 and/or AUR2 polypeptide or an AUR1 and/or AUR2 polypeptide domain. By "hybridoma" is meant an immortalized cell line which is capable of secreting an antibody, for example an antibody to AUR1 and/or AUR2. In preferred embodiments the antibody to AUR1 and/or AUR2 comprises a sequence of amino acids that is able to specifically bind an AUR1 and/or AUR2 polypeptide.

In another aspect, the invention features an AUR1 and/or AUR2 polypeptide binding agent able to bind to an AUR1 and/or AUR2 polypeptide. The binding agent is preferably a purified antibody which recognizes an epitope present on an AUR1 and/or AUR2 polypeptide. Other binding agents include molecules which bind to the AUR1 and/or AUR2 polypeptide and analogous molecules which bind to an AUR1 and/or AUR2 polypeptide. Such binding agents may be identified by using assays that measure AUR1 and/or AUR2 binding partner activity, such as those that measure PDGFR activity.

The invention features a method for screening for human cells containing an AUR1 and/or AUR2 polypeptide or an equivalent sequence. The method involves identifying the novel polypeptide in human cells using techniques that are routine and standard in the art, such as those described herein for identifying AUR1 and/or AUR2 (e.g., cloning, Southern or Northern blot analysis, in situ hybridization, PCR amplification, etc.).

In another aspect, the invention provides a method for identifying a substance capable of modulating AUR1 and/or AUR2 activity comprising the steps of (a) contacting AUR1 and/or AUR2 polypeptide with a test substance; (b) measuring the activity of said polypeptide; and (c) determining whether said substance modulates the activity of said polypeptide.

The term "modulates" refers to the ability of a compound to alter the function of AUR1 and/or AUR2. A modulator preferably activates or inhibits the activity of AUR1 and/or AUR2 depending on the concentration of the compound exposed to AUR1 and/or AUR2.

The term "activates" refers to increasing the cellular activity of AUR1 and/or AUR2. The term "inhibit" refers to decreasing the cellular activity of AUR1 and/or AUR2. AUR1 and/or AUR2 activity is preferably the interaction with a natural binding partner.

The term "modulates" also refers to altering the function of AUR1 and/or AUR2 by increasing or decreasing the probability that a complex forms between AUR1 and/or AUR2 and a natural binding partner. A modulator preferably increases the probability that such a complex forms between AUR1 and/or AUR2 and the natural binding partner, more preferably increases or decreases the probability that a complex forms between AUR1 and/or AUR2 and the natural binding partner depending on the concentration of the compound exposed to AUR1 and/or AUR2, and most preferably decreases the probability that a complex forms between AUR1 and/or AUR2 and the natural binding partner.

The term "complex" refers to an assembly of at least two molecules bound to one another. Signal transduction complexes often contain at least two protein molecules bound to one another. For instance, a protein tyrosine receptor protein kinase, GRB2, SOS, RAF, and RAS assemble to form a signal transduction complex in response to a mitogenic ligand.

The term "natural binding partner" refers to polypeptides or nucleic acids that bind to AUR1 and/or AUR2 in cells. A change in the interaction between AUR1 and/or AUR2 and a natural binding partner can manifest itself as an increased or decreased probability that the interaction forms, or an increased or decreased concentration of AUR1 and/or AUR2/natural binding partner complex.

The term "contacting" as used herein refers to mixing a solution comprising the test compound with a liquid medium bathing the cells of the methods. The solution comprising the compound may also comprise another component, such as dimethyl sulfoxide (DMSO), which facilitates the uptake of the test compound or compounds into the cells of the methods. The solution comprising the test compound may be added to the medium bathing the cells by utilizing a delivery apparatus, such as a pipet-based device or syringe-based device.

In another aspect, the invention provides for the treatment of diseases by administering to a patient in need of such treatment a substance that modulates the activity of AUR1 and/or AUR2. Such substances preferably show positive results in one or more in vitro assays for an activity corresponding to treatment of the disease or disorder in question (such as the assays described in example 13 below). Examples of substances that can be screened for favorable activity are provided in section XI below. The diseases that could be treated by a modulator of AUR1 and/or AUR2 activity preferably include colon, breast, renal, ovarian, bladder, head and neck cancers, and gliomas, medulloblastomas, chondrosarcomas, and pancreatic tumors, and preferably include breast, colon, and renal cancers, and more preferably, colon cancer. The substances that modulate the activity of AUR1 and/or AUR2 preferably include, but are not limited to, antisense oligonucleotides, as described herein, and inhibitors of protein kinases, as determined by methods and screens described herein in the Examples.

Another aspect of the invention features a method for detection of aur1 and/or aur2 in a sample as a diagnostic tool for diseases comprising the steps of (a) contacting said sample with a nucleic acid probe which hybridizes under hybridization assay conditions to a nucleic acid target region of aur1 and/or aur2, said probe comprising the nucleic acid sequence encoding an AUR1 and/or AUR2 polypeptide, a fragment thereof, or the complement of said sequence or fragment; and (b) detecting the presence or amount of the probe:target region hybrid as an indication of said disease.

The aur1 and/or aur2 "target region" is the nucleotide base sequence set forth in SEQ ID NO:1 or SEQ ID NO:2, a functional derivative thereof, or a fragment thereof to which the nucleic acid probe will specifically hybridize. Specific hybridization indicates that in the presence of other nucleic acids the probe only hybridizes detectably with the aur1 and/or aur2 target region. Putative target regions can be identified by methods well known in the art consisting of alignment and comparison of the most closely related sequences in the database.

In preferred embodiments the nucleic acid probe hybridizes to an aur1 and/or aur2 target region encoding at least 12, 75, 90, 105, 120, 150, 200, 250, 300 or 350 contiguous amino acids of the full-length sequence set forth in SEQ ID NO:3 or SEQ ID NO:4 or a functional derivative thereof. Hybridization conditions should be such that hybridization occurs only with aur1 and/or aur2 in the presence of other nucleic acid molecules. Under stringent hybridization conditions only highly complementary nucleic acid sequences hybridize. Preferably, such conditions prevent hybridization of nucleic acids having 1 or 2 mismatches out of 20 contiguous nucleotides. Such conditions are defined supra.

The diseases for which detection of aur1 and/or aur2 in a sample could be diagnostic include diseases in which aur1 and/or aur2 nucleic acid (DNA and/or RNA) is amplified in comparison to normal cells. By "amplification" is meant increased numbers of aur1 and/or aur2 DNA or RNA in a cell compared with normal cells. In normal cells, aur1 and aur2 are found as single copy genes. In selected diseases, the chromosomal location of aur1 and/or aur2 is amplified, resulting in multiple copies of the gene, or amplification. Gene amplification can lead to amplification of aur1 and/or aur2 RNA, or aur1 and/or aur2 RNA can be amplified in the absence of aur1 and/or aur2 DNA amplification.

"Amplification" as it refers to RNA can be the detectable presence of aur1 and/or aur2 RNA in cells, since in some normal cells there is no basal expression of aur1 and/or aur2 RNA. In other normal cells, a basal level of expression of aur1 and/or aur2 exists, therefore in these cases amplification is the detection of at least 1–2-fold, and preferably more, aur1 and/or aur2 RNA, compared to the basal level.

The diseases that could be diagnosed by detection of aur1 and/or aur2 in a sample preferably include colon, breast, renal, ovarian, bladder, head and neck cancers, and gliomas, medulloblastomas, chondrosarcomas, and pancreatic tumors, and preferably include breast, colon, and renal cancers, and more preferably, colon cancer.

The test samples suitable for nucleic acid probing methods of the present invention include, for example, cells or nucleic acid extracts of cells, or biological fluids. The samples used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

Another aspect of the invention features antisense oligonucleotides to the nucleic acid sequences encoding AUR1 and/or AUR2 polypeptides contained in SEQ ID NO:1 and/or SEQ ID NO:2, and fragments thereof. In a preferred invention the antisense oligonucleotides are synthesized as phosphorothionates. In a preferred embodiment the antisense oligonucleotides comprise the following sequences 5'-3': nucleotides 1743–1763 of aur2: CAGGGCAGAGTG-GTCACTTTC (SEQ ID NO:30), nucleotides 42–62 of aur2: CGTCCGCCACTCCGACCAGCC (SEQ ID NO:31), nucleotides 1654–1674 of aur2: TGCAGTCGAACCTTGC-CTCCA (SEQ ID NO:32).

The antisense oligonucleotides of the invention are preferably used to inhibit AUR1 and/or AUR2 protein expression in vivo in normal and tumor cells. Antisense oligonucleotides can be used either singly or in combination. In a preferred embodiment, either SEQ ID NO:30 and SEQ ID NO:32 or SEQ ID NO:31 and SEQ ID NO:32 are used jointly. In a preferred embodiment, expression of AUR2 is significantly reduced, and more preferably reduced to below the limit of detection. In other preferred embodiments, treatment with SEQ ID NO:31 and SEQ ID NO:32 inhibits growth and/or induces apoptosis in cells. Antisense oligonucleotides can also be used to inhibit AUR1 and/or AUR2 protein expression in human tumor cell xenografts in nude mice. Antisense oligonucleotides may preferentially be used as a treatment in various human tumors over expressing AUR2.

Additional antisense oligonucleotides and effective combinations can be identified by methods well known in the art. Briefly, cells or tissues over expressing aur1 and/or aur2 can be contacted with antisense oligonucleotides, either singly or in combination, and the expression of aur1 and/or aur2 RNA, and/or AUR1 and/or AUR2 polypeptide can be determined by methods described herein. Preferably, treatment with aur1 and/or aur2 causes a decrease in the expression of aur1 and/or aur2 RNA and/or AUR1 and/or AUR2 polypeptide, more preferably expression is decreased significantly (1 to 2-fold), most preferably expression is decreased to an undetectable level.

The summary of the invention described above is non-limiting and other features and advantages of the invention will be apparent from the following description of the preferred embodiments, and from the claims.

DESCRIPTION OF FIGURES

FIG. 1 shows the sequences for human aur1 and aur2 deduced from full length cDNA clones isolated from normal duodenum, pancreatic carcinoma, and primary colorectal carcinoma libraries. Xenopus p46B (PIR:S53343), Drosophila aurora (PIR:A56220) and S. cerevesiae IPL1 (SWISS-PROT:P38991) are included in the alignment. The alignment was generated by also including the two murine (DDBJ:D21099 and GB:U80932), an additional xenopus (PIR:S53342), and two C. elegans (GB:U53336 and GB:U97196) sequences as input into msa, a parallel coded multiple sequence alignment program that was run on Mas-Par MP2216 supercomputer. Boxed residues are common to three or more of the sequences, shaded residues represent regions of amino acid similarity between two or more sequences, overlines correspond to the conserved Aurora Box1 and Aurora Box2 sequences, the arrow denotes the start of the C-terminal serine/threonine kinase domain, the circled residue indicates the location of a single nucleotide polymorphism described in the text, solid circles correspond to the location of various yeast and Drosophila mutants, and stars denote the site of the kinase inactivating and activating point mutants described in the text.

DETAILED DESCRIPTION OF THE INVENTION

The present invention relates in part to AUR1 and/or AUR2 polypeptides, nucleic acids encoding such polypeptides, cells containing such nucleic acids, antibodies to such polypeptides, assays utilizing such polypeptides, and methods relating to all of the foregoing. The present invention is based upon the isolation and characterization of new proteins which we have designated AUR1 and/or AUR2. The polypeptides and nucleic acids may be produced using well known and standard synthesis techniques when given the sequences presented herein.

I. Nucleic Acid Encoding AUR1 and/or AUR2 Polypeptides

Included within the scope of this invention are the functional equivalents of the herein-described isolated nucleic acid molecules. The degeneracy of the genetic code permits substitution of certain codons by other codons which specify the same amino acid and hence would give rise to the same protein. The nucleic acid sequence can vary substantially since, with the exception of methionine and tryptophan, the known amino acids can be coded for by more than one codon. Thus, portions or all of the AUR1 and/or AUR2 gene could be synthesized to give a nucleic acid sequence significantly different from that shown in SEQ ID NO:1 or SEQ ID NO:2. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of the nucleic acid formula shown in SEQ ID NO:1 or SEQ ID NO:2 or a derivative thereof. Any nucleotide or polynucleotide may be used in this regard, provided that its addition, deletion or substitution does not alter the amino acid sequence of SEQ ID NO:3 or SEQ ID NO:4 which is encoded by the nucleotide sequence. For example, the present invention is intended to include any nucleic acid sequence resulting from the addition of ATG as an initiation codon at the 5'-end of the inventive nucleic acid sequence or its derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the AUR1 and/or AUR2 genes and fragments thereof permitted by the genetic code are, therefore, included in this invention.

Further, it is possible to delete codons or to substitute one or more codons with codons other than degenerate codons to produce a structurally modified polypeptide, but one which has substantially the same utility or activity as the polypeptide produced by the unmodified nucleic acid molecule. As recognized in the art, the two polypeptides are functionally equivalent, as are the two nucleic acid molecules which give rise to their production, even though the differences between the nucleic acid molecules are not related to the degeneracy of the genetic code.

II. A Nucleic Acid Probe for the Detection of AUR1 and/or AUR2

Southern analysis with probes derived from the unique N-terminal regions of aur1 and aur2 indicate that they exist as single copy genes in human cells. However, under low stringency conditions, 1.3 kb and 3.2 kb SacI fragments which weakly hybridize to the aur1 probe were detected.

A nucleic acid probe of the present invention may be used to probe an appropriate chromosomal or cDNA library by usual hybridization methods to obtain another nucleic acid molecule of the present invention. A chromosomal DNA or cDNA library may be prepared from appropriate cells according to recognized methods in the art (cf. "Molecular Cloning: A Laboratory Manual", second edition, Cold Spring Harbor Laboratory, Sambrook, Fritsch, & Maniatis, eds., 1989).

In the alternative, chemical synthesis is carried out in order to obtain nucleic acid probes having nucleotide sequences which correspond to N-terminal and C-terminal portions of the amino acid sequence of the polypeptide of interest. The synthesized nucleic acid probes may be used as primers in a polymerase chain reaction (PCR) carried out in accordance with recognized PCR techniques, essentially according to PCR Protocols, "A Guide to Methods and Applications", Academic Press, Michael et al., eds., 1990, utilizing the appropriate chromosomal or cDNA library to obtain the fragment of the present invention.

One skilled in the art can readily design such probes based on the sequence disclosed herein using methods of computer alignment and sequence analysis known in the art ("Molecular Cloning: A Laboratory Manual", 1989, supra). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, as well as DNA probes, such probes being generated using techniques known in the art. The nucleic acid probe may be immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The samples used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

III. A Probe Based Method And Kit For Detecting AUR1 and/or AUR2

Aur1 RNA is broadly expressed in rapidly dividing cells derived from both normal and tumor tissues. Aur2 RNA is expressed in a more restricted pattern, being low or absent in most normal tissues, and abundant in only a subset of tumor-derived cell lines, particularly those of colon, renal, melanoma, and breast origin in which the 2.4 kb aur2 transcript is expressed in 96% (24 of 25). The 1.4 kb aur1 transcript was co-expressed at similar levels as aur2 in the same 24 tumor cell lines.

Aur2 RNA expression is also increased in approximately 54% (22/41) of 41 primary human colorectal tumors compared with matched normal colorectal controls. Aur2 RNA showed 4–28 fold overexpression in tumor versus normal tissue.

Human aur1 is located on chromosome 17p13.1 and human aur2 on chromosome 20q13.2. Aur2 maps adjacent to the vitamin D hydroxylase (CYP24) gene and the cosmid probe RMC20C001 that lie at 0.825–0.83 Flpter (fractional length from pter) on chromosome 20 (Tanner et al., Cancer res. 54:4257–4260, 1994; Tanner et al., Cancer Res. 56:3441–3445, 1996). Both of these markers have been characterized for their presence in the 20q13 amplicon common to many human malignancies, particularly those from breast, bladder, and colon (Tanner 1994, supra; Tanner 1996, supra; Kallioniemi et al., Proc. Natl. Acad. Sci. USA 91:2156–2160, 1994; Yaseen et al., Cancer Genet. Cytogenet. 44:83–97, 1990; Muleris et al., Cancer Genet. Cytogenet. 29:289–301, 1987; Schlegel et al., Cancer Res. 55:6002–6005, 1995; James et al., Oncogene 14:1059–1065, 1997; Solinas-Toldo et al., Cancer Res. 56:3803–3807, 1996; Bockmuhl et al., Laryngorhinootologie 75:408–414, 1996; Larramendy et al., Am. J. Pathol. 150:685–691, 1997; Reznikoff et al., Semin. Oncol. 23:571–584, 1996; Courjal et al., Br. J. Cancer 74:1984–1989, 1996; Iwabuchi et al., Cancer Res. 55:6172–6180, 1995; Bigner et al., Cancer Genet. Cytogenet. 30:91–101, 1988). The aur2-specific bands showed amplification in the tumor samples.

AUR2 DNA was amplified in 41 of 79 (52%) of the primary colorectal tumors for which suitable DNA was available for genotyping. Nine of twelve samples demonstrated a 2–8 fold amplification of AUR2 DNA in the tumors compared to normal tissue. Eleven of the samples showed a direct correlation between DNA amplification and RNA overexpression.

The most common regions of high copy amplification in human breast cancer have been localized to 17q22 and 20q13.2 (Tanner 1994, supra; Tanner 1996, supra; Kallioniemi 1994, supra). Low level amplification of 20q has been described in 6–18% of primary breast cancer and 40% of breast cancer cell lines. The incidence increases to 60% in BRCA2 positive breast cancers (Tanner 1994, supra; Tanner 1996, supra; Kallioniemi 1994, supra; Tirkkonen et al., Cancer Res. 57:1222–1227, 1997). High levels of 20q amplification correlate with poor prognosis for patients with node negative breast cancer (Isola et al., Am. J. Pathol. 147:905–911, 1995). Low level amplification of 20q has also been noted in colon cancer, ovarian cancer, bladder cancer, gliomas, medulloblastomas, chondrosarcomas, pancreatic tumors, and head and neck cancers (Yaseen 1990, supra; Muleris 1987, supra; Schlegel 1995, supra; James 1997, supra; Solinas-Toldo 1996, supra; Bockmuhl 1996, supra; Larramendy 1997, supra; Reznikoff 1996, supra; Courjal 1996, supra; Iwabuchi 1995, supra; Bigner 1988, supra). Several studies have also found chromosomal gains of 20q in approximately 60% of primary colorectal carcinomas (Yaseen 1990, supra; Muleris 1987, supra; Schlegel 1995, supra). Cell culture models have suggested that low-level amplification of 20q is associated with immortalization and subsequent high-level amplification correlates with chromosomal instability (Savalieva et al., Oncogene 14:551–560, 1997).

AUR2 DNA was amplified in 41 of 79 (52%) of primary colorectal tumors. The CYP24 gene was coamplified with aur2 in 37 of 41 (90%) matched pairs, and was only once found amplified in the absence of aur2 amplification. Aur2 DNA amplification and RNA overexpression is highly correlated (r=0.695). DNA amplification may be a mechanism for aur2 activation and aur2 may be the oncogene at 20q13 whose high level amplification correlates with poor clinical outcome in a variety of solid tumors (Isola 1995, supra).

One method of detecting the presence of aur1 and/or aur2 in a sample comprises (a) contacting said sample with the above-described nucleic acid probe under conditions such that hybridization occurs, and (b) detecting the presence of said probe bound to said nucleic acid molecule. One skilled in the art would select the nucleic acid probe according to techniques known in the art as described above. Samples to be tested include but should not be limited to RNA samples of human tissue.

A kit for detecting the presence of aur1 and/or aur2 in a sample comprises at least one container means having disposed therein the above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymatic labeled probes (horseradish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art.

IV. DNA Constructs Comprising an Aur1 and/or Aur2 Nucleic Acid Molecule and Cells Containing These Constructs The present invention also relates to a recombinant DNA molecule comprising, 5' to 3', a promoter effective to initiate transcription in a host cell and the above-described nucleic acid molecules. In addition, the present invention relates to a recombinant DNA molecule comprising a vector and an above-described nucleic acid molecule. The present invention also relates to a nucleic acid molecule comprising a transcriptional region functional in a cell, a sequence complementary to an RNA sequence encoding an amino acid sequence corresponding to the above-described polypeptide, and a transcriptional termination region functional in said cell. The above-described molecules may be isolated and/or purified DNA molecules.

The present invention also relates to a cell or organism that contains an above-described nucleic acid molecule and thereby is capable of expressing a peptide. The polypeptide may be purified from cells which have been altered to express the polypeptide. A cell is said to be "altered to express a desired polypeptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an AUR1 and/or AUR2 polypeptide may be obtained by the above-described methods. This region may be retained for its transcriptional termination regulatory sequences, such as termination and polyadenylation. Thus, by retaining the 3'-region naturally contiguous to the DNA sequence encoding an AUR1 and/or AUR2 polypeptide, the transcriptional termination signals may be provided. Where the transcriptional termination signals are not satisfactorily functional in the expression host cell, then a 3' region functional in the host cell may be substituted.

Two DNA sequences (such as a promoter region sequence and an aur1 and/or aur2 sequence) are said to be operably linked if the nature of the linkage between the two DNA sequences does not (1) result in the introduction of a frame-shift mutation, (2) interfere with the ability of the promoter region sequence to direct the transcription of an aur1 and/or aur2 gene sequence, or (3) interfere with the ability of the aur1 and/or aur2 gene sequence to be transcribed by the promoter region sequence. Thus, a promoter region would be operably linked to a DNA sequence if the promoter were capable of effecting transcription of that DNA sequence. Thus, to express an aur1 and/or aur2 gene, transcriptional and translational signals recognized by an appropriate host are necessary.

The present invention encompasses the expression of the aur1 and/or aur2 gene (or a functional derivative thereof) in either prokaryotic or eukaryotic cells. Prokaryotic hosts are, generally, very efficient and convenient for the production of recombinant proteins and are, therefore, one type of preferred expression system for the aur1 and/or aur2 gene. Prokaryotes most frequently are represented by various strains of E. coli. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include γgt10, γgt11 and the like; and suitable virus vectors may include pMAM-neo, pKRC and the like. Preferably, the selected vector of the present invention has the capacity to replicate in the selected host cell.

Recognized prokaryotic hosts include bacteria such as E. coil, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express aur1 and/or aur2 (or a functional derivative thereof) in a prokaryotic cell, it is necessary to operably link the aur1 and/or aur2 sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, λacZ, λacI, and gal promoters of E. coli, the α-amylase (Ulmanen et al., J. Bacteriol. 162:176–182, 1985) and the ζ-28-specific promoters of B. subtilis (Gilman et al., Gene Sequence 32:11–20, 1984), the promoters of the bacteriophages of Bacillus (Gryczan, In: The Molecular Biology of the Bacilli, Academic Press, Inc., NY, 1982), and Streptomyces promoters (Ward et al., Mol. Gen. Genet. 203:468–478, 1986). Prokaryotic promoters are reviewed by Glick (Ind. Microbiot. 1:277–282, 1987), Cenatiempo (Biochimie 68:505–516, 1986), and Gottesman (Ann. Rev. Genet. 18:415–442, 1984).

Proper expression in a prokaryotic cell also requires the presence of a ribosome binding site upstream of the gene sequence-encoding sequence. Such ribosome binding sites are disclosed, for example, by Gold et al. (Ann. Rev. Microbiol. 35:365–404, 1981). The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transfornants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the AUIR1 and/or AUR2 peptide of interest. Suitable hosts may often include eukaryotic cells. Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin and their derivatives. Preferred mammalian host cells include SP2/0 and J558L, as well as neuroblastoma cell lines such as IMR 332, which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the Drosophila larvae. Using insect cells as hosts, the Drosophila alcohol dehydrogenase promoter can be used (Rubin, Science 240:1453–1459, 1988). Alternatively, baculovirus vectors can be engineered to express large amounts of AUR1 and/or AUR2 in insects cells (Jasny, Science 238:1653, 1987; Miller et al., In: Genetic Engineering, Vol. 8, Plenum, Setlow et al., eds., pp. 277–297, 1986).

Any of a series of yeast expression systems can be utilized which incorporate promoter and termination elements from the actively expressed sequences coding for glycolytic enzymes that are produced in large quantities when yeast are grown in mediums rich in glucose. Known glycolytic gene sequences can also provide very efficient transcriptional control signals. Yeast provides substantial advantages in that it can also carry out post-translational modifications. A number of recombinant DNA strategies exist utilizing strong promoter sequences and high copy number plasmids which can be utilized for production of the desired proteins in yeast. Yeast recognizes leader sequences on cloned mammalian genes and secretes peptides bearing leader sequences (i.e., pre-peptides). Several possible vector systems are available for the expression of aur1 and/or aur2 in a mammalian host.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of aur1 and/or aur2 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., J. Mol. Appl. Gen. 1:273–288, 1982); the TK promoter of Herpes virus (McKnight, Cell 31:355–365, 1982); the SV40 early promoter (Benoist et al., Nature (London) 290:304–31, 1981); and the yeast gal4 gene sequence promoter (Johnston et al., Proc. Natl. Acad. Sci. (USA) 79:6971–6975, 1982; Silver et al., Proc. Natl. Acad. Sci. (USA) 81:5951–5955, 1984).

Translation of eukaryotic mRNA is initiated at the codon which encodes the first methionine. For this reason, it is preferable to ensure that the linkage between a eukaryotic promoter and a DNA sequence which encodes AUR1 and/or AUR2 (or a functional derivative thereof) does not contain any intervening codons which are capable of encoding a methionine (i.e., AUG). The presence of such codons results either in the formation of a fusion protein (if the AUG codon is in the same reading frame as the aur1 and/or aur2 coding sequence) or a frame-shift mutation (if the AUG codon is not in the same reading frame as the aur1 and/or aur2 coding sequence).

An aur1 and/or aur2 nucleic acid molecule and an operably linked promoter may be introduced into a recipient prokaryotic or eukaryotic cell either as a nonreplicating DNA or RNA molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis mRNA. These elements may include splice signals, as well as transcription promoters, enhancers, and termination signals. cDNA expression vectors incorporating such elements include those described by Okayama (Mol. Cell. Biol. 3:280-?, 1983).

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coil* (such as, for example, pBR322, ColE, pSC101, pACYC 184, πVX; "Molecular Cloning: A Laboratory Manual", 1989, supra). Bacillus plasmids include pC194, pC221, pT127, and the like (Gryczan, In: The Molecular Biology of the Bacilli, Academic Press, NY, pp. 307–329, 1982). Suitable Streptomyces plasmids include p1J101 (Kendall et al., J. Bacteriol. 169:4177–4183, 1987), and streptomyces bacteriophages such as φC31 (Chater et al., In: Sixth International Symposium on Actinomycetales Biology, Akademiai Kaido, Budapest, Hungary, pp. 45–54, 1986). Pseudomonas plasmids are reviewed by John et al. (Rev. Infect. Dis. 8:693–704, 1986), and Izaki (Jpn. J. Bacteriol. 33:729–742, 1978).

Preferred eukaryotic plasmids include, for example, BPV, vaccinia, SV40, 2-micron circle, and the like, or their derivatives. Such plasmids are well known in the art (Botstein et al., Miami Wntr. Symp. 19:265–274, 1982; Broach, In: "The Molecular Biology of the Yeast Saccharomyces: Life Cycle and Inheritance", Cold Spring Harbor Laboratory, Cold Spring Harbor, N.Y., p. 445–470, 1981; Broach, Cell 28:203–204, 1982; Bollon et al., J. Ctin. Hematol. Oncol. 10:39–48, 1980; Maniatis, In: Cell Biology: A Comprehensive Treatise, Vol. 3, Gene Sequence Expression, Academic Press, NY, pp. 563–608, 1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene(s) results in the production of AUR1 and/or AUR2 or fragments thereof. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

V. Purified AUR1 and/or AUR2 Polypeptides

AUR1 and AUR2 are related serine/threonine kinases with short N-terminal extensions. The Drosophila and yeast homologs appear to be involved in mitotic regulation. The human proteins appear to be involved in cancer and/or other signal transduction disorders.

Primary sequence analysis of the human aur1 and aur2 genes reveals that they contain a highly conserved C-terminal protein kinase domain with all the characteristic motifs of a serine/threonine kinase. In addition, the 73 to 129 amino acid N-terminal domains of human aur1 and aur2 contain two distantly conserved motifs present in the non-catalytic region of all aurora genes which may play a regulatory role or function as a substrate binding motif.

The first motif includes a 10 amino stretch, $KENX_4PVK$, termed Aurora Box1. The second motif is centered around a 15 amino acid stretch, $QX_9AQRVL$, termed Aurora Box 2. Several potential serine and threonine phosphorylation sites are also conserved among these proteins including a protein kinase A phosphorylation motif, RRXT, in the activation loop of the kinase, which suggests a regulatory pathway similar to the cell cycle regulated CDC2/CDK-related proteins.

A temperature sensitive mutant of the yeast IPL1 gene consists of a Thr to Ala substitution within the activation loop2, suggesting that phosphorylation at this site may be biologically relevant. Additional mutants in the yeast (Chan et al., Genetics 135:677–691, 1993) and Drosophila (Glover et al. Cell 81:95–105, 1995) homologues of aurora have been mapped exclusively to the kinase domain, except for a single Drosophila mutant that involves a mutation at Asp47 within the N-terminal Aurora Box2. These mutations result in abnormal nuclei, chromosome missegregation, and monopolar spindles.

Aur2 expression is primarily restricted to fetal liver, adult testis, and thymus, suggestive of a normal role for these proteins in meiotic division. Human Aur1 is also expressed at highest levels in normal testis and thymus, with a moderate level of expression in lung and small intestine. Very weak expression of Aur2 is also detected in bone marrow, lymph node, and spleen, and no expression is detected in all other adult tissues examined.

Additional studies demonstrate tight temporal regulation of these transcripts during mitosis (and Kimura et al., J. Biol. Chem. 272:13766–13771, 1997). Both AUR1 and AUR2 appear to regulate nuclear division, with disruption of their signaling resulting in polyploid cells. This phenotype is likely due to chromosomal missegregation, as seen with the yeast homologue IPL1.

AUR2 appears to play a role in cellular transformation. Ectopic expression of activated AUR2, which can phosphorylate myelin basic protin in vitro, confers a growth advantage to NIH3T3 cells in low serum as compared to wild-type AUR2, kinase inactive AUR2, and vector. In addition, only NIH3T3 cells expressing activated AUR2 grow large colonies in soft agar thus resulting in anchorage-dependent growth.

However, in a rat1 fibroblast system, both the wild-type and activated AUR2 (T288D) proteins were able to phosphorylate the artificial substrate, α-casein, over the levels observed in the vector control cell line. In addition, cells expressing the wild-type as well as the activated mutant AUR2 formed colonies in soft agar, in contrast to the lack of growth by cells expressing the kinase inactive AUR2.

A variety of methodologies known in the art can be utilized to obtain the peptide of the present invention. The peptide may be purified from tissues or cells which naturally produce the peptide. Alternatively, the above-described isolated nucleic acid fragments could be used to express the AUR1 and/or AUR2 protein in any organism. The samples of the present invention include cells, protein extracts or membrane extracts of cells, or biological fluids. The samples will vary based on the assay format, the detection method, and the nature of the tissues, cells or extracts used as the sample.

Any eukaryotic organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: size-exclusion chromatography, HPLC, ion-exchange chromatography, and immuno-affinity chromatography.

VI. An Antibody Having Binding Affinity to an AUR1 and/or AUR2 Polypeptide and a Hybridoma Containing the Antibody The present invention relates to an antibody having binding affinity to an AUR1 and/or AUR2 polypeptide. The polypeptide may have the amino acid sequence set forth in SEQ ID NO:3 or SEQ ID NO:4, or a functional derivative thereof, or at least 9 contiguous amino acids thereof (preferably, at least 20, 30, 35, or 40 contiguous amino acids thereof).

The present invention also relates to an antibody having specific binding affinity to an AUR1 and/or AUR2 polypeptide. Such an antibody may be isolated by comparing its binding affinity to an AUR1 and/or AUR2 polypeptide with its binding affinity to other polypeptides. Those which bind selectively to AUR1 and/or AUR2 would be chosen for use in methods requiring a distinction between AUR1 and/or AUR2 and other polypeptides. Such methods could include, but should not be limited to, the analysis of altered AUR1 and/or AUR2 expression in tissue containing other polypeptides.

The AUR1 and/or AUR2 proteins of the present invention can be used in a variety of procedures and methods, such as for the generation of antibodies, for use in identifying pharmaceutical compositions, and for studying DNA/protein interaction.

The AUR1 and/or AUR2 peptide of the present invention can be used to produce antibodies or hybridomas. One skilled in the art will recognize that if an antibody is desired, such a peptide would be generated as described herein and used as an immunogen. The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting. The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands, 1984; St. Groth et al., J. Immunol. Methods 35:1–21, 1980). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Res. 175:109–124, 1988). Hybridomas secreting the desired antibodies are cloned and the class and subclass are determined using procedures known in the art (Campbell, "Monoclonal Antibody Technology: Laboratory Techniques in Biochemistry and Molecular Biology", supra, 1984).

For polyclonal antibodies, antibody containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Stemberger et al., J. Histochem. Cytochem. 18:315, 1970; Bayer et al., Meth. Enzym. 62:308-, 1979; Engval et al., Immunol. 109:129-, 1972; Goding, J. Immunol._Meth. 13:215-, 1976). The labeled antibodies of the present invention can be used for in vitro, in vivo, and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10, 1986; Jacoby et al., Meth. Enzym. 34, Academic Press, N.Y., 1974). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides (Hurby et al., "Application of Synthetic Peptides: Antisense Peptides", In Synthetic Peptides, A User's Guide, W. H. Freeman, NY, pp. 289–307, 1992; Kaspczak et al., Biochemistry 28:9230–9238, 1989).

Anti-peptide peptides can be generated by replacing the basic amino acid residues found in the AUR1 and/or AUR2 peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

VII. An Antibody Based Method and Kit for Detecting AUR1 and/or AUR2

Antibodies to AUR2 protein detect a protein of approximately 46 kDa (the size of the AUR2 protein) in 2 primary human colon cancers, but not in adjacent samples of normal tissue. Endogenous AUR2 is also detected in cultured tumor cell lines.

The present invention encompasses a method of detecting an AUR1 and/or AUR2 polypeptide in a sample, comprising: (a) contacting the sample with an above-described antibody, under conditions such that immunocomplexes form, and (b) detecting the presence of said antibody bound to the polypeptide. In detail, the methods comprise incubating a test sample with one or more of the antibodies of the present invention and assaying whether the antibody binds to the test sample. Altered levels of AUR1 and/or AUR2 in a sample as compared to normal levels may indicate disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard ("An Introduction to Radioimmunoassay and Related Techniques" Elsevier Science Publishers, Amsterdam, The Netherlands, 1986), Bullock et al. ("Techniques in Immunocytochemistry," Academic Press, Orlando, Fla. Vol. 1,1982; Vol. 2, 1983; Vol. 3, 1985), Tijssen ("Practice and Theory of Enzyme Immunoassays: Laboratory Techniques in Biochemistry and Molecular Biology," Elsevier Science Publishers, Amsterdam, The Netherlands, 1985).

The immunological assay test samples of the present invention include cells, protein or membrane extracts of cells, or biological fluids such as blood, serum, plasma, or urine. The test samples used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is testable with the system utilized.

A kit contains all the necessary reagents to carry out the previously described methods of detection. The kit may comprise: (i) a first container means containing an above-described antibody, and (ii) second container means containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits. One skilled in the art will readily recognize that the antibodies described in the present invention can readily be incorporated into one of the established kit formats which are well known in the art.

VIII. Isolation of Compounds which Interact with AUR1 and/or AUR2

The present invention also relates to a method of detecting a compound capable of binding to an AUR1 and/or AUR2 polypeptide comprising incubating the compound with AUR1 and/or AUR2 and detecting the presence of the compound bound to AUR1 and/or AUR2. The compound may be present within a complex mixture, for example, serum, body fluid, or cell extracts.

The present invention also relates to a method of detecting an agonist or antagonist of AUR1 and/or AUR2 activity or AUR1 and/or AUR2 binding partner activity comprising incubating cells that produce AUR1 and/or AUR2 in the presence of a compound and detecting changes in the level of AUR1 and/or AUR2 activity or AUR1 and/or AUR2 binding partner activity. The compounds thus identified would produce a change in activity indicative of the presence of the compound. The compound may be present within a complex mixture, for example, serum, body fluid, or cell extracts. Once the compound is identified it can be isolated using techniques well known in the art.

The present invention also encompasses a method of agonizing (stimulating) or antagonizing AUR1 and/or AUR2 associated activity in a mammal comprising administering to said mammal an agonist or antagonist to AUR1 and/or AUR2 in an amount sufficient to effect said agonism or antagonism. A method of treating diseases in a mammal with an agonist or antagonist of AUR1 and/or AUR2 related activity comprising administering the agonist or antagonist to a mammal in an amount sufficient to agonize or antagonize AUR1 and/or AUR2 associated functions is also encompassed in the present application.

IX. Transgenic Animals

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., Proc. Nat. Acad. Sci. USA 82: 4438–4442, 1985). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout (Experientia 47: 897–905, 1991). Other procedures for introduction of DNA into tissues of animals are described in U.S. Pat. No. 4,945,050 (Sandford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice (Hammer et al., Cell 63:1099–1112, 1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art (Teratocarcinomas and Embryonic Stem Cells, A Practical Approach, E. J. Robertson, ed., IRL Press, 1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination (Capecchi, Science 244:1288–1292, 1989). Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al. (Nature 338: 153–156, 1989), the teachings of which are incorporated herein in their entirety including any drawings. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene.

Procedures for the production of non-rodent mammals and other animals have been discussed by others (Houdebine and Chourrout, supra; Pursel et al., Science 244:1281–1288, 1989; and Simms et al., Bio/Technology 6:179–183, 1988).

Thus, the invention provides transgenic, nonhuman mammals containing a transgene encoding an AUR1 and/or AUR2 polypeptide or a gene effecting the expression of an AUR1 and/or AUR2 polypeptide. Such transgenic nonhuman mammals are particularly useful as an in vivo test system for studying the effects of introducing an AUR1 and/or AUR2 polypeptide, or regulating the expression of an AUR1 and/or AUR2 polypeptide (i.e., through the introduction of additional genes, antisense nucleic acids, or ribozymes).

A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. The transgenic DNA may encode for a human AUR1 and/or AUR2 polypeptide. Native expression in an animal may be reduced by providing an amount of antisense RNA or DNA effective to reduce expression of the receptor.

X. Gene Therapy

AUR2 protein expression in the human tumor cell line H1299 is significantly down regulated in the presence of any one of three antisense phosphothionate oligonucleotides (SEQ ID NO:30, SEQ ID NO:31 and SEQ ID NO:32) which target specific regions of human aur2 mRNA transcripts. When used in combination, oligonucleotides SEQ ID NO:30 and SEQ ID NO:32, and SEQ ID NO:31 and SEQ ID NO:32 reduce the expression of AUR2 protein below the limit of detection. Treatment of H1299 cells with the combination of SEQ ID NO:31 and SEQ ID NO:32 inhibited the growth of this tumor cell line, and induced apoptosis as measured by FACs.

AUR1 and/or AUR2 or its genetic sequences will also be useful in gene therapy (reviewed in Miller, Nature 357:455–460, 1992). Miller states that advances have resulted in practical approaches to human gene therapy that have demonstrated positive initial results. The basic science of gene therapy is described in Mulligan (Science 260:926–931, 1993).

In one preferred embodiment, an expression vector containing the AUR1 and/or AUR2 coding sequence is inserted into cells, the cells are grown in vitro and then infused in large numbers into patients. In another preferred embodiment, a DNA segment containing a promoter of choice (for example a strong promoter) is transferred into cells containing an endogenous aur1 and/or aur2 in such a manner that the promoter segment enhances expression of the endogenous aur1 and/or aur2 gene (for example, the promoter segment is transferred to the cell such that it becomes directly linked to the endogenous aur1 and/or aur2 gene).

The gene therapy may involve the use of an adenovirus containing aur1 and/or aur2 cDNA targeted to a tumor, systemic AUR1 and/or AUR2 increase by implantation of engineered cells, injection with aur1 and/or aur2 virus, or injection of naked aur1 and/or aur2 DNA into appropriate tissues.

Target cell populations may be modified by introducing altered forms of one or more components of the protein complexes in order to modulate the activity of such complexes. For example, by reducing or inhibiting a complex component activity within target cells, an abnormal signal transduction event(s) leading to a condition may be decreased, inhibited, or reversed. Deletion or missense mutants of a component, that retain the ability to interact with other components of the protein complexes but cannot function in signal transduction may be used to inhibit an abnormal, deleterious signal transduction event.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding recombinant AUR1 and/or AUR2 protein into the targeted cell population (e.g., tumor cells). Methods which are well known to those skilled in the art can be used to construct recombinant viral vectors containing coding sequences (Maniatis et al., Molecular Cloning: A Laboratory Manual, Cold Spring Harbor Laboratory, N.Y., 1989; Ausubel et al., Current Protocols in Molecular Biology, Greene Publishing Associates and Wiley Interscience, N.Y., 1989). Alternatively, recombinant nucleic acid molecules encoding protein sequences can be used as naked DNA or in a reconstituted system e.g., liposomes or other lipid systems for delivery to target cells (e.g., Felgner et al., Nature 337:387–8, 1989). Several other methods for the direct transfer of plasmid DNA into cells exist for use in human gene therapy and involve targeting the DNA to receptors on cells by complexing the plasmid DNA to proteins (Miller, supra).

In its simplest form, gene transfer can be performed by simply injecting minute amounts of DNA into the nucleus of a cell, through a process of microinjection (Capecchi, Cell 22:479–88, 1980). Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen et al., Mol. Cell Biol. 7:2745–52, 1987); electroporation, wherein cells are exposed to large voltage pulses to introduce holes into the membrane (Chu et al., Nucleic Acids Res. 15:1311–26, 1987); lipofection/liposome fusion, wherein DNA is packaged into lipophilic vesicles which fuse with a target cell (Felgner et al., Proc. Natl. Acad. Sci. USA. 84:7413–7417, 1987); and particle bombardment using DNA bound to small projectiles (Yang et al., Proc. Natl. Acad. Sci. 87:9568–9572, 1990). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene (Curiel et al., Am. J. Respir. Cell. Mol. Biol., 6:247–52, 1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding an AUR1 and/or AUR2 polypeptide is provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

XI. Compounds that Modulate the Function of AUR1 and/or Aur2 Proteins

In an effort to discover novel treatments for diseases, biomedical researchers and chemists have designed, synthesized, and tested molecules that inhibit the function of protein kinases. Some small organic molecules form a class of compounds that modulate the function of protein kinases. Examples of molecules that have been reported to inhibit the function of protein kinases include, but are not limited to, bis monocyclic, bicyclic or heterocyclic aryl compounds (PCT WO 92/20642, published Nov. 26, 1992 by Maguire et al.), vinylene-azaindole derivatives (PCT WO 94/14808, published Jul. 7, 1994 by Ballinari et al.), 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT WO 94/03427, published Feb. 17, 1994 by Denny et al.), tricyclic polyhydroxylic compounds (PCT WO 92/21660, published Dec. 10, 1992 by Dow), and benzylphosphonic acid compounds (PCT WO 91/15495, published Oct. 17, 1991 by Dow et al). The compounds that can traverse cell membranes and are resistant to acid hydrolysis are potentially advantageous therapeutics as they can become highly bioavailable after being administered orally to patients. However, many of these protein kinase inhibitors only weakly inhibit the function of protein kinases. In addition, many inhibit a variety of protein kinases and will therefore cause multiple side-effects as therapeutics for diseases.

Some indolinone compounds, however, form classes of acid resistant and membrane permeable organic molecules. WO 96/22976, published Aug. 1, 1996 by Ballinari et al. describes hydrosoluble indolinone compounds that harbor tetralin, naphthalene, quinoline, and indole substituents fused to the oxindole ring. These bicyclic substituents are in turn substituted with polar moieties including hydroxylated alkyl, phosphate, and ether moieties. U.S. patent application Ser. Nos. 08/702,232, filed Aug. 23, 1996, entitled "Indolinone Combinatorial Libraries and Related Products and Methods for the Treatment of Disease" by Tang et al. and 08/485,323, filed Jun. 7, 1995, entitled "Benzylidene-Z-Indoline Compounds for the Treatment of Disease" by Tang et al. and International Patent Publication WO 96/22976, published Aug. 1, 1996 by Ballinari et al., all of which are incorporated herein by reference in their entirety, including any drawings, describe indolinone chemical libraries of indolinone compounds harboring other bicyclic moieties as well as monocyclic moieties fused to the oxindole ring. Applications 08/702,232, filed Aug. 23, 1996, entitled "Indolinone Combinatorial Libraries and Related Products and Methods for the Treatment of Disease" by Tang et al., 08/485,323, filed Jun. 7, 1995, entitled "Benzylidene-Z-Indoline Compounds for the Treatment of Disease" by Tang et al., and WO 96/22976, published Aug. 1, 1996 by Ballinari et al. teach methods of indolinone synthesis, methods of testing the biological activity of indolinone compounds in cells, and inhibition patterns of indolinone derivatives.

Other examples of substances capable of modulating AUR1 and/or AUR2 activity include, but are not limited to, tyrphostins, quinazolines, quinoxolines, and quinolines.

The quinazolines, tyrphostins, quinolines, and quinoxolines referred to above include well known compounds such as those described in the literature. For example, representative publications describing quinazoline include Barker et al., EPO Publication No. 0 520 722 A1; Jones et al., U.S. Pat. No. 4,447,608; Kabbe et al., U.S. Pat. No. 4,757,072; Kaul and Vougioukas, U.S. Pat. No. 5, 316,553; Kreighbaum and Comer, U.S. Pat. No. 4,343,940; Pegg and Wardleworth, EPO Publication No. 0 562 734 A1; Barker et al., *Proc. of Am. Assoc. for Cancer Research* 32:327 (1991); Bertino, J. R., *Cancer Research* 3:293–304 (1979); Bertino, J. R., *Cancer Research* 9(2 part 1):293–304 (1979); Curtin et al., *Br. J. Cancer* 53:361–368 (1986); Fernandes et al., *Cancer Research* 43:1117–1123 (1983); Ferris et al. *J. Org. Chem.* 44(2):173–178; Fry et al., *Science* 265:1093–1095 (1994); Jackman et al., *Cancer Research* 51:5579–5586 (1981); Jones et al. *J. Med. Chem.* 29(6):1114–1118; Lee and Skibo, *Biochemistry* 26(23):7355–7362 (1987); Lemus et al., *J. Org. Chem.* 54:3511–3518 (1989); Ley and Seng, *Synthesis* 1975:415–522 (1975); Maxwell et al., *Magnetic Resonance in Medicine* 17:189–196 (1991); Mini et al., *Cancer Research* 45:325–330 (1985); Phillips and Castle, *J. Heterocyclic Chem.* 17(19):1489–1596 (1980); Reece et al., *Cancer Research* 47(11):2996–2999 (1977); Sculier et al., *Cancer Immunol. and Immunother.* 23:A65 (1986); Sikora et al., *Cancer Letters* 23:289–295 (1984); Sikora et al., *Analytical Biochem.* 172:344–355 (1988); all of which are incorporated herein by reference in their entirety, including any drawings.

Quinoxaline is described in Kaul and Vougioukas, U.S. Pat. No. 5,316,553, incorporated herein by reference in its entirety, including any drawings.

Quinolines are described in Dolle et al., *J. Med. Chem.* 37:2627–2629 (1994); MaGuire, *J. Med. Chem.* 37:2129–2131 (1994); Burke et al., *J. Med. Chem.* 36:425–432 (1993); and Burke et al. *BioOrganic Med. Chem. Letters* 2:1771–1774 (1992), all of which are incorporated by reference in their entirety, including any drawings.

Tyrphostins are described in Allen et al., *Clin. Exp. Immunol.* 91:141–156 (1993); Anafi et al., *Blood* 82:12:3524–3529 (1993); Baker et al., *J. Cell Sci.* 102:543–555 (1992); Bilder et al., *Amer. Physiol. Soc.* pp. 6363–6143:C721–C730 (1991); Brunton et al., *Proceedings of Amer. Assoc. Cancer Rsch.* 33:558 (1992); Bryckaert et al., *Experimental Cell Research* 199:255–261 (1992); Dong et al., *J. Leukocyte Biology* 53:53–60 (1993); Dong et al., *J. Immunol.* 151(5):2717–2724 (1993); Gazit et al., *J. Med. Chem.* 32:2344–2352 (1989); Gazit et al., "*J. Med. Chem.* 36:3556–3564 (1993); Kaur et al., *Anti-Cancer Drugs* 5:213–222 (1994); Kaur et al., King et al., *Biochem. J.* 275:413–418 (1991); Kuo et al., *Cancer Letters* 74:197–202 (1993); Levitzki, A., *The FASEB J.* 6:3275–3282 (1992); Lyall et al., *J. Biol. Chem.* 264:14503–14509 (1989); Peterson et al., *The Prostate* 22:335–345 (1993); Pillemer et al., *Int. J. Cancer* 50:80–85 (1992); Posner et al., *Molecular Pharmacology* 45:673–683 (1993); Rendu et al., *Biol. Pharmacology* 44(5):881–888 (1992); Sauro and Thomas, *Life Sciences* 53:371–376 (1993); Sauro and Thomas, *J. Pharm. and Experimental Therapeutics* 267(3):119–1125 (1993); Wolbring et al., *J. Biol. Chem.* 269(36):22470–22472 (1994); and Yoneda et al., *Cancer Research* 51:4430–4435 (1991); all of which are incorporated herein by reference in their entirety, including any drawings.

Other compounds that could be used as modulators include oxindolinones such as those described in U.S. patent application Ser. No. 08/702,232 filed Aug. 23, 1996, incorporated herein by reference in its entirety, including any drawings.

EXAMPLES

The examples below are non-limiting and are merely representative of various aspects and features of the present invention. The examples below demonstrate the isolation, and characterization of the novel proteins AUR1 and AUR2.

Example 1

Cloning of Aur1 and Aur2 and Structural Motifs
Materials and Methods:
Molecular Cloning Total RNAs were isolated using the Guanidine Salts/Phenol extraction protocol of Chomczynski and Sacchi (Anal. Biochem. 162:156–159, 1987) from normal human prostate, duodenum, ovary, liver, pituitary, brain, thymus, and salivary gland, from human HEPM cells (palatal mesenchyme), from primary human Wilm's tumor and ovarian carcinoma, and from human tumor cell lines originating from colon/rectum (HT29, SW480, SW1463, SW1417, SW837, SW948, SW620, SW403, SW1116, T84, HTC15, LS123, and Caco-2), kidney (CaKi-1, CaKi-2), liver (SK-HEP-1), pancreas (HS766T, ASPC, Capan-1), and breast (MCF7).

These RNAs were used as templates to generate single-stranded cDNAs using the Superscript Preamplification System for First Strand Synthesis kit purchased from GibcoBRL (Life Technologies, U.S.A.; Gerard et al. 1989, FOCUS 11, 66) under conditions recommended by manufacturer. A typical reaction used 10 $\mu$g total RNA or 2 $\mu$g poly(A)$^+$ RNA with 1.5 $\mu$g oligo(dT)$_{12-18}$ in a reaction volume of 60 $\mu$L. The product was treated with RNaseH and diluted to 100 $\mu$L with H$_2$O. For subsequent PCR amplification, 1–4 $\mu$L of these sscDNAs were used in each reaction.

Oligonucleotides were synthesized on an Applied Biosystems 394 DNA synthesizer using established phosphoratnidite chemistry and were used unpurified after precipitation with ethanol. The degenerate oligonucleotide primers are: A=5'-GARTTYGGNGARGTNTTYYTNGC-3' (SEQ ID NO:16) (sense) and DVW=5'-AGNACNCCRAANGCCCACACRTC-3' (SEQ ID NO:17) (antisense).

These primers were derived from the peptide sequences EFGEVFLA (SEQ ID NO:18) (sense strand from kinase subdomain I) and DVW(A/S)FGVL (SEQ ID NO:29; antisense strand from kinase subdomain IX), respectively. Degenerate nucleotide residue designations are: N=A, C, G, or T; R=A or G; and Y=C or T. Using CCK4 as a template, these primers produce a product of 567 bp.

A PCR reaction was performed using Primers A and DVW applied to the single-stranded sources listed above. The primers were added at a final concentration of 5 $\mu$M each to a mixture containing 10 mM TrisHCl (pH8.3), 50 mM KCl, 1.5 mM MgCl$_2$, 200 $\mu$M each deoxynucleoside triphosphate, 0.001% gelatin, and 1.5 U AmpliTaq DNA Polymerase (Perkin-Elmer/Cetus), and 1–4 $\mu$L cDNA. Following 3 min denaturation at 95° C., the cycling conditions were 94° C. for 30 s, 37° C. for 1 min a 2 min ramp to 72° C., and 72° C. for 1 min for the first 3 cycles, followed by 94° C. for 30 s, 50° C. for 1 min, and 72° C. for 1 min 45 s for 35 cycles. PCR fragments migrating at between 500–600 bp were isolated from 2% agaorse gels using GeneClean (Bio101), and T-A cloned into the pCRII vector (Invitrogen Corp. U.S.A.) according to the manufacturer's protocol.

Colonies were selected for mini plasmid DNA-preparations using Qiagen columns and the plasmid DNAs were sequenced using a cycle sequencing dye-terminator kit with AmpliTaq DNA Polymerase, FS (ABI, Foster City, Calif.). Sequencing reaction products were run on an ABI Prism 377 DNA Sequencer, and analyzed using the BLAST alignment algorithm (Altschul et al., J. Mol. Biol. 215:403–410, ?). A novel clone (#43-43) was isolated by PCR with primers A and DVW on single-stranded cDNA from human embryonic palatal mesenchyme (HEPM or CRL1486) as a template. This clone was subsequently designated as a fragment of human aur1.

A lambda ZapII (Stratagene Cloning Systems, La Jolla, Calif.) cDNA library was constructed using mRNA from a pool of pancreatic carcinoma cell lines as a template for first strand cDNA synthesis. Phage were screened on nitrocellulose filters with the random primed $^{32}$P-labeled insert from p43-43 encoding human aur1 at 2×10$^6$ cpm/mL in hybridization buffer containing 6×SSC, 1× Denhardt's reagent, 0.1% SDS, with 0.1 mg/mL denatured, fragmented salmon sperm DNA. After overnight hybridization at 65° C., filters were washed in 0.1×SSC, 0.1% SDS at 65° C. Full length cDNA clones were sequenced on both strands using manual sequencing with T7 polymerase and oligonucleotide primers (Tabor et al., Proc. Natl. Acad. Sci. U.S.A. 84: 4767–4771, 1987).

Southern Blot Analysis

Genomic DNA was isolated from a variety of transformed human lines (CaCO$_2$, HTC15, LS147T, SKCO4, SW480, SW403, SW620, SW948, SW1417, SW1116, MCF7, BT474) using standard procedures (Maniatis et al. supra). Cells were trypsinized, washed with PBS and resuspended at ~10$^8$ cells/mL in Digestion buffer (100 mM NaCl, 10 mM Tris pH8, 25 mM EDTA, pH8, 0.5% SDS, 0.1 mg/mL proteinase K). Cells were lysed by incubation at 50° C. for 12 hours, followed by extraction with phenol/chloroform and precipitated with an equal volume of 7.5 M ammonium acetate and 100% EtOH. DNAs were resuspended in TE buffer. Approximately 20 $\mu$g genomic DNA was digested with HindIII or XhoII at 37° C. for at least 4 hours before fractionation on 1% agarose gels. The DNA fragments were transferred to nitrocellulose membranes by the capillary transfer method (Southern, J. Mol. Biol. 98:503-, 1975) and hybridized with human aur1 and aur2-specifc probes as described for Northern Blot analysis below. DNAs were restricted with HindIII since both aur1 and aur2 cDNAs contain a single site for this restriction enzyme.

Results:

In order to identify homologues of CCK4, a receptor that represents a distinct family of tyrosine kinases, degenerate primers to conserved sequences within kinase subdomains I and IX of ROS and the TRK-family of receptor tyrosine kinases were designed, since multiple alignments suggested CCK4 was most closely related these receptors. Subdomain I is at the N-terminus of the kinase domain and contains the consensus motif GXGXXGXV (SEQ ID NO:26) which is involved in anchoring ATP to the catalytic unit of all classes of kinases. Subdomain IX contains a nearly invariant Asp which acts to stabilize the catalytic loop by bonding to residues in subdomain VIB. Based on comparison of all known protein kinases, degenerate oligonucleotide primers to subdomains I and IX that would pick up only CCK4 and its chicken homologue KLG by PCR were designed.

Degenerate primers A and DVW were designed based on conserved residues within the kinase domain of CCK4, to use for identification of novel kinases using polymerase chain reaction (PCR). When applied to HEPM cell sscDNA as a template, multiple copies of CCK4 were isolated as well as a novel DNA fragment (43-43) of 567 bp with homology to other kinases. The novel sequence was most similar to Drosophila aurora kinase (GeneBank Accession #X83465) and the clone was designated human aur1.

The aur1 probe was used to screen a cDNA library constructed from human pancreatic cancer cell line mRNA to isolate overlapping clones spanning the complete open reading frame of aur1. Of multiple clones isolated, seven corresponded to human aur1. Two additional faintly hybridizing clones were also isolated during this screen and sequence analysis revealed they corresponded to a related, yet distinct kinase, which we designated human aur2.

Aur1 showed a single 4.3 kb band of equal intensity from all sources suggesting it is a single copy, non-rearranged gene in the multiple tumor types assayed. However, under low stringency conditions, it was possible to detect 1.3 kb and 3.2 kb SacI fragments which weakly hybridize to the aur1 probe. Aur2 showed bands at 7.0 kb and 4.3 kb and a faint higher molecular weight band at ~10 kb from all sources. These data suggest aur2 is also a single copy gene. The multiple bands seen on blots probed with aur2 are likely due to the fact that a full length cDNA probe was used.

The complete sequences of human aur1 and aur2 were determined from full length clones of each, isolated from the human pancreatic carcinoma library, from normal human duodenum, and from the partial human aur1 isolated from HEPM cells.

The 1,244 bp human aur1 nucleotide sequence is shown in SEQ ID NO:1 and contains a single open reading frame encoding a polypeptide of 344 amino acids. The AUR1 coding region is flanked by a 54 nucleotide 5'-untranslated region and a 132 nucleotide 3'-untranslated region ending with a poly(A) tail.

The 2,198 bp human aur2 nucleotide sequence is shown in SEQ ID NO:2 and contains a single open reading frame encoding a polypeptide of 403 amino acids. The AUR2 coding region is flanked by a 200 nucleotide 5'-untranslated region and a 768 nucleotide 3'-untranslated region.

The aur1 and aur2 cDNAs were sequenced from both a human pancreatic tumor and normal human duodenum, with no sequence differences observed except some probably polymorphic sites. These ambiguities include:

| cDNA | nucleotide | Comment |
| --- | --- | --- |
| aur1 | 1174 | one clone has poly A inserted |
|  | 873 | T in all duodenal clones, C in pancreatic tumor |
|  | 469 | T in one clone, C in all others |
|  | 848 | G in one clone, A in all others - changes amino acid E to G |
|  | 1097 | G in one clone, T in 2 others |
|  | 956 | G in one clone, A in 4 others |
|  | 29 | Splice to 103 in 5 clones, no splice (as shown in 5 clones |
| aur2 | 349 | T in 1 cline, C in multiple others (change amino acid P to L) |
|  | 369 | A in 3 clones, G in multiple others (change AA V to I) |

The C-terminal portions AUR1 and AUR2 conserve all 12 subdomains characterictic of eukaryotic protein kinases. The AUR1 and AUR2 kinase domains are proceded by a N-terminal domain of 74 and 130 amino acids, respectively. Comparison of the aur1 and aur2 nucleotide and deduced amino acid sequences (SEQ ID NO:3 or SEQ ID NO:4) with the available DNA and protein sequence databases indicated that they are unique with the exception of several EST sequences sharing high sequence identity. They do however have striking homology in both the N-terminal and catalytic domains with the drosophila aurora and *Saccharomyces cerevisiae* IPL1 genes. Futhermore, two unpublished database entries are likely to be close homologues from *Xenopus laevis* (p46APK—GB accession #Z17206 and p46BPK—GB accession #Z17207).

The N-terminal domains of aurora from human, frog, Drosophila, and yeast share limited sequence identity. Comparison of the catalytic domains of these proteins reveals AUR1 shares 70% amino acid identity with AUR2, 61% with the Drosophila aurora, and 45% with the yeast IPL1 gene. AUR2 kinase shares 60% amino acid identity with the Drosophila protein and 45% identity to yeast IPL1. Both AUR1 and AUR2 share less than 45% homology with all other known mammalian kinases (the closest being cAMP-dependent protein kinase A) suggesting they are homologues of these drosophila and yeast kinases.

AUR1 and AUR2 both contain a cAMP-dependent protein kinase phosphorylation site (THR232 of AUR1 and THR288 of AUR2) that is conserved in the drosophila and yeast homologues and is a known regulatory site in the cyclin-dependent kinase p34cdc2. AUR2 contains an additional PKA-site at SER342. Both proteins also have multiple Casein kinase II (five and six for AUR1 and AUR2) and protein kinase C (four and ten for AUR1 and AUR2) phosphorylation sites. AUR2 also has a single tyrosine phosphorylation consensus site at TYR334 that is also conserved with the Drosophila aurora, but is not present in AUR1 or yeast IPL1.

Natural mutants of the drosophila aurora AUR_dm and yeast IPL1 gene result in asymmetric nuclear division leading to chromosome missegregation, and atypical, monopolar spindles. This phenotype appears to result from a failure of centrosome separation. The associated microtubule architecture appear unaffected. Natural mutants in both drosophila and yeast target amino acid residues that are strictly conserved between human AUR1 and AUR2, further supporting they may be functional homologues. The corresponding residues in AUR1 that are found in natural mutants of AUR_dm or IPL1 are GLU125, THR232, PRO312, HIS324. All of these mutations are within the catalytic domain, and notably, one represents the conserved PKA-phosphorylation site. An additional mutation in AUR_dm at ASP47 is at a non-conserved residue in the N-terminal domain.

These findings suggest the catalytic activity may indeed play a central role in the biology of centrosome replication or segregation in lower organisms, and suggest that human AUR1 and AUR2 may play a complementary role in mammalian cells.

Example 2

AUR1 and AUR2 Expression in Human Tissues
Materials and Methods:
Northern Blot Analysis Northern blots containing 2 µg poly A+RNA per lane from 16 different adult human tissues (spleen, thymus, prostate, testis, ovary, small intestine, colonic mucosa, heart, brain, placenta, lung, liver, skeletal muscle, kidney, pancreas, and peripheral blood leukocytes), four different human fetal tissues (brain, lung, liver, and kidney), and 8 human cancer cell lines (HL60, HeLa, K-562, MOLT-4, Raji, SW480, and G361) on a charge-modified nylon membrane were obtained from Clontech (Palo Alto, Calif.). Additional Northern blots were prepared by running 10 µg total RNA isolated from human tumor cell lines on a denaturing formaldehyde 1.2% agarose gel and transferring to nylon membranes.

Filters were hybridized with random primed [$^{32}$P]dCTP-labeled probes synthesized from either the 527 bp insert from human aur1 clone 43—43 or the 1162 bp EcoRI fragment from pSG20, and either the 1 kb EcoRI fragment of human aur2 clone 11-1A or the 1257 bp BamHI-Not I fragment from pS621. Hybridization was performed at 60° C. overnight in 6×SSC, 0.1% SDS, 1×Denhardt's solution, 100 mg/mL denatured herring sperm DNA with 1–2×10$^6$ cpm/mL of $^{32}$P-labeled DNA probes. The filters were washed in 0.1×SSC/0.1% SDS, 65° C., and exposed overnight on Kodak XAR-2 film.

Semi-Quantitative PCR Detection of aur1

RNA was isolated from a variety of human cell lines, fresh frozen tissues, and primary tumors. Single stranded cDNA was synthesized from 10 mg of each RNA as described above using the Superscript Preamplification System (GibcoBRL). These single strand templates were then used in a 35 cycle PCR reaction with two aur1-specific oligonucleotides (3476: 5'-TTTGGCTCGGGAGAAGAAAAGCCAT-3' (SEQ ID NO:19), and 3506: 5'-CAATCATCTCTGGGGGCAGGTAGT-3') (SEQ ID NO:20). Reaction products were electrophoresed on 2% agarose gels, stained with ethidium bromide and photographed on a UV light box. The relative intensity of the ~475 bp aur1-specific bands were estimated for each sample.

Results:

A single aur1 mRNA transcript of approximately 1.4 kb was identified, and was found to be most abundant in the thymus and small intestine with weak signals from testis, ovary, colon, placenta, and spleen. Prostate and peripheral blood lymphocytes were negative. Human fetal liver and kidney were also positive, with a weaker signal in fetal lung and no expression in fetal brain (Table).

A similar analysis of human aur2 expression showed a more restricted expression profile. A single 2.4 kb aur2 transcript was detected strongly in the adult testis and thymus, and weakly in heart, placenta, skeletal muscles and in fetal liver and kidney whereas the other normal tissue sources were negative (see Table).

The aur1 mRNA expression profile in several primary tumors and multiple cell lines of diverse neoplastic origin were determined by Northern analysis and by the semi-quantitative PCR assay using primers from sequences in the aur1 kinase domain. The results are included in the Table. Aur1 transcripts were detected in every tumor line assayed with the highest expression in several human colon cancer cell lines (SW480, Colo320, SW620, SW1417, Caco2, SW12417) and in lung carcinoma (Calu3), breast carcinoma (T47D, MCF7), Melanoma (A375), Kidney carcinoma (CaKi-1, CaKi-2), liver carcinoma (SK-HEP-1), and neural tumors (SF767, T98G). Lesser expression of aur1 was seen in other colon carcinomas (HTC15, T84, SW948, SW1116, HT29), neural tumors (Daoy), Ovarian carcinoma (Ovcar3, Primary tumor), pancreatic carcinoma (HS766T), and a primary kidney tumor.

The aur2 expression profile in tumor cell lines was strikingly more restricted than that of aur1. Strong expression of aur2 was detected only in colon carcinoma cell lines (Caco2, SW480, SW1417, SW620) whereas weak signals were seen in other colon (HTC15, Colo320), Breast (T47D, MCF7) and lung (Calu3) tumor cell lines. Several other tumor lines had no detectable aur2 transcripts.

AUR1 and AUR2 NORTHERN ANALYSIS IN HUMAN NORMAL TISSUE AND CANCER CELLSS

| Cell type | Origin | AUR 1 | AUR 2 |
|---|---|---|---|
| Thymus | Normal tissue | 5 | 4 |
| Fetal liver | Normal tissue | 4 | 2 |
| Fetal kidney | Normal tissue | 4 | 1 |
| Lung | Normal tissue | 3 | 0 |
| Duodenum | Normal tissue | 2 | 1 |
| Colon | Normal tissue | 2 | 0 |
| Fetal lung | Normal tissue | 2 | 0 |
| Ovary | Normal tissue | 2 | 0 |
| Testis | Normal tissue | 2 | 2 |
| Brain | Normal tissue | 0 | 0 |
| Cerebellum | Normal tissue | 0 | 0 |
| Salivary gland | Normal tissue | 0 | 0 |
| Heart | Normal tissue | 0 | 0 |
| Liver | Normal tissue | 0 | 0 |
| Pancreas | Normal tissue | 0 | 0 |
| Kidney | Normal tissue | 0 | 0 |
| Spleen | Normal tissue | 0 | 0 |
| Stomach | Normal tissue | 0 | 0 |
| Uterus | Normal tissue | 0 | 0 |
| Prostate | Normal tissue | 0 | 0 |
| Skeletal muscle | Normal tissue | 0 | 0 |
| Fetal brain | Normal tissue | 0 | 0 |
| PBLs | Normal tissue | 0 | 0 |
| Salivary gland | Normal tissue | 0 | 0 |
| Placenta | Normal tissue | 0 | 0 |
| SF-268 | CNS tumor | 4 | ND |
| CCRF-CEM | Leukemia | 4 | ND |
| K-562 | Leukemia | 4 | ND |
| HCC-2998 | Colon tumor | 4 | ND |
| SW620 | Colon tumor | 4 | 2 |
| KM-12 | Leukemia | 4 | ND |
| MCF7/ADR-RES | Breast tumor | 4 | 2 |
| MDA-N | Breast tumor | 4 | ND |
| BT-549 | Breast tumor | 4 | ND |
| SW480 | Colon tumor | 4 | 4 |
| SW48 | Colon tumor | 4 | ND |
| Calu-3 | Lung tumor | 4 | ND |
| Calu3 | Lung tumor | 4 | 2 |
| T47D | Breast tumor | 4 | 2 |
| A375 | Melanoma | 4 | 0 |
| SF767 | CNS tumor | 4 | 0 |
| SW1417 | Colon tumor | 4 | 4 |
| CaKi2 | Kidney tumor | 4 | 0 |
| CaKi1 | Kidney tumor | 4 | 0 |
| Caco2 | Colon tumor | 4 | 4 |

-continued

AUR1 and AUR2 NORTHERN ANALYSIS IN HUMAN NORMAL TISSUE AND CANCER CELLSS

| Cell type | Origin | AUR 1 | AUR 2 |
|---|---|---|---|
| SW1417 | Colon tumor | 4 | 0 |
| T98G | CNS tumor | 4 | 0 |
| SF-539 | CNS tumor | 3 | ND |
| SK-MEL-2 | Melanoma | 3 | ND |
| SK-MEL-5 | Melanoma | 3 | ND |
| R-48 | Gastric tumor | 3 | ND |
| RF-1 | Gastric tumor | 3 | ND |
| SW948 | Colon tumor | 3 | ND |
| AGS | Gastric tumor | 3 | ND |
| HFL1 | Normal lung | 3 | ND |
| OVCAR-8 | Ovarian tumor | 2 | ND |
| HT-29 | Colon tumor | 2 | ND |
| MDA-MB-231 | Breast tumor | 2 | ND |
| MDA-MB-435 | Breast tumor | 2 | ND |
| SK-MEL-5 | Melanoma | 2 | ND |
| Kato-3 | Gastric tumor | 2 | ND |
| Colo 205 | Colon tumor | 2 | ND |
| Colo 320DM | Colon tumor | 2 | 2 |
| WiDr | Colon tumor | 2 | ND |
| HT-29 | Colon tumor | 2 | ND |
| SNU-C2B | Colon tumor | 2 | ND |
| HTC15 | Colon tumor | 2 | 2 |
| T84 | Colon tumor | 2 | 0 |
| SW948 | Colon tumor | 2 | 0 |
| Daoy | CNS tumor | 2 | 0 |
| OVCAR3 | Ovary tumor | 2 | 0 |
| HS766T | Pancreas tumor | 2 | 0 |
| SW1116 | Colon tumor | 2 | 0 |
| Wilms tumor | Kidney tumor | 2 | 0 |
| UO-31 | Renal tumor | 0 | ND |

Example 3

Recombinant Expression of Aur1 and Aur2

Materials and Methods:

Expression Vector Construction

Expression constructs were generated by PCR-assisted mutagenesis in which the entire coding domains of aur1 and aur2 were tagged on their carboxy-terminal ends with the hemophilus influenza hemaglutinin (HA) epitope YPYDVP-DYAS (SEQ ID NO:21)(Pati, Gene 114:285–288, 1992). These constructs were introduced into two mammalian expression vectors: pLXSN (Miller et al., Biotechniques 7:980–988, 1989) for the generation of virus producing lines; and pRK5 for transient expression analysis. Inserts were designed to be flanked by unique BamHI and NotI sites and were cloned directly into pLXSN or pRK5 at the 5'-BamHI and 3'-NotI sites.

The BamHI-NotI full length aur1 and aur2 constructs were also ligated into pRS316 (Liu et al, Genetics 132:665–673, 1992). This vector contains a galactose-inducible promoter in a centromeric shuttle vector for expression in Saccharomyces cerevisiae. These are to assess if the human genes can complement the related temperature sensitive yeast IPL1 mutant, which is closely related to aur1. In addition, fusion constructs containing the N-terminal domain of yeast IPL1 fused to the C-terminal kinase domains of aur1 and aur2 were generated. These were produced by insertion of an artificial ClaI site at the 5' end of the kinase domains of the kinases, at the conserved Asp-Asp-Phe-Glu sequence.

Dominant negative aur1 and aur2 constructs were also made in both pLXSN and pRK5 by mutation of the invariant Lys (amino acid positions 106 and 162 in AUR1 and AUR2, respectively) to an Met by PCR mutagenesis. The constructs are termed AUR1KM and AUR2KM. Constitutively active forms of AUR1 and AUR2 were generated by mutation of the DNA heading the encoding the phosphorylation site (232 and 288) to an Asp resulting in AUR1TD and AUR2TD.

Expression constructs in both pLXSN and pRK5 were also made containing just the N-terminal, non-catalytic domain of AUR1 and AUR2. These were generated by PCR from the parental constructs and contain the N-terminal 77 amino acids of AUR1 and 132 amino acids of AUR2.

The entire aur1 and aur2 open reading frames (no HA-tag) excluding the initiating methionines were generated by PCR and ligated into pGEX vector for bacterial production of GST-fusion proteins for immunization of rabbits for antibody production.

Generation of Virus Producing AUR Cell Lines

To generate high-titer virus stocks, pLXSN recombinant constructs containing either aur1 or aur2 genes were transfected into an amphotropic helper cell line PA317 using $CaCl_2$-mediated transfection. After selection on G418, the cells were plated on normal media without G418 (500 µg/mL). Supernatants from resistant cells were used to infect the ecotropic helper cell line GP+E86, and cells again selected on G418. Resistant cells were again taken off G418, and the supernatants harvested every 8–12 hours and pooled as virus stock (Redemann et al., Mol. Cell. Biol. 12, 491–498, 1992). Viral stock titers were typically ~$10^6$/mL.

Retroviral Infection of NIH-3T3 Cells with Aur1 and/or Aur2

NIH-3T3, and BALB/3T3 cells were grown in 100 mm plates with DMEM (Gibco) containing 10% fetal calf serum (FCS). The cells were superinfected with the aur1 and aur2 retrovirus by adding approximately 3 mL viral supernatant to 15 mL culture media for approximately 24 hours. Cells expressing the retroviral constructs were then selected by growth in DMEM/10% FCS supplemented with 500 µg/mL G418.

Transient Expression of Aur1 and/or Aur2 in Mammalian Cells

The pRK5 expression plasmids (10 µg DNA/100 mm plate) containing the HA-tagged aur1 and aur2 genes were introduced into COS and 293 cells with lipofectamine (Gibco BRL). After 72 hours, the cells were harvested in 0.5 mL solubilization buffer (20 mM HEPES pH7.35, 150 mM NaCl, 10% glycerol, 1% Triton X-100, 1.5 mM $MgCl_2$, 1 mM EGTA, 2 mM phenylmethylsulfonyl fluoride, 1 µg/mL aprotinin).

Sample aliquots were resolved by SDS polyacrylamide gel electrophoresis (PAGE) on 15% acrylamide/0.5% bis-acrylamide gels and electrophoretically transferred to nitrocellulose. Non-specific binding was blocked by preincubating blots in Blotto (phosphate buffered saline containing 5% w/v non-fat dried milk and 0.2% v/v nonidet P-40 (Sigma)), and recombinant protein was detected using a murine Mab to the HA decapeptide tag. Alternatively, recombinant protein can be detected using various AUR1- or AUR2-specific antisera.

Results:

Recombinant AUR1 and AUR2 expressed in COS cells migrated with apparent Mr of 39,000 and 46,000, consistent with their predicted molecular weights of 39264 and 46730 based on their primary amino acid sequence. This analysis confirms that the recombinant protein can be stably produced in mammalian cells.

Dominant negative and constitutively active forms of AUR1 and AUR2 will be usefull for delineating biologic consequences of either oblation or overexpression of these putative serine/threonine kinases. Initial studies with altered DNA constructs demonstrates that injust 2 hours following infection of NIH3T3 or BALB/3T3 cells with aur1 or aur2 retroviral stocks, cells become multinucleated. This phenotype persisted such that 2 days after infection some cells were found to have as many as 20 nuclei. The multinucleated cells typically had increased cytoplasm and diffuse cell boundaries. Immunostaining with both actin and DAPI, confirmed these nuclei were all contained within a single cell, and that the actin cytoskeleton was apparently normal.

Example 4

Generation of AUR-Specific Immunoreagents

Material and Methods:

AUR-specific immunoreagents were raised in rabbits against KLH-conjugated synthetic peptides corresponding to either the N-terminal region of AUR2 ($^{104}$SAPENNPEEQLASK$^{117}$) (SEQ ID NO:22) and ($^{90}$RPLNNTQKSKQPL$^{102}$) (SEQ ID NO:23) or the N-terminus or N-terminal domain of human AUR1 ($^{1}$MAQKENSYPWPYG$^{13}$) (SEQ ID NO:24) and ($^{53}$PGQKVMENSSGTP$^{65}$) (SEQ ID NO:25). Additional immunoreagents were generated by immunizing rabbits with the bacterially expressed full length AUR1 and AUR2 GST-fusion proteins.

Results:

Specific immunoreagents were generated in rabbits against peptide sequence from the N-terminal domains of AUR1 and AUR2 to localize expression of endogenous and recombinant AUR within cells. These reagents can also be used to identify substrates for the AURs.

Example 5

Myelin Basic Protein is an Artificial Substrate for AUR1 and AUR2 Kinase

Method:

Human colorectal adenocarcinoma SW480 cells were cultured in RPMI 1640 plus 10% fetal bovine serum, L-glutamine, penicillin and streptomycin. Confluent cultures of SW480 cells were washed three times with ice cold phosphate buffered saline (PBS) and then were scraped into 1 mL of ice cold PBS. The cells were centrifuged at 1,000 rpm at 4° C., the PBS aspirated away, and the resulting cell pellet stored at −80° C. The pellets from three 15 cm plates were thawed on ice and resuspended in a total of 1 mL of kinase lysis buffer 50 mM HEPES pH 7.4, 100 mM KCl, 25 mM NaF, 1 mM NaVO$_3$, 0.5% NP40, 1 mM DTT, 2 µg/mL aprotinin, and 1 µg/mL leupeptin) and were rotated gently for 20 minutes at 4° C. The samples were then centrifuged at 10,000×g for 10 minutes at 4° C. and the resulting supernatant was transferred to a clean 1.5 mL centrifuge tube and stored or kept on ice. The protein concentration was determined by Bradford analysis. One milligram of total protein was pre-cleared with 10 µL of protein A-Sepharose (Boehringer) for 15 minutes at 4° C. followed by the addition of 2 µL of either rabbit pre-immune serum, affinity purified AUR1 peptide antisera, affinity purified AUR1 peptide antisera plus 6 µg of competing AUR1 peptide, affinity purified AUR2 peptide antisera, or, affinity purified AUR2 peptide antisera plus 6 µg of competing AUR2 peptide and incubated for 30 minutes at 4° C.

Subsequently, 10 µL of protein A-sepharose was added and the incubation was continued for an additional 45 minutes at 4° C. The tubes were briefly centrifuged to pellet the antibody-protein A-sepharose complex and the resulting supernatant was aspirated off. The antibody-protein A-sepharose pellet was washed twice with 0.5 mL of kinase lysis buffer followed by a wash with 0.5 mL of kinase buffer (20 mM HEPES pH 7.4, 125 mM KCl, 10 mM MgCl$_2$, 1 mM NaF, 1 mM NaVO$_3$, and 1 mM DTT). The antibody-protein A-sepharose pellet was resuspended in 20 µL of kinase buffer containing 5 µCi of [γ-$^{32}$P] ATP and 0.5 mg/mL myelin basic protein (Sigma), incubated for 20 minutes at 37° C. after which 10 µL of protein sample buffer 200 mM Tris-Cl pH 6.8, 40% glycerol, 730 mM B-mercaptoethanol, 0.4% SDS, and 0.05% Bromophenol Blue) was added. The tubes were mixed well and incubated for 5 minutes at 100° C. The samples were resolved on an 18% SDS polyacrylamide gel and visualized by autoradiography.

Results:

AUR1 and AUR2 immunocomplexes were able to phosphorylate myelin basic protein. When competing peptide was used in the immunoprecipitations neither AUR1 nor AUR2 antsera immunocomplexes were able to phosphorylate myelin basic protein more than the pre-immune sera control. This suggests that the kinase activity observed is due to AUR1 and AUR2 and not to other proteins present in the immunocomplex.

This observation will allow for the purification of active AUR1 and AUR2 kinase by using myelin basic protein as a substrate to follow kinase activity. It also will allow the development of an in vitro kinase assay using recombinant AUR1 and AUR2 proteins. Furthermore an AUR1 and AUR2 in vitro kinase assay will allow one to screen small molecule collections for inhibitors of the AUR1 and AUR2 kinases by measuring the inhibition of phosphorylation of myelin basic protein.

Example 6

Structural Comparison of Aur Homologues

Materials and Methods:

cDNA cloning

Degenerate oligonucleotide primers were designed for PCR cloning based on kinase domains I and IX of CCK4 (GenBank:U33635; Cowley et al., Cell 77:841–852, 1994), a receptor tyrosine kinase expressed in a wide range of normal and transformed epithelial cells. The sense primer was 5'-GARTTYGGNGARGTNTTYYTNGC-3' (SEQ ID NO:16), encoding the amino acids EFGEVFLA (SEQ ID NO:18) and the antisense primer was 5'-AGNACNCCRAANGCCCACACRTC-3' (SEQ ID NO:17), encoding the complementary strand of amino acids DVWAFGVL (SEQ ID NO:33). These primers were applied to sscDNA generated from RNA isolated from several colon cancer cell lines as well as other tumor sources. PCR products of 500–600 bp were subcloned and sequenced, revealing a fragment related to Drosophila aurora. This fragment was used to probe a lambda library constructed from a pool of several human pancreatic cancer cell line RNAs, leading to isolation of full length clones for human aur1. Two weakly hybridizing clones were also isolated and sequence analysis revealed that they represented a related but distinct cDNA termed aur2. Full length clones were also isolated for both genes from normal human duodenum cDNA. All clones were sequenced on both strands with internal oligonucleotide primers using both T7 polymerase manual sequencing and using dye-terminator cycle sequencing with AmpliTaq DNA polymerase on an ABI Prism 377. The complete aur2 coding sequence was also confirmed from 10 primary colorectal tumor samples. Primers 5'-CGCCTTTGCATCCGCTCCTG-3' (SEQ ID NO:34) and 5'-GATTTGCCTCCTGTGAAGAC-3' (SEQ ID NO:35) were used in an RT-PCR reaction with sscDNA generated from the tumor RNAs. The PCR products were purified by GeneClean and sequenced directly by dye-terminator cycle sequencing with several oligonucleotide primers. While no sequence differences were observed between clones isolated from normal or tumor sources, a single nucleotide polymorphism was identified in 2 of the tumor samples which would encode an F to I change at residue 31. Abbreviations for degenerate nucleotide residues are: R=A or G; Y=C or T; N=A, C, G or T.

Results:

A PCR-based screen was initiated to identify novel colon cancer associated kinases. One of these clones encoded a protein with homology to the aurora protein kinase from *Drosophila melanogaster* and the IPL1 kinase from *Saccharomyces cerevisiae* (Francisco et al., Mol. Cell. Biol. 14:4731–4740, 1994; Glover et al., Cell 81:95–105, 1995). While using this fragment to screen for a full length cDNA clone, a weakly hybridizing clone was found to encode a related kinase. These genes are referred to as aur1 and aur2, to reflect their homology to each other and to the *Drosophila aurora* kinase.

Aur1 cDNA contained a 1032 bp open reading frame that encodes a 344 amino acid polypeptide with a predicted molecular mass of 39.3 kDa. The aur2 cDNA contained a 1209 bp open reading frame that encodes a 403 amino acid polypeptide with a predicted molecular mass of 45.8 kDa. Two additional human aur pseudogenes were also identified as expressed transcripts that are each contained on single exons and maintain striking DNA homology to either aur1 or aur2, yet exhibit multiple frame shifts.

A partial sequence of BTAK (Sen et al., Oncogene 14:2195–2200, 1997), a breast tumor associated kinase, has been reported that appears to be fragment of human aur2. A second manuscript reports the sequence of human aik (Kimura et al., J. Biol. Chem. 272:13766–13771, 1997), a cell cycle-regulated protein localized to spindle pole bodies, which shares 92% amino acid sequence identity with human AUR2 but is likely identical except for the incorporation of 6 frameshifts resulting from sequencing errors. A third paper provides the sequence of AYK1 (Yanai et al. Oncogene 14:2943–2950, 1997), a meiotic regulated gene, that appears to be the murine orthologue of AUR2. The present invention describes the first complete sequence for both human aur1 and aur2.

The deduced amino acid sequences of human aur1 and aur2 are presented in FIG. 1 aligned with the yeast and Drosophila homologues IPL1 and aurora. Human AUR2 protein shares 57%, 43%, and 41% identity over its entire length with human AUR1, Drosophila aurora, and IPL1, respectively. The four sequences contain a C-terminal domain with all the characteristic motifs of a serine/threonine kinase. The kinase domain of human AUR2 shares 74%, 62%, and 49% amino acid identity with human AUR1, Drosophila aurora, and IPL1 and 83.5% identity with two amphibian homologues present in Xenopus [p46Eg22 (PIR:S53342) and p46Eg265 (PIR:S53343)]. The Drosophila aurora is most related to human AUR1 whereas the yeast IPL1 is most related to AUR2. This structural assessment is supported by complementation studies in yeast where only the human AUR2 kinase can complement an IPL1 mutant. Whereas a single aurora-like kinase is present in yeast, at least two members are present in *C. elegans* (GB:U53336, gene K07C11.2 and GB:U97196, gene B0207.4). The deduced catalytic domains of these *C. elegans* proteins share 55% and 64% amino acid sequence identity to the human AUR2 kinase domain. We predict an additional aurora homologue will ultimately be identified in Drosophila as characterization of its genome nears completion.

The 129 and 73 amino acid N-terminal domains of human AUR2 and AUR1 share limited homology with each other and with the analogous 160 and 100 amino acid domains of Drosophila aurora and yeast IPL1. The N-terminal regions of human and mouse AUR2 share 54% identity to each other and 28–30% identity to the two Xenopus proteins, and together help define two distantly conserved motifs present in the non-catalytic region of all auroras (FIG. 1). The first motif includes 10 amino stretch, $KENX_4PVK$, termed AUR Box1 and the second motif is centered around a 15 amino acid stretch, $QX_9AQRVL$, termed AUR Box 2 (see overlines in FIG. 1). The Drosophila aurora has a 36 amino acid insert in AUR Box2. Several potential serine and threonine phosphorylation sites are also conserved among these proteins including a protein kinase A phosphorylation motif RRXT in the activation loop of the kinase. A temperature sensitive mutant of the yeast IPL1 gene consists of a Thr to Ala substitution within the activation loop (Gopalan et al., J. Cell Biol. 138:643–656, 1997), suggesting that phosphorylation at this site may be biologically relevant. Additional mutants in the yeast (Chan 1993, supra) and Drosophila (Glover 1995, supra) homologues of aurora have been mapped exclusively to the kinase domain, except for a single Drosophila mutant (Glover 1995, supra) that involves a mutation at Asp47 within the N-terminal AUR Box2. Since these mutations result in abnormal nuclei, chromosome missegregation, and monopolar spindles, these findings suggest that the catalytic activity of the auroras may play an important role in centrosome biology.

Example 7

Expression of Aur1 and Aur2 RNA in Normal Tissues and Tumor Cell Lines

Materials and Methods:

Northern Blots

Cell pellets from cultured tumor cell lines were provided by Nick Scuidero (Developmental Therapeutics Program, NCI), and are part of the NCI tumor panel (see website listing at http://epnwsl.ncifcrf.gov:2345/dis3d/cancer_screen/celllist.html). Normal human tissue samples were obtained from the Cooperative Human Tissue Network (Cleveland, Ohio). Human colorectal tissue samples for Northern and Southern analysis were obtained from Los Angeles area hospitals including UCLA-Harbor, Wadsworth and Cedars Sinai from 1988 to 1997. Tumor histology was confirmed prior to preparing RNA, DNA and protein lysates from each sample. Total cell or tissue RNA was isolated using the guanidine salts/phenol extraction protocol of Chomczynski and Sacchi (Wolf et al., Oncogene 14:543–549, 1997). Northern blotting was performed using standard techniques (Mossie et al. Oncogene 11:2179–2184, 1995) with a random-labeled 586 bp BamHI-SspI fragment of the human aur2 cDNA. A multiple tissue Northern blot and a human immune system blot (Clontech) containing 2 g polyA$^+$ mRNA per lane were also probed for aur2 expression. A human b-actincDNA probe (Clontech) was used to confirm equivalent loading of intact RNA. RNA (10 g) from the SK-HEP-1 (HTB52) liver adenocarcinoma cell line served as an internal standard for detection of aur2 expression on each blot. Blots were quantitated using a phosphorimager and ImageQuant software (Molecular Dynamics, Mountain View, Calif.).

Results:

Northern blot analysis of mRNA isolated from normal adult human tissues demonstrates that aur2 expression is primarily restricted to testis, thymus and fetal liver, with very weak expression in bone marrow, lymph node, and spleen and no detectable expression in all other adult tissues examined. Additional studies demonstrate tight temporal regulation of these transcripts during mitosis (and Kimura 1997, supra).

Human aur1 was also expressed at highest levels in normal testis and thymus, with a moderate level of expression in lung and small intestine.

Since these genes were originally identified from human tumors, we performed Northern blot analysis with aur2 on a panel of human tumor cell lines of colon, renal, melanoma, and breast origin. The 2.4 kb aur2 transcript was expressed in 96% (24 of 25) of these transformed cell lines, with the only exception being the UO-31 renal carcinoma cell line. The 1.4 kb aur1 transcript was co-expressed at surprisingly similar levels as aur2 in the same 24 tumor cell lines.

Example 8

Amplification and Overexpression of Aur2 in Primary Human Colorectal Cancers

Materials and Methods:

Chromosomal Localization

The Stanford G3 radiation hybrid panel was obtained from Research Genetics (Huntsville, Ala.). Primers used for radiation hybrid mapping were: 5'-ATGCCTCCGGAAAGAGCCTGT-3' (SEQ ID NO:36) and 5'-GTGTCCCACTGCTATTCTCCAT-3' (SEQ ID NO:37) for aur1 and 5'-CAGGGCTGCCATATAACCTGA-3' (SEQ ID NO:38) and 5'-CTAGCACAGGCTGACGGGGC-3' (SEQ ID NO:39) for aur2. The aur1 primers are directed to the N-terminal region of the gene and generate a 247 bp fragment following 25 cycle PCR with a 54° C. annealing temperature. The aur2 primers amplify a 255 bp fragment from the 3' UTR following a 25 cycle PCR with a 54° C. annealing temperature. The raw score for aur1 against the SHGCR G3 panel is: 00000000000010000000000000000000000000010000000 1001001000000000001000000000001010101, and for aur2: 10000000001000101000000100010010000000000010000 0011000010010010100001 0010010010010.

Southern Blotting

Genomic DNA was isolated from the human colorectal tissue samples by standard methods (Proteinase K digestion, phenol:chloroform extraction, and ethanol precipitation). Southern blots were prepared by digesting 5 μg of DNA with PstI, separating the fragments on 1% agarose gels, blotting onto nylon membranes (Nytran-Plus, Schleicher & Schuell), and probing sequentially with a random primer labeled 1044 bp aur2 cDNA fragment (pSG19) and a 1700 bp cloned fragment of the CYP24 gene (pKS-h24, from J. Omdahl, U. of New Mexico). A probe for human β-globin was used to confirm equivalent sample loading. Final washes were at 0.1×SSC, 0.1% SDS, 60° C. Autoradiographs were quantitated relative to β-globin using ImageQuant software (Molecular Dynamics, Mountain View, Calif.).

Results:

Aur2 expression was next characterized by Northern blot analysis in a panel of 41 primary human colorectal tumors and matched normal colorectal tissue from the same patients. Approximately 54% (22/41) of the samples showed increased expression of the 2.4 kb aur2 transcript in the tumor as compared to the normal colon control. Aur2 RNA showed 4–28 fold overexpression in tumor versus normal tissue.

The aur1 and aur2 genes were mapped using the Stanford Human Genome Center G3 radiation hybrid panel. Human aur1 is located on chromosome 17p13.1 (LOD score of 9.555 to linked marker SHGC-35513) and human aur2 on chromosome 20q13.2 (LOD score of 17.26 to linked marker SHGC-3245). Mapping was also confirmed by hybridization to a human-rodent somatic cell hybrid panel (Coriell Cell Repository, Camden, N.J.). Aur2 maps adjacent to the vitamin D hydroxylase (CYP24) gene and the cosmid probe RMC20C001 that lie at 0.825–0.83 Flpter (fractional length from pter) on chromosome 20 (Tanner 1994, supra; Tanner 1996, supra). Both of these markers have been characterized for their presence in the 20q13 amplicon common to many human malignancies, particularly those from breast, bladder, and colon cancers.

Southern blot hybridization was performed using an aur2 cDNA probe along with a control probe for the CYP24 gene that serves as a marker of the amplicon (Tanner 1994, supra; Tanner 1996, supra). The aur2 probe hybridized to PstI fragments of 5.8, 3.7, 3.3, 2.8, 2.5, and 1.3 kb. The 5.8, 3.3, 2.8, and 2.5 kb bands are specific to aur2. Only the aur2-specific bands showed amplification in the tumor samples.

Aur2 DNA was amplified in 41 of 79 (52%) of the primary colorectal tumors for which suitable DNA was available for genotyping. Nine of twelve samples demonstrated a 2–8 fold amplification of aur2 DNA in the tumors compared to normal tissue. One of the samples demonstrates RNA overexpression in the absence of DNA amplification, whereas the other eleven show a direct correlation between DNA amplification and RNA overexpression. The CYP24 gene was found to be co-amplified with aur2 in 37 of 41 (90%) matched pairs, and was only once found to be amplified in the absence of aur2 amplification.

There is a high correlation ($\rho=0.695$) between aur2 DNA amplification and RNA overexpression with only one discordant result. In the single case of aur2 DNA amplification in the absence of RNA overexpression, aur2 RNA was actually elevated in both the normal and tumor specimens, compared to other tumor-normal pairs. Conceivably, high expression of aur2 RNA in this normal colon sample may represent an early predisposing lesion. Conversely, five paired samples showed increased RNA expression in the absence of DNA amplification, possibly due to transcriptional activation. If these five pairs are excluded from the analysis, the correlation between aur2 DNA amplification and RNA overexpression increases to $\rho=0.939$. These data suggest that DNA amplification is a mechanism for AUR2 activation and also implicates aur2 as an oncogene at 20q13 whose high level amplification correlates with poor clinical outcome in breast cancer (Isola 1995, supra).

To determine if the aur2 sequence from the 20q13 amplicon was the same as that from normal sources, we performed direct sequencing of RT-PCR products encompassing the complete aur2 coding region from 10 primary colorectal tumor samples. Eight samples, including both normal and amplified levels of the 20q13 amplicon, confirmed the aur2 sequence. A single nucleotide polymorphism was identified in 2 samples resulting in a phenylalanine to isoleucine change at residue 31 in the N-terminal Aurora Box1 (circled in FIG. 1). This analysis demonstrates that the 20q13 amplicon typically contains increased copies of the intact, unmutated aur2 coding region.

Example 9

Detection of AUR2 Protein in Primary Human Colon Cancer Samples

Materials and Methods:

Western Blotting

Matched human tissue samples from primary colorectal carcinomas and adjacent normal tissue were obtained from the Cooperative Human Tissue Network (Cleveland, Ohio)

and Pathology Associates International (Frederick, Md.). Thirty micron cryostat sections of OCT embedded tissue was lysed directly in 25 μL of ice-cold RIPA buffer (50 mM Tris-Cl, pH 8.0, 150 mM NaCl, 1.0% NP-40, 0.5% deoxycholate, 0. 1% SDS, 1 mM DTT, and protease inhibitors) by gentle mixing on ice for 20 minutes. The lysate was then spun for 10 minutes at 10,000×g in a microfuge at 4° C. The resulting supernatant was transferred to a clean tube and the total protein concentration was determined by Bradford analysis. Equal amounts of total protein from the matched samples was resolved on a 12% polyacrylamide gel, transferred to a nylon membrane (BioRad), and probed with a 1:2,000 dilution of affinity purified antibodies to AUR2. The immunoblot was developed with ECL reagent (Amersham). Lysates from tumor cell lines were prepared and analysed as described above.
Results:

To analyze AUR2 protein expression, we generated polyclonal antibodies in rabbits against the entire open reading frame expressed in E. coli as a GST-fusion protein. The anti-AUR2 antibodies were used to probe blots of protein lysates made from cryostat sections of primary human colon carcinomas or from adjacent normal tissue. The AUR2 antibodies detect a protein of approximately 46 kDa in two primary human colon carcinomas, but not in samples derived from the adjacent normal tissue. These antibodies also detect overexpression of AUR2 protein in various cultured tumor cell lines derived from colorectal carcinomas.

Example 10

Aur2 Transforms Rat1 Fibroblasts

Materials and Methods:

Expression Constructs

HA-tagged[42] versions of wild-type, kinase dead (K162M), and activated (T288D) aur2 were subcloned into the expression vector pLXSN. These contructs were transfected into the amphotropic packaging cell line PA317 and the supernatants were harvested and used to infect the producer cell line GP+E-86 (Markowitz et al, Virology 167:400–406, 1988). Neomycin resistant clones were selected and assayed for AUR2 protein expression. Supernatants from the positive producer cell lines were used to infect Rat1 and NIH3T3 cells. Stable clones were selected for in the presence of neomycin and assayed for AUR2 protein expression by immunoblotinG.

In vitro Kinase Assays

Rat1 and NIH3T3 cells expressing the appropriate aur2 construct were solubilized in kinase lysis buffer (50 mM Hepes, pH 7.4, 100 mM KCl, 25 mM NaF, 0.5% NP-40, 1 mM NaVO$_3$, 1 mM DTT, and protease inhibitors) for 15 minutes on ice, spun in a microfuge at 10,000×g for 10 minutes at 4° C. The resulting supernatant was transferred to a clean tube and the total protein concentration was determined by Bradford analysis. Equal amounts of protein (usually 2 mg) were immunoprecipitated with the anti-HA monoclonal antibody 12CA (Boehinger). The immune complexes were washed three times with kinase lysis buffer followed and were either resuspended in 1×Laemmli SDS sample buffer or washed three times with kinase buffer (without γ-$^{32}$P-ATP and α-casein) and resuspended in 30 μL of 1×kinase buffer (20 mM Hepes, pH 7.4,150 mM KCl, 5 mM MnCl$_2$, 5 mM NaF, 1 mM DTT, 50 μM ATP, 20 μCi γ-$^{32}$P-ATP, and 0.5 mg/mL α-casein). In vitro kinase reactions were carried out for 20 minutes at 37° C. and stopped by the addition of 30 μL of 2× Laemmli SDS sample buffer. Samples were incubated for 5 minutes at 95° C. and resolved on 14% SDS-polyacrylamide gels.

Soft Agar Assays

A 3% solution of agar (at 56° C.) was diluted to a final concentration of 0.6% with growth medium (at 56° C.), pipetted into tissue culture dishes, and allowed to solidify at room temperature for 20–30 minutes. At this time, 2×10$^5$ cells in a volume of 50 μL were mixed with 0.3% agar (diluted with growth media at 40° C.), pipetted gently onto the bottom agar layer, and allowed to solidify for 20–25 minutes at room temperature. Once solidified, the plates were incubated at 37° C. in a 5% CO$_2$ atmosphere. Fresh top agar was added once a week. After 4 weeks the plates were stained with neutral red.
Results:

If aur2 is a relevant target on the 20q13 amplicon, one might expect that overexpression of aur2 would be transforming. To examine this question, we established stable Rat1 cell lines that express human aur2. Rat1 cells were infected with retroviruses that express a hemagglutinin (HA)-tagged (Pati 1992, supra) wild-type aur2 or a kinase inactive mutant where the essential lysine at residue 162 (FIG. 1) was changed to a methionine (K162M). In addition, an activating mutation was made in which the threonine at residue 288 (FIG. 1) in the activation loop was changed to an aspartic acid (T288D). This mutation was designed to mimic constitutive phosphorylation at this site and indeed activates the kinase in vitro. The stable Rat1 lines expressed similar amounts of AUR2 protein. In vitro kinase assays were performed using the AUR2 protein produced by the stable cell lines. The kinase inactive AUR2 mutant (K162M) was unable to phosphorylate-casein over the levels observed in the vector control cell line in vitro, whereas the wild-type and activated AUR2 (T288D) proteins had increased activity on this artificial substrate.

To characterize the transforming potential of aur2, we performed soft agar assays with the Rat1 clones. The vector control, K162M, wild-type, and T288D AUR2 expressing Rat1 cells were plated in soft agar and scored for growth after 4 weeks. Cells expressing the wild-type and the T288D AUR2 formed colonies in soft agar, in contrast to the lack of growth by cells expressing the kinase inactive AUR2. Ten of thirteen wild-type clones and six of twelve T288D clones grew in soft agar, compared to one of eleven vector and K162M clones. The number of colonies formed in soft agar from two independent clones of each of the transfections was quantitated. The average number of colonies per 200,000 cells plated were: K162M, 32 colonies; wild-type, 470 colonies; and T288D, 250 colonies. Although the T288D Rat1 stables formed fewer colonies than the wild-type AUR2 Rat1 stables, the T288D colonies in general grew to larger size.

The T288D AUR2 mutant was also able transform NIH3T3 cells, as measured by growth in soft agar and growth as tumors in nude mice. In constrast, the wild-type AUR2 was unable to transform NIH3T3 cells. The transforming ability of these constructs correlated with catalytic activity, since the wild-type AUR2 was catalytically inactive in NIH3T3 cells whereas the T288D had strong kinase activity. These data suggest that the genetic background of the cells is important in determining the transforming potential of AUR2.

Example 11

Activated AUR Transforms NIH3T3 Cells

Stable mouse NIH3T3 cell lines that express human AUR2 were established. NIH3T3 cells were infected with retroviruses that express a hemagglutinin (HA)-tagged (Chan 1993, supra) wild-type AUR2 or a kinase inactive mutant where the essential lysine at residue 162 (FIG. 1) was changed to a methionine (K162M). In addition, an activating mutation was made in which the threonine at residue 288 (FIG. 1) in the activation loop was changed to an aspartic acid (T288D). This mutation was designed to mimic constitutive phosphorylation at this site and indeed activates the kinase in vitro. The stable lines expressed similar amounts of AUR2 protein. In vitro kinase assays were performed using the AUR2 protein produced by the stable cell lines.

The wild-type and kinase inactive AUR2 mutant (K162M) were unable to phosphorylate myelin basic protein in vitro, however the activated AUR2 mutant (T288D) had marked activity on this artificial substrate. It is not clear why the wild-type AUR2 appears to be catalytically inactive in the in vitro kinase assay. Perhaps a putative activator of AUR2 is limiting in the NIH3T3 cells or a negative regulator, such as an AUR2 phosphatase, has increased activity in these cells. Indeed, an interfering mutant of the S. cerevisiae phosphatase PP1 can exacerbate the IPL1 mutant phenotype, suggesting that IPL1 may be negatively regulated by this phosphatase (Francisco et al, Mol. Cell. Biol. 14:4731–4740). It is also possible that while activated AUR2 can utilize myelin basic protein as an artificial substrate in vitro, the wild-type kinase has a more restricted substrate preference.

To determine if ectopic expression of activated AUR2 alters the growth of NIH3T3 cells, growth curves in media containing low (2%) serum were generated. For the first 24 hours under these conditions, the expression of activated AUR2 provided a growth advantage to NIH3T3 as compared to cell lines expressing wild-type AUR2, kinase inactive AUR2, or the vector control. However, after 48 hours in 2% serum, all the cell lines ceased to divide, indicating that activated AUR2 alone is unable to promote indefinite cell proliferation.

To characterize the transforming potential of activated AUR2, soft agar assays were performed with the 3T3 clones. The vector control, wild-type, kinase inactive, and activated AUR2 expressing NIH3T3 cells were plated in soft agar and scored for growth after 3–4 weeks. Cells expressing the activated AUR2 grew large colonies in soft agar, in sharp contrast to the lack of growth by cells expressing the wild-type and the kinase inactive AUR2. Ectopic expression of activated AUR2 appears to confer a growth advantage to NIH3T3 cells in low serum and results in anchorage-dependent growth.

Example 12

Aur2 Antisense Oligos Inhibit AUR2 Expression In Vivo

Material and Methods:

Human H1299 cells were seeded at ~40–50% confluency in a 6 well plate (Falcon). The following day lipofectin (Gibco) and oligo(s) were mixed with OptiMEM (Gibco) such that the final concentration of lipofectin is 100 µg/mL and the final concentration of each oligo is 1 µM in a volume of 200 µL. The lipofectin/oligo/OptiMEM mixture was incubated at room temperature (20–25° C.) for 15 minutes, 800 µL of OptiMEM was added to the lipofectin/oligo/OptiMEM mixture, and mixed gently. The growth medium was removed from the H1299 cells, which were at ~80% confluency. Cells were washed once with OptiMEM. The OptiMEM was aspirated, the lipofectin/oligo/OptiMEM mixture was added, cultures incubated at 37° C. for 4 hours. The lipofectin/oligo/OptiMEM mixture was removed and replaced with normal growth medium containing the antisense oligo(s) at a concentration of 200 nM. The plates were returned to the 37° C. incubator for 16–20 hours after which the growth medium was removed from the cells and they were washed once with OptiMEM. The OptiMEM was again aspirated and the lipofectin/oligo/OptiMEM mixture was added (prepared as described above) and the plates again were incubated at 37° C. for 4 hours. The lipofectin/oligo/OptiMEM mixture was removed again and replaced with normal growth medium containing the antisense oligo (s) at a concentration of 200 nM. The plates were returned to the 37° C. incubator for 16–20 hours. The cells were harvested (~40 hours after initial treatment) and analyzed for aur2 mRNA by northern blot or AUR2 protein expression by immunoblot.

Results:

Three antisense oligonucleotides (SEQ ID NOs:16, 17, and 18) which target specific regions of human aur2 mRNA transcript were found to significantly down regulate AUR2 protein expression in the human tumor cell line H1299. When used in combination oligos SEQ ID NO:30 and SEQ ID NO:32 and SEQ ID NO:31 and SEQ ID NO:32 reduce the expression of AUR2 protein below the limit of detection. Treatment of H1299 cells with the combination of SEQ ID NO:31 and SEQ ID NO:32 inhibited the growth of this tumor cell line as measured by cell growth and appeared to induce apoptosis as measured by FACs.

Sequences (5'-3'): The oligo number as well as the location of the sequence within the aur2 cDNA are presented below. Note: these oligonucleotides were synthesized as phosphothionates.

SEQ ID NO:30 (nucleotides 1743–1763): CAGGGCA-GAGTGGTCACTTTC

SEQ ID NO:31 (nucleotides 42–62): CGTCCGCCACTC-CGACCAGCC

SEQ ID NO:32 (nucleotides 1654–1674): TGCAGTC-GAACCTTGCCTCCA

These antisense oligonucleotides would be useful for inhibition of AUR2 expression in normal and tumor cells in order to profile the potential effects of small molecule AUR2 inhibitors. They can also be used to inhibit AUR2 expression in human tumor cell xenografts in nude mice to determine the antitumor effects of AUR2 inhibitors. Another use is as a "drug" to inhibit AUR2 expression in various human tumors that are "driven" by overexpression of the aur2 gene.

Example 13

Screening Systems for the Identification of Inhibitors of AUR2 Activity

Assays may be performed in vitro or in vivo and are described in detail herein or can be obtained by modifying existing assays, such as the growth assay described in patent application Ser. No. 08/487,088, filed Jun. 7, 1995, by Tang et al., and entitled "Novel Pharmaceutical Compounds", or the assays described in patent application Ser. No. 60/005, 167, filed Oct. 13, 1995 by Seedorfet al., and entitled "Diagnosis and Treatment of TKA-1 related disorders", all of which are hereby incorporated herein by reference in their entirety including any drawings. Another assay which could be modified to use the genes of the present invention is described in International Application No. WO 94/23039, published Oct. 13, 1994, hereby incorporated herein by reference in its entirety including any drawings. Other possibilities include detecting kinase activity in an auto-phosphorylation assay or testing for kinase activity on standard substrates such as histones, myelin basic protein, gamma tubulin, or centrosomal proteins. Binding partners may be identified by putting the N-terminal portion of the protein into a two-hybrid screen or detecting phosphotyrosine of a dual specificity kinase (Fields and Song, U.S. Pat. No. 5,283,173, issued Feb. 1, 1994, incorporated by reference herein, including any drawings).

One means by which inhibitors of AUR2 activity may be defined is a screening system using a temperature-sensitive yeast mutant as described by Chan and Botstein (Genetics 135:677–691, 1993); see also Francisco et al. (Mol. Cell. Bio. 14:4731–4740, 1994) both of which are hereby incorporated herein by reference in their entirety including any drawings.

Briefly, yeast strain CCY72-3D-1 (ipl1-2), which expresses a temperature sensitive form of the yeast homologue of AUR2 (ipl1), while viable at 26° C. is incapable of growth at 37° C. Transfection of this strain with an expression plasmid containing a hybrid aurora gene consisting of the N-terminal portion of ipl1, containing the putative substrate interaction domain(s)), and the C-terminal portion of AUR2, containing the catalytic domain, overcomes this sensitivity to growth temperature. The AUR-expressing yeast strain is then grown at 37° C. in the presence of a test substance. No growth will be evident in the presence of substances that inhibit AUR catalytic function. Potential inhibitors include antisense oligonucleotides, small molecular weight chemicals, and/or natural products isolated from diverse organisms such as fungi, marine organisms, plants, etc.

CONCLUSION

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

In view of the degeneracy of the genetic code, other combinations of nucleic acids also encode the claimed peptides and proteins of the invention. For example, all four nucleic acid sequences GCT, GCC, GCA, and GCG encode the amino acide alanine. Therefore, if for an amino acid there exists an average of three codons, a polypeptide of 100 amino acids in length will, on average, be encoded by $3^{100}$, or $5 \times 10^{47}$, nucleic acid sequences. It is understood by those skilled in the art that, with, Thus, a nucleic acid sequence can be modified to form a second nucleic acid sequence, encoding the same polypeptide as endoded by the first second nucleic acid sequences, using routine procedures and without undue experimentation. Thus, all possible nucleic acids that encode the claimed peptides and proteins are also fully described herein, as if all were written out in full taking into account the codon usage, especially that preferred in humans.

Furthermore, changes in the amino acid sequences of polypeptides, or in the corresponding nucleic acid sequence encoding such polypeptide, may be designed or selected to take place in an area of the sequence where the significant activity of the polypeptide remains unchanged. For example, an amino acid change may take place within a β-turn, away from the active site of the polypeptide. Also changes such as deletions (e.g. removal of a segment of the polypeptide, or in the corresponding nucleic acid sequence encoding such polypeptide, which does not affect the active site) and additions (e.g. addition of more peptides to the polypeptide sequence without affecting the function of the active site, such as the formation of GST-fusion proteins, or additions in the corresponding nucleic acid sequence encoding such polypeptide without affecting the function of the active site) are also within the scope of the present invention. Such changes to the polypeptides can be performed by those with ordinary skill in the art using routine procedures and without undue experimentation. Thus, all possible nucleic and/or amino acid sequences that can readily be determined not to affect a significant activity of the peptide or protein of the invention are also fully described herein.

Other embodiments are within the following claims.

What is claimed is:

1. A method for identifying a substance that modulates at least one of AUR-1 or AUR-2 activity comprising the steps of:
   (a) contacting at least one of an AUR-1 polypeptide comprising SEQ ID NO:3 or AUR-2 polypeptide comprising SEQ ID NO:4 with a test substance;
   (b) measuring an activity of said polypeptide; and
   (c) determining whether said substance modulates the activity of said polypeptide.

2. A method of identifying a substance that modulates at least one of AUR-1 or AUR-2 activity in a cell comprising the steps of:
   (a) expressing at least one of an AUR-1 polypeptide comprising SEQ ID NO:3 or AUR-2 polypeptide comprising SEQ ID NO:4 in a cell;
   (b) adding a test substance to said cell; and
   (c) monitoring a change in cell phenotype or the interaction between the AUR-1 or AUR-2 polypeptide and a natural binding partner.

3. The method according to claim 1, wherein step (c) comprises determining whether said substance increases or decreases the probability that a complex will form between at least one of the AUR-1 or AUR-2 polypeptide and a natural binding partner.

4. The method according to claim 3, wherein the occurrence of step (c) depends upon the concentration of said substance.

5. The method according to claim 1, wherein the test substance in step (a) comprises a second substance.

6. The method according to claim 5, wherein the second substance comprises dimethyl sulfoxide (DMSO).

* * * * *

SEQUENCE LISTING (1) GENERAL INFORMATION:

(iii) NUMBER OF SEQUENCES:    39

(2) INFORMATION FOR SEQ ID NO: 1:

(i) SEQUENCE CHARACTERISTICS:
        (A) LENGTH:         1244 base pairs
        (B) TYPE:           nucleic acid
        (C) STRANDEDNESS:   single
        (D) TOPOLOGY:       linear (ii) MOLECULE TYPE:        cDNA (iii) HYPOTHETICAL:        NO (iv) ANTI-SENSE:           NO (vi) ORIGINAL SOURCE:
        (A) ORGANISM:       Homo sapiens (xi) SEQUENCE DESCRIPTION: SEQ ID NO: 1:

```
CGGGAGAGTA GCAGTGCCTT GGACCCCAGC TCTCCTCCCC CTTTCTCTCT AAGGATGGCC    60

CAGAAGGAGA ACTCCTACCC CTGGCCCTAC GGCCGACAGA CGGCTCCATC TGGCCTGAGC   120

ACCCTGCCCC AGCGAGTCCT CCGGAAAGAG CCTGTCACCC CATCTGCACT TGTCCTCATG   180

AGCCGCTCCA ATGTCCAGCC CACAGCTGCC CCTGGCCAGA AGGTGATGGA GAATAGCAGT   240

GGGACACCCG ACATCTTAAC GCGGCACTTC ACAATTGATG ACTTTGAGAT TGGGCGTCCT   300

CTGGGCAAAG GCAAGTTTGG AAACGTGTAC TTGGCTCGGG AGAAGAAAAG CCATTTCATC   360

GTGGCGCTCA AGGTCCTCTT CAAGTCCCAG ATAGAGAAGG AGGGCGTGGA GCATCAGCTG   420

CGCAGAGAGA TCGAAATCCA GGCCCACCTG CACCATCCCA ACATCCTGCG TCTCTACAAC   480

TATTTTTATG ACCGGAGGAG GATCTACTTG ATTCTAGAGT ATGCCCCCCG CGGGGAGCTC   540

TACAAGGAGC TGCAGAAGAG CTGCACATTT GACGAGCAGC GAACAGCCAC GATCATGGAG   600

GAGTTGGCAG ATGCTCTAAT GTACTGCCAT GGGAAGAAGG TGATTCACAG AGACATAAAG   660

CCAGAAAATC TGCTCTTAGG GCTCAAGGGA GAGCTGAAGA TTGCTGACTT CGGCTGGTCT   720

GTGCATGCGC CCTCCCTGAG GAGGAAGACA ATGTGTGGCA CCCTGGACTA CCTGCCCCCA   780

GAGATGATTG AGGGGCGCAT GCACAATGAG AAGGTGGATC TGTGGTGCAT TGGAGTGCTT   840

TGCTATGAGC TGCTGGTGGG GAACCCACCC TTCGAGAGTG CATCACACAA CGAGACCTAT   900

CGCCGCATCG TCAAGGTGGA CCTAAAGTTC CCCGCTTCTG TGCCCACGGG AGCCCAGGAC   960

CTCATCTCCA AACTGCTCAG GCATAACCCC TCGGAACGGC TGCCCCTGGC CCAGGTCTCA  1020

GCCCACCCTT GGGTCCGGGC CAACTCTCGG AGGGTGCTGC CTCCCTCTGC CCTTCAATCT  1080

GTCGCCTGAT GGTCCCTGTC ATTCACTCGG GTGCGTGTGT TTGTATGTCT GTGTATGTAT  1140

AGGGGAAAGA AGGGATCCCT AACTGTTCCC TTATCTGTTT TCTACCTCCT CCTTTGTTTA  1200

ATAAAGGCTG AAGCTTTTTG TAAAAAAACA AAAAAAAAA AAAA                     1244
```

(2) INFORMATION FOR SEQ ID NO: 2:

(i) SEQUENCE CHARACTERISTICS:
        (A) LENGTH:         2198 base pairs
        (B) TYPE:           nucleic acid
        (C) STRANDEDNESS:   single
        (D) TOPOLOGY:       linear (ii) MOLECULE TYPE:        cDNA (iii) HYPOTHETICAL:        NO (iv) ANTI-SENSE:           NO (xi) SEQUENCE DESCRIPTION: SEQ ID NO: 2:

```
GGGATATCTC AGTGGCGGAC GAGGACGGCG GGGACAAGGG GCGGCTGGTC GGAGTGGCGG      60

ACGTCAAGTC CCCTGTCGGT TCCTCCGTCC CTGAGTGTCC TTGGCGCTGC CTTGTGCCCG     120

CCCAGCGCCT TTGCATCCGC TCCTGGGCAC CGAGGCGCCC TGTAGGATAC TGCTTGTTAC     180

TTATTACAGC TAGAGGCATC ATGGACCGAT CTAAAGAAAA CTGCATTTCA GGACCTGTTA     240

AGGCTACAGC TCCAGTTGGA GGTCCAAAAC GTGTTCTCGT GACTCAGCAA TTTCCTTGTC     300

AGAATCCATT ACCTGTAAAT AGTGGCCAGG CTCAGCGGGT CTTGTGTCCT TCAAATTCTT     360

CCCAGCGCGT TCCTTTGCAA GCACAAAAGC TTGTCTCCAG TCACAAGCCG GTTCAGAATC     420

AGAAGCAGAA GCAATTGCAG GCAACCAGTG TACCTCATCC TGTCTCCAGG CCACTGAATA     480

ACACCCAAAA GAGCAAGCAG CCCCTGCCAT CGGCACCTGA AAATAATCCT GAGGAGGAAC     540

TGGCATCAAA ACAGAAAAAT GAAGAATCAA AAAGAGGCA GTGGGCTTTG AAGACTTTG      600

AAATTGGTCG CCCTCTGGGT AAAGGAAAGT TTGGTAATGT TTATTTGGCA AGAGAAAAGC     660

AAAGCAAGTT TATTCTGGCT CTTAAAGTGT TATTTAAAGC TCAGCTGGAG AAAGCCGGAG     720

TGGAGCATCA GCTCAGAAGA GAAGTAGAAA TACAGTCCCA CCTTCGGCAT CCTAATATTC     780

TTAGACTGTA TGGTTATTTC CATGATGCTA CCAGAGTCTA CCTAATTCTG GAATATGCAC     840

CACTTGGAAC AGTTTATAGA GAACTTCAGA AACTTTCAAA GTTTGATGAG CAGAGAACTG     900

CTACTTATAT AACAGAATTG GCAAATGCCC TGTCTTACTG TCATTCGAAG AGAGTTATTC     960

ATAGAGACAT TAAGCCAGAG AACTTACTTC TTGGATCAGC TGGAGAGCTT AAAATTGCAG    1020

ATTTTGGGTG GTCAGTACAT GCTCCATCTT CCAGGAGGAC CACTCTCTGT GGCACCCTGG    1080

ACTACCTGCC CCCTGAAATG ATTGAAGGTC GGATGCATGA TGAGAAGGTG GATCTCTGGA    1140

GCCTTGGAGT TCTTTGCTAT GAATTTTTAG TTGGGAAGCC TCCTTTTGAG GCAAACACAT    1200

ACCAAGAGAC CTACAAAAGA ATATCACGGG TTGAATTCAC ATTCCCTGAC TTTGTAACAG    1260

AGGGAGCCAG GGACCTCATT TCAAGACTGT TGAAGCATAA TCCCAGCCAG AGGCCAATGC    1320

TCAGAGAAGT ACTTGAACAC CCCTGGATCA CAGCAAATTC ATCAAAACCA TCAAATTGCC    1380

AAAACAAAGA ATCAGCTAGC AAACAGTCTT AGGAATCGTG CAGGGGGAGA AATCCTTGAG    1440

CCAGGGCTGC CATATAACCT GACAGGAACA TGCTACTGAA GTTTATTTTA CCATTGACTG    1500

CTGCCCTCAA TCTAGAACGC TACACAAGAA ATATTTGTTT TACTCAGCAG GTGTGCCTTA    1560

ACCTCCCTAT TCAGAAAGCT CCACATCAAT AAACATGACA CTCTGAAGTG AAAGTAGCCA    1620

CGAGAATTGT GCTACTTATA CTGGTTCATA ATCTGGAGGC AAGGTTCGAC TGCAGCCGCC    1680

CCGTCAGCCT GTGCTAGGCA TGGTGTCTTC ACAGGAGGCA AATCCAGAGC CTGGCTGTGG    1740

GGAAAGTGAC CACTCTGCCC TGACCCCGAT CAGTTAAGGA GCTGTGCAAT AACCTTCCTA    1800

GTACCTGAGT GAGTGTGTAA CTTATTGGGT TGGCGAAGCC TGGTAAAGCT GTTGGAATGA    1860

GTATGTGATT CTTTTTAAGT ATGAAAATAA AGATATATGT ACAGACTTGT ATTTTTTCTC    1920

TGGTGGCATT CCTTTAGGAA TGCTGTGTGT CTGTCCGGCA CCCCGGTAGG CCTGATTGGG    1980

TTTCTAGTCC TCCTTAACCA CTTATCTCCC ATATGAGAGT GTGAAAAATA GGAACACGTG    2040

CTCTACCTCC ATTTAGGGAT TTGCTTGGGA TACAGAAGAG GCCATGTGTC TCAGAGCTGT    2100

TAAGGGCTTA TTTTTTTAAA ACATTGGAGT CATAGCATGT GTGTAAACTT TAAATATGCA    2160

AATAAATAAG TATCTATGTC AAAAAAAAAA AAAAAAA                             2198
```

(2) INFORMATION FOR SEQ ID NO: 3:

(i) SEQUENCE CHARACTERISTICS:

|         |                      |                  |
|---------|----------------------|------------------|
|         | (A) LENGTH:          | 344 amino acids  |
|         | (B) TYPE:            | amino acid       |
|         | (C) STRANDEDNESS:    | single           |
|         | (D) TOPOLOGY:        | linear           |
| (ii)    | MOLECULE TYPE:       | protein          |
| (iii)   | HYPOTHETICAL:        | NO               |
| (iv)    | ANTI-SENSE:          | NO               |

(xi) SEQUENCE DESCRIPTION: SEQ ID NO: 3:

```
Met Ala Gln Lys Glu Asn Ser Tyr Pro Trp Pro Tyr Gly Arg Gln Thr
  1               5                  10                  15

Ala Pro Ser Gly Leu Ser Thr Leu Pro Gln Arg Val Leu Arg Lys Glu
             20                  25                  30

Pro Val Thr Pro Ser Ala Leu Val Leu Met Ser Arg Ser Asn Val Gln
         35                  40                  45

Pro Thr Ala Ala Pro Gly Gln Lys Val Met Glu Asn Ser Ser Gly Thr
     50                  55                  60

Pro Asp Ile Leu Thr Arg His Phe Thr Ile Asp Asp Phe Glu Ile Gly
 65                  70                  75                  80

Arg Pro Leu Gly Lys Gly Lys Phe Gly Asn Val Tyr Leu Ala Arg Glu
                 85                  90                  95

Lys Lys Ser His Phe Ile Val Ala Leu Lys Val Leu Phe Lys Ser Gln
                100                 105                 110

Ile Glu Lys Glu Gly Val Glu His Gln Leu Arg Arg Glu Ile Glu Ile
            115                 120                 125

Gln Ala His Leu His His Pro Asn Ile Leu Arg Leu Tyr Asn Tyr Phe
        130                 135                 140

Tyr Asp Arg Arg Arg Ile Tyr Leu Ile Leu Glu Tyr Ala Pro Arg Gly
145                 150                 155                 160

Glu Leu Tyr Lys Glu Leu Gln Lys Ser Cys Thr Phe Asp Glu Gln Arg
                165                 170                 175

Thr Ala Thr Ile Met Glu Glu Leu Ala Asp Ala Leu Met Tyr Cys His
            180                 185                 190

Gly Lys Lys Val Ile His Arg Asp Ile Lys Pro Glu Asn Leu Leu Leu
        195                 200                 205

Gly Leu Lys Gly Glu Leu Lys Ile Ala Asp Phe Gly Trp Ser Val His
    210                 215                 220

Ala Pro Ser Leu Arg Arg Lys Thr Met Cys Gly Thr Leu Asp Tyr Leu
225                 230                 235                 240

Pro Pro Glu Met Ile Glu Gly Arg Met His Asn Glu Lys Val Asp Leu
                245                 250                 255

Trp Cys Ile Gly Val Leu Cys Tyr Glu Leu Leu Val Gly Asn Pro Pro
            260                 265                 270

Phe Glu Ser Ala Ser His Asn Glu Thr Tyr Arg Arg Ile Val Lys Val
        275                 280                 285

Asp Leu Lys Phe Pro Ala Ser Val Pro Thr Gly Ala Gln Asp Leu Ile
    290                 295                 300

Ser Lys Leu Leu Arg His Asn Pro Ser Glu Arg Leu Pro Leu Ala Gln
305                 310                 315                 320

Val Ser Ala His Pro Trp Val Arg Ala Asn Ser Arg Arg Val Leu Pro
                325                 330                 335

Pro Ser Ala Leu Gln Ser Val Ala
            340
```

(2) INFORMATION FOR SEQ ID NO: 4:

(i) SEQUENCE CHARACTERISTICS:
        (A) LENGTH: 403 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 4:

```
Met Asp Arg Ser Lys Glu Asn Cys Ile Ser Gly Pro Val Lys Ala Thr
1               5                   10                  15

Ala Pro Val Gly Gly Pro Lys Arg Val Leu Val Thr Gln Gln Phe Pro
            20                  25                  30

Cys Gln Asn Pro Leu Pro Val Asn Ser Gly Gln Ala Gln Arg Val Leu
        35                  40                  45

Cys Pro Ser Asn Ser Ser Gln Arg Val Pro Leu Gln Ala Gln Lys Leu
    50                  55                  60

Val Ser Ser His Lys Pro Val Gln Asn Gln Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
            100                 105                 110

Glu Leu Ala Ser Lys Gln Lys Asn Glu Glu Ser Lys Lys Arg Gln Trp
        115                 120                 125

Ala Leu Glu Asp Phe Glu Ile Gly Arg Pro Leu Gly Lys Gly Lys Phe
    130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175

Gln Leu Arg Arg Glu Val Glu Ile Gln Ser His Leu Arg His Pro Asn
            180                 185                 190

Ile Leu Arg Leu Tyr Gly Tyr Phe His Asp Ala Thr Arg Val Tyr Leu
        195                 200                 205

Ile Leu Glu Tyr Ala Pro Leu Gly Thr Val Tyr Arg Glu Leu Gln Lys
    210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
                245                 250                 255

Ile Lys Pro Glu Asn Leu Leu Leu Gly Ser Ala Gly Glu Leu Lys Ile
            260                 265                 270

Ala Asp Phe Gly Trp Ser Val His Ala Pro Ser Ser Arg Arg Thr Thr
        275                 280                 285

Leu Cys Gly Thr Leu Asp Tyr Leu Pro Pro Glu Met Ile Glu Gly Arg
    290                 295                 300

Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                325                 330                 335
```

```
Thr Tyr Lys Arg Ile Ser Arg Val Glu Phe Thr Phe Pro Asp Phe Val
            340                 345                 350

Thr Glu Gly Ala Arg Asp Leu Ile Ser Arg Leu Leu Lys His Asn Pro
            355                 360                 365

Ser Gln Arg Pro Met Leu Arg Glu Val Leu Glu His Pro Trp Ile Thr
        370                 375                 380

Ala Asn Ser Ser Lys Pro Ser Asn Cys Gln Asn Lys Glu Ser Ala Ser
385                 390                 395                 400

Lys Gln Ser
```

(2) INFORMATION FOR SEQ ID NO: 5:

(i) SEQUENCE CHARACTERISTICS:
        (A) LENGTH:          11 amino acids
        (B) TYPE:            amino acid
        (C) STRANDEDNESS:    single
        (D) TOPOLOGY:        linear (ii) MOLECULE TYPE:       Peptide (xi) SEQUENCE DESCRIPTION: SEQ ID NO: 5:

```
Glu Asn Ser Tyr Pro Trp Pro Tyr Gly Arg Gln
1               5                   10
```

(2) INFORMATION FOR SEQ ID NO: 6:

(i) SEQUENCE CHARACTERISTICS:
        (A) LENGTH:          5 amino acids
        (B) TYPE:            amino acid
        (C) STRANDEDNESS:    single
        (D) TOPOLOGY:        linear (ii) MOLECULE TYPE:       Peptide (xi) SEQUENCE DESCRIPTION: SEQ ID NO: 6:

```
Cys Ile Ser Gly Pro
1               5
```

(2) INFORMATION FOR SEQ ID NO: 7:

(i) SEQUENCE CHARACTERISTICS:
        (A) LENGTH:          4 amino acids
        (B) TYPE:            amino acid
        (C) STRANDEDNESS:    single
        (D) TOPOLOGY:        linear (ii) MOLECULE TYPE:       Peptide (xi) SEQUENCE DESCRIPTION: SEQ ID NO: 7:

```
Gln Phe Pro Gln
1
```

(2) INFORMATION FOR SEQ ID NO: 8:

(i) SEQUENCE CHARACTERISTICS:
        (A) LENGTH:          5 amino acids
        (B) TYPE:            amino acid
        (C) STRANDEDNESS:    single
        (D) TOPOLOGY:        linear (ii) MOLECULE TYPE:       Peptide (xi) SEQUENCE DESCRIPTION: SEQ ID NO: 8:

```
Val Asn Ser Gly Gln
1               5
```

(2) INFORMATION FOR SEQ ID NO: 9:

(i) SEQUENCE CHARACTERISTICS:
        (A) LENGTH:         11 amino acids
        (B) TYPE:           amino acid
        (C) STRANDEDNESS:   single
        (D) TOPOLOGY:      linear (ii) MOLECULE TYPE:      Peptide (xi) SEQUENCE DESCRIPTION: SEQ ID NO: 9:

```
Arg Lys Glu Pro Val Thr Pro Ser Ala Leu Val
1               5                   10
```

(2) INFORMATION FOR SEQ ID NO: 10:

(i) SEQUENCE CHARACTERISTICS:
        (A) LENGTH:         13 amino acids
        (B) TYPE:           amino acid
        (C) STRANDEDNESS:   single
        (D) TOPOLOGY:      linear (ii) MOLECULE TYPE:      Peptide (xi) SEQUENCE DESCRIPTION: SEQ ID NO: 10:

```
Leu Met Ser Arg Ser Asn Val Gln Pro Thr Ala Ala Pro
1               5                   10
```

(2) INFORMATION FOR SEQ ID NO: 11:

(i) SEQUENCE CHARACTERISTICS:
        (A) LENGTH:         16 amino acids
        (B) TYPE:           amino acid
        (C) STRANDEDNESS:   single
        (D) TOPOLOGY:      linear (ii) MOLECULE TYPE:      Peptide (xi) SEQUENCE DESCRIPTION: SEQ ID NO: 11:

```
Val Gln Asn Gln Lys Gln Lys Gln Leu Gln Ala Thr Ser Val Pro His
1               5                   10                  15
```

(2) INFORMATION FOR SEQ ID NO: 12:

(i) SEQUENCE CHARACTERISTICS:
        (A) LENGTH:         11 amino acids
        (B) TYPE:           amino acid
        (C) STRANDEDNESS:   single
        (D) TOPOLOGY:      linear (ii) MOLECULE TYPE:      Peptide (xi) SEQUENCE DESCRIPTION: SEQ ID NO: 12:

```
Pro Val Ser Arg Pro Leu Asn Asn Thr Gln Lys
1               5                   10
```

(2) INFORMATION FOR SEQ ID NO: 13:

(i) SEQUENCE CHARACTERISTICS:
        (A) LENGTH:         10 amino acids
        (B) TYPE:           amino acid
        (C) STRANDEDNESS:   single
        (D) TOPOLOGY:      linear (ii) MOLECULE TYPE:      Peptide (xi) SEQUENCE DESCRIPTION: SEQ ID NO: 13:

```
Val Met Glu Asn Ser Ser Gly Thr Pro Asp
1               5                   10
```

(2) INFORMATION FOR SEQ ID NO: 14:

(i) SEQUENCE CHARACTERISTICS:
        (A) LENGTH:         9 amino acids
        (B) TYPE:           amino acid
        (C) STRANDEDNESS:  single
        (D) TOPOLOGY:      linear (ii) MOLECULE TYPE:       Peptide (xi) SEQUENCE DESCRIPTION: SEQ ID NO: 14:

Ile Leu Thr Arg His Phe Thr Ile Asp
1           5

(2) INFORMATION FOR SEQ ID NO: 15:

(i) SEQUENCE CHARACTERISTICS:
        (A) LENGTH:         22 amino acids
        (B) TYPE:           amino acid
        (C) STRANDEDNESS:  single
        (D) TOPOLOGY:      linear (ii) MOLECULE TYPE:       Peptide (xi) SEQUENCE DESCRIPTION: SEQ ID NO: 15:

Ser Lys Gln Pro Leu Pro Ser Ala Pro Glu Asn Asn Pro Glu Glu Gln
1           5                  10               15

Leu Ala Ser Lys Gln Lys
         20

(2) INFORMATION FOR SEQ ID NO: 16:

(i) SEQUENCE CHARACTERISTICS:
        (A) LENGTH:         23 base pairs
        (B) TYPE:           nucleic acid
        (C) STRANDEDNESS:  single
        (D) TOPOLOGY:      linear (ix) FEATURE:
        (D) OTHER INFORMATION:   The letter "R" stands for A or G.
            The letter "Y" stands for C or T.
            The letter "N" stands for A, C, G or T.

(xi) SEQUENCE DESCRIPTION: SEQ ID NO: 16:

GARTTYGGNG ARGTNTTYYT NGC                                           23

(2) INFORMATION FOR SEQ ID NO: 17:

(i) SEQUENCE CHARACTERISTICS:
        (A) LENGTH:         23 base pairs
        (B) TYPE:           nucleic acid
        (C) STRANDEDNESS:  single
        (D) TOPOLOGY:      linear (ix) FEATURE:
        (D) OTHER INFORMATION:   The letter "N" stands for A, C,
            G or T. The letter "R" stands for A or G.

(xi) SEQUENCE DESCRIPTION: SEQ ID NO: 17:

AGNACNCCRA ANGCCCACAC RTC                                           23

(2) INFORMATION FOR SEQ ID NO: 18:

(i) SEQUENCE CHARACTERISTICS:
        (A) LENGTH:         8 amino acids
        (B) TYPE:           amino acid
        (C) STRANDEDNESS:  single
        (D) TOPOLOGY:      linear

```
        (ii) MOLECULE TYPE:          Peptide (xi) SEQUENCE DESCRIPTION: SEQ ID NO:  18:

Glu Phe Gly Glu Val Phe Leu Ala
 1               5

(2) INFORMATION FOR SEQ ID NO: 19:

(i) SEQUENCE CHARACTERISTICS:
            (A) LENGTH:              25 base pairs
            (B) TYPE:                nucleic acid
            (C) STRANDEDNESS:        single
            (D) TOPOLOGY:            linear (xi) SEQUENCE DESCRIPTION: SEQ ID NO:  19:

TTTGGCTCGG GAGAAGAAAA GCCAT                                               25

(2) INFORMATION FOR SEQ ID NO: 20:

(i) SEQUENCE CHARACTERISTICS:
            (A) LENGTH:              24 base pairs
            (B) TYPE:                nucleic acid
            (C) STRANDEDNESS:        single
            (D) TOPOLOGY:            linear (xi) SEQUENCE DESCRIPTION: SEQ ID NO:  20:

CAATCATCTC TGGGGGCAGG TAGT                                                24

(2) INFORMATION FOR SEQ ID NO: 21:

(i) SEQUENCE CHARACTERISTICS:
            (A) LENGTH:              10 amino acids
            (B) TYPE:                amino acid
            (C) STRANDEDNESS:        single
            (D) TOPOLOGY:            linear (ii) MOLECULE TYPE:          Peptide (xi) SEQUENCE DESCRIPTION: SEQ ID NO:  21:

Tyr Pro Tyr Asp Val Pro Asp Tyr Ala Ser
 1               5                  10

(2) INFORMATION FOR SEQ ID NO: 22:

(i) SEQUENCE CHARACTERISTICS:
            (A) LENGTH:              14 amino acids
            (B) TYPE:                amino acid
            (C) STRANDEDNESS:        single
            (D) TOPOLOGY:            linear (ii) MOLECULE TYPE:          Peptide (xi) SEQUENCE DESCRIPTION: SEQ ID NO:  22:

Ser Ala Pro Glu Asn Asn Pro Glu Glu Gln Leu Ala Ser Lys
 1               5                  10

(2) INFORMATION FOR SEQ ID NO: 23:

(i) SEQUENCE CHARACTERISTICS:
            (A) LENGTH:              13 amino acids
            (B) TYPE:                amino acid
            (C) STRANDEDNESS:        single
            (D) TOPOLOGY:            linear (ii) MOLECULE TYPE:          Peptide (xi) SEQUENCE DESCRIPTION: SEQ ID NO:  23:
```

```
Arg Pro Leu Asn Asn Thr Gln Lys Ser Lys Gln Pro Leu
1               5                   10
```

(2) INFORMATION FOR SEQ ID NO: 24:

(i) SEQUENCE CHARACTERISTICS:
        (A) LENGTH:         13 amino acids
        (B) TYPE:           amino acid
        (C) STRANDEDNESS:   single
        (D) TOPOLOGY:       linear (ii) MOLECULE TYPE:      Peptide (xi) SEQUENCE DESCRIPTION: SEQ ID NO: 24:

```
Met Ala Gln Lys Glu Asn Ser Tyr Pro Trp Pro Tyr Gly
1               5                   10
```

(2) INFORMATION FOR SEQ ID NO: 25:

(i) SEQUENCE CHARACTERISTICS:
        (A) LENGTH:         13 amino acids
        (B) TYPE:           amino acid
        (C) STRANDEDNESS:   single
        (D) TOPOLOGY:       linear (ii) MOLECULE TYPE:      Peptide (xi) SEQUENCE DESCRIPTION: SEQ ID NO: 25:

```
Pro Gly Gln Lys Val Met Glu Asn Ser Ser Gly Thr Pro
1               5                   10
```

(2) INFORMATION FOR SEQ ID NO: 26:

(i) SEQUENCE CHARACTERISTICS:
        (A) LENGTH:         8 amino acids
        (B) TYPE:           amino acid
        (C) STRANDEDNESS:   single
        (D) TOPOLOGY:       linear (ii) MOLECULE TYPE:      Peptide (ix) FEATURE:
        (D) OTHER INFORMATION:   "Xaa" in positions 2, 4, 5
            and 7 stands for an unidentified amino acid.

(xi) SEQUENCE DESCRIPTION: SEQ ID NO: 26:

```
Gly Xaa Gly Xaa Xaa Gly Xaa Val
1               5
```

(2) INFORMATION FOR SEQ ID NO: 27:

(i) SEQUENCE CHARACTERISTICS:
        (A) LENGTH:         9 amino acids
        (B) TYPE:           amino acid
        (C) STRANDEDNESS:   single
        (D) TOPOLOGY:       linear (ii) MOLECULE TYPE:      Peptide (xi) SEQUENCE DESCRIPTION: SEQ ID NO: 27:

```
Asp Val Trp Ser Tyr Phe Gly Ile Val
1               5
```

(2) INFORMATION FOR SEQ ID NO: 28:

(i) SEQUENCE CHARACTERISTICS:
        (A) LENGTH:         9 amino acids
        (B) TYPE:           amino acid
        (C) STRANDEDNESS:   single
        (D) TOPOLOGY:       linear

```
        (ii) MOLECULE TYPE:          Peptide (ix) FEATURE:
              (D) OTHER INFORMATION:  "Xaa" in positions 2 and 6 stands
                  for an unidentified amino acid.

(xi) SEQUENCE DESCRIPTION: SEQ ID NO: 28:

Asp Xaa Trp Ala Ser Xaa Gly Ile Val
 1               5

(2) INFORMATION FOR SEQ ID NO: 29:

(i) SEQUENCE CHARACTERISTICS:
              (A) LENGTH:             8 amino acids
              (B) TYPE:               amino acid
              (C) STRANDEDNESS:       single
              (D) TOPOLOGY:           linear (ii) MOLECULE TYPE:           Peptide (ix) FEATURE:
              (D) OTHER INFORMATION:  "Xaa" in position 4 represents
                  either Asp or Ser.

(xi) SEQUENCE DESCRIPTION: SEQ ID NO: 29:

Asp Val Trp Xaa Phe Gly Val Leu
 1               5

(2) INFORMATION FOR SEQ ID NO: 30:

(i) SEQUENCE CHARACTERISTICS:
              (A) LENGTH:             21 base pairs
              (B) TYPE:               nucleic acid
              (C) STRANDEDNESS:       single
              (D) TOPOLOGY:           linear (xi) SEQUENCE DESCRIPTION: SEQ ID NO: 30:

CAGGGCAGAG TGGTCACTTT C                                              21

(2) INFORMATION FOR SEQ ID NO: 31:

(i) SEQUENCE CHARACTERISTICS:
              (A) LENGTH:             21 base pairs
              (B) TYPE:               nucleic acid
              (C) STRANDEDNESS:       single
              (D) TOPOLOGY:           linear (xi) SEQUENCE DESCRIPTION: SEQ ID NO: 31:

CGTCCGCCAC TCCGACCAGC C                                              21

(2) INFORMATION FOR SEQ ID NO: 32:

(i) SEQUENCE CHARACTERISTICS:
              (A) LENGTH:             21 base pairs
              (B) TYPE:               nucleic acid
              (C) STRANDEDNESS:       single
              (D) TOPOLOGY:           linear (xi) SEQUENCE DESCRIPTION: SEQ ID NO: 32:

TGCAGTCGAA CCTTGCCTCC A                                              21

(2) INFORMATION FOR SEQ ID NO: 33:

(i) SEQUENCE CHARACTERISTICS:
              (A) LENGTH:             8 amino acids
              (B) TYPE:               amino acid
              (C) STRANDEDNESS:       single
              (D) TOPOLOGY:           linear
```

```
        (ii) MOLECULE TYPE:         Peptide (xi) SEQUENCE DESCRIPTION: SEQ ID NO: 33:

Asp Val Trp Ala Phe Gly Val Leu
1

(2) INFORMATION FOR SEQ ID NO: 34:

(i) SEQUENCE CHARACTERISTICS:
        (A) LENGTH:                20 base pairs
        (B) TYPE:                  nucleic acid
        (C) STRANDEDNESS:          single
        (D) TOPOLOGY:              linear (xi) SEQUENCE DESCRIPTION: SEQ ID NO: 34:

CGCCTTTGCA TCCGCTCCTG                                                  20

(2) INFORMATION FOR SEQ ID NO: 35:

(i) SEQUENCE CHARACTERISTICS:
        (A) LENGTH:                20 base pairs
        (B) TYPE:                  nucleic acid
        (C) STRANDEDNESS:          single
        (D) TOPOLOGY:              linear (xi) SEQUENCE DESCRIPTION: SEQ ID NO: 35:

GATTTGCCTC CTGTGAAGAC                                                  20

(2) INFORMATION FOR SEQ ID NO: 36:

(i) SEQUENCE CHARACTERISTICS:
        (A) LENGTH:                21 base pairs
        (B) TYPE:                  nucleic acid
        (C) STRANDEDNESS:          single
        (D) TOPOLOGY:              linear (xi) SEQUENCE DESCRIPTION: SEQ ID NO: 36:

ATGCCTCCGG AAAGAGCCTG T                                                21

(2) INFORMATION FOR SEQ ID NO: 37:

(i) SEQUENCE CHARACTERISTICS:
        (A) LENGTH:                22 base pairs
        (B) TYPE:                  nucleic acid
        (C) STRANDEDNESS:          single
        (D) TOPOLOGY:              linear (xi) SEQUENCE DESCRIPTION: SEQ ID NO: 37:

GTGTCCCACT GCTATTCTCC AT                                               22

(2) INFORMATION FOR SEQ ID NO: 38:

(i) SEQUENCE CHARACTERISTICS:
        (A) LENGTH:                21 base pairs
        (B) TYPE:                  nucleic acid
        (C) STRANDEDNESS:          single
        (D) TOPOLOGY:              linear (xi) SEQUENCE DESCRIPTION: SEQ ID NO: 38:

CAGGGCTGCC ATATAACCTG A                                                21

(2) INFORMATION FOR SEQ ID NO: 39:

(i) SEQUENCE CHARACTERISTICS:
        (A) LENGTH:                20 base pairs
        (B) TYPE:                  nucleic acid
```

```
            (C) STRANDEDNESS:       single
            (D) TOPOLOGY:           linear (xi) SEQUENCE DESCRIPTION: SEQ ID NO: 39:

CTAGCACAGG CTGACGGGGC                                              20
```